(12) United States Patent  
Benson et al.

(10) Patent No.: US 8,088,930 B2
(45) Date of Patent: Jan. 3, 2012

(54) BENZIMIDAZOLE DERIVATIVES

(75) Inventors: Gregory Martin Benson, Therwil (CH); Konrad Bleicher, Freiburg (DE); Song Feng, Shanghai (CN); Uwe Grether, Efringen-Kirchen (DE); Bernd Kuhn, Reinach BL (CH); Rainer E. Martin, Basel (CH); Jean-Marc Plancher, Hagenthal-le-Bas (FR); Hans Richter, Grenzach-Wyhlen (DE); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 151 days.

(21) Appl. No.: 12/554,023

(22) Filed: Sep. 4, 2009

(65) Prior Publication Data

US 2010/0063101 A1     Mar. 11, 2010

(30) Foreign Application Priority Data

Sep. 11, 2008 (EP) .................................... 08164184

(51) Int. Cl.
*A61K 31/4184* (2006.01)
*C07D 235/12* (2006.01)

(52) U.S. Cl. ..................................... 548/310.7; 514/394
(58) Field of Classification Search ............... 548/310.7
See application file for complete search history.

(56) References Cited

U.S. PATENT DOCUMENTS

| | | | | |
|---|---|---|---|---|
| 3,080,282 | A * | 3/1963 | Shunk | 514/394 |
| 7,252,925 | B2 * | 8/2007 | Watanabe et al. | 430/270.1 |
| 2009/0197889 | A1 | 8/2009 | Winfield | |

FOREIGN PATENT DOCUMENTS

| | | |
|---|---|---|
| WO | WO 2008/000643 | 1/2008 |
| WO | WO 2009/027264 | 3/2009 |
| WO | WO 2009/062874 | 5/2009 |
| WO | WO 2009/080555 | 7/2009 |

OTHER PUBLICATIONS

Hughes, D.L., Org. Prep. Proceed. Int., 28, pp. 127-164 (1996).
But et al., Chemistry Asian J., 2, pp. 1340-1355 (2007).
Vlasov, V.M., Russian Chem. Rev., 72, pp. 681-703 (2003).
Zoltewicz, J.A., "New Directions in Aromatic Nucleophilic Substitution" Topics Curr. Chem., Organic Syntheses, 59, pp. 33-64 (1975).
Tempest et al., Tet. Lett., 42, pp. 4959-4962 (2001).
Zhang et al., Tet. Lett., 45, pp. 6757-6760 (2004).
Ugi, I., "The Four Component Synthesis", The Peptides, vol. 2, Academic Press, NY, pp. 365-381 (1980).
Tempest et al., Tet. Lett., 42, pp. 4963-4968 (2001).

* cited by examiner

*Primary Examiner* — Laura L. Stockton
(74) *Attorney, Agent, or Firm* — George W. Johnston; Patricia S. Rocha-Tramaloni; Gene J. Yao

(57) ABSTRACT

The invention is concerned with novel benzimidazole derivatives of formula (I)

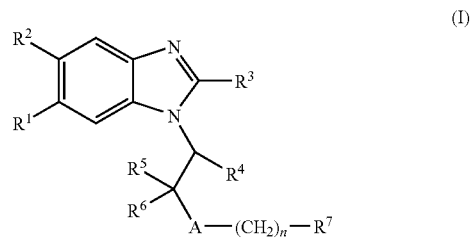

(I)

wherein A, n and $R^1$ to $R^7$ are as defined in the description and in the claims, as well as physiologically acceptable salts and esters thereof. These compounds can be used as medicaments.

21 Claims, No Drawings

BENZIMIDAZOLE DERIVATIVES

PRIORITY TO RELATED APPLICATION(S)

This application claims the benefit of European Patent Application No. 08164184.7, filed Sep. 11, 2008, which is hereby incorporated by reference in its entirety.

BACKGROUND OF THE INVENTION

The Farnesoid-X-receptor (FXR) is a member of the nuclear hormone receptor superfamily of transcription factors. FXR was originally identified as a receptor activated by farnesol, and subsequent studies revealed a major role of FXR as a bile acid receptor [Makishima, M., Okamoto, A. Y., Repa, J. J., Tu, H., Learned, R. M., Luk, A., Hull, M. V., Lustig, K. D., Mangelsdorf, D. J. and Shan, B. Identification of a nuclear receptor for bile acids. *Science* 1999, 284, 1362-1365]. FXR is expressed in liver, intestine, kidney, and the adrenal gland. Four splice isoforms have been cloned in humans.

Among the major bile acids, chenodeoxycholic acid is the most potent FXR agonist. Binding of bile acids or synthetic ligands to FXR induces the transcriptional expression of small heterodimer partner (SHP), an atypical nuclear receptor family member that binds to several other nuclear hormone receptors, including LRH-1 and LXRalpha and blocks their transcriptional functions [Lu, T. T., Makishima, M., Repa, J. J., Schoonjans, K., Kerr, T. A., Auwerx, J. and Mangelsdorf, D. J. Molecular basis for feedback regulation of bile acid synthesis by nuclear receptors. *Mol. Cell.* 2000, 6, 507-515]. CYP7A1 and CYP8B are enzymes involved in hepatic bile acid synthesis. FXR represses their expression via activation of the SHP pathway. FXR directly induces the expression of bile acid-exporting transporters for the ABC family in hepatocytes, including the bile salt export pump (ABCB11) and the multidrug resistance associated protein 2 (ABCC2) [Kast, H. R., Goodwin, B., Tarr, P. T., Jones, S. A., Anisfeld, A. M., Stoltz, C. M., Tontonoz, P., Kliewer, S., Willson, T. M. and Edwards, P. A. Regulation of multidrug resistance-associated protein 2 (ABCC2) by the nuclear receptors pregnane X receptor, farnesoid X-activated receptor, and constitutive androstane receptor. *J. Biol. Chem.* 2002, 277, 2908-2915; Ananthanarayanan, M., Balasubramanian, N., Makishima, M., Mangelsdorf, D. J. and Suchy, F. J. Human bile salt export pump promoter is transactivated by the farnesoid X receptor/bile acid receptor. *J. Biol. Chem.* 2001, 276, 28857-28865]. FXR knockout mice have impaired resistance to bile acid-induced hepatotoxicity and synthetic FXR agonists have been shown to be hepatoprotective in animal models of cholestasis [Liu, Y., Binz, J., Numerick, M. J., Dennis, S., Luo, G., Desai, B., MacKenzie, K. I., Mansfield, T. A., Kliewer, S. A., Goodwin, B. and Jones, S. A. Hepatoprotection by the farnesoid X receptor agonist GW4064 in rat models of intra- and extra-hepatic cholestasis. *J. Clin. Invest.* 2003, 112, 1678-1687; Sinal, C. J., Tohkin, M., Miyata, M., Ward, J. M., Lambert, G. and Gonzalez, F. J. Targeted disruption of the nuclear receptor FXR/BAR impairs bile acid and lipid homeostasis. *Cell* 2000, 102, 731-744]. These data show that FXR protects hepatocytes from bile acid toxicity by suppressing both cellular synthesis and import of bile acids and stimulating their biliary excretion.

The process of enterohepatic circulation of bile acids is also a major regulator of serum cholesterol homeostasis. After biosynthesis from cholesterol in the liver, bile acids are secreted with bile into the lumen of the small intestine to aid in the digestion and absorption of fat and fat-soluble vitamins. The ratio of different bile acids determines their ability to solubilize cholesterol. FXR activation decreases the size and changes the composition of the bile acid pool, decreasing the intestinal solubilization of cholesterol, effectively blocking its absorption. Decreased absorption would be expected to result in lower plasma cholesterol levels. Indeed direct inhibitors of cholesterol absorption such as ezetimibe decrease plasma cholesterol, providing some evidence to support this hypothesis. However ezetimibe has limited efficacy which appears due to feedback upregulation of cholesterol synthesis in cells attempting to compensate for depletion of cholesterol. Recent data have shown that FXR opposes this effect in part by directly repressing the expression of HMGCoA reductase via a pathway involving SHP and LRH1 [Datta, S., Wang, L., Moore, D. D. and Osborne, T. F. Regulation of 3-hydroxy-3-methylglutaryl coenzyme A reductase promoter by nuclear receptors liver receptor homologue-1 and small heterodimer partner: a mechanism for differential regulation of cholesterol synthesis and uptake. *J. Biol. Chem.* 2006, 281, 807-812]. FXR also decreases hepatic synthesis of triglycerides by repressing SREBP1-c expression by an alternate pathway involving SHP and LXRalpha. Thus compounds that activate FXR may show superior therapeutic efficacy on plasma cholesterol and triglyceride lowering than current therapies.

Most patients with coronary artery disease have high plasma levels of atherogenic LDL. The HMGCoA reductase inhibitors (statins) are effective at normalizing LDL-C levels but reduce the risk for cardiovascular events such as stroke and myocardial infarction by only about 30%. Additional therapies targeting further lowering of atherogenic LDL as well as other lipid risk factors such as high plasma triglyceride levels and low HDL-C levels are needed.

A high proportion of type 2 diabetic patients in the United States have abnormal concentrations of plasma lipoproteins. The prevalence of total cholesterol >240 mg/dl is 37% in diabetic men and 44% in diabetic women and the prevalence for LDL-C>160 mg/dl are 31% and 44%, respectively in these populations. Diabetes is a disease in which a patient's ability to control glucose levels in blood is decreased because of partial impairment in the response to insulin. Type II diabetes (T2D), also called non-insulin dependent diabetes mellitus (NIDDM), accounts for 80-90% of all diabetes cases in developed countries. In T2D, the pancreatic Islets of Langerhans produce insulin but the primary target tissues (muscle, liver and adipose tissue) develop a profound resistance to its effects. The body compensates by producing more insulin ultimately resulting in failure of pancreatic insulin-producing capacity. Thus T2D is a cardiovascular-metabolic syndrome associated with multiple comorbidities including dyslipidemia and insulin resistance, as well as hypertension, endothelial dysfunction and inflammatory atherosderosis.

The first line treatment for dyslipidemia and diabetes is a low-fat and low-glucose diet, exercise and weight loss. Compliance can be moderate and treatment of the various metabolic deficiencies that develop becomes necessary with, for example, lipid-modulating agents such as statins and fibrates, hypoglycemic drugs such as sulfonylureas and metformin, or insulin sensitizers of the thiazolidinedione (TZD) class of PPARgamma-agonists. Recent studies provide evidence that modulators of FXR may have enhanced therapeutic potential by providing superior normalization of both LDL-C and triglyceride levels, currently achieved only with combinations of existing drugs and, in addition, may avoid feedback effects on cellular cholesterol homeostasis.

SUMMARY OF THE INVENTION

The present invention is concerned with novel benzimidazole derivatives, their manufacture and their use as medicaments. In particular, the invention relates to compounds of formula (I):

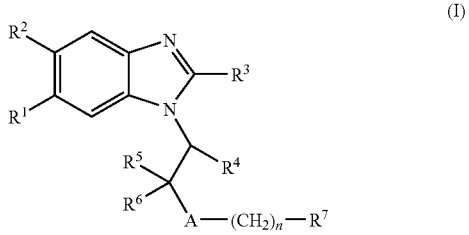

and pharmaceutically acceptable salts and esters thereof wherein A, $R^1$-$R^7$, and n are as defined in the detailed description and claims.

The novel compounds of the present invention exceed the compounds known in the art, inasmuch as they bind to and selectively modulate FXR very efficiently. Consequently, cholesterol absorption is reduced, LDL cholesterol and triglycerides are lowered, and inflammatory atherosclerosis is reduced. Since multiple facets of combined dyslipidemia and cholesterol homeostasis are addressed by FXR modulators, they are expected to have an enhanced therapeutic potential compared to the compounds already known in the art.

DETAILED DESCRIPTION OF THE INVENTION

Unless otherwise indicated, the following definitions are set forth to illustrate and define the meaning and scope of the various terms used to describe the invention herein.

In the present description the term "alkyl", alone or in combination, signifies a straight-chain or branched-chain alkyl group with 1 to 8 carbon atoms. In preferred embodiments, the alkyl has 1 to 6 carbon atoms and in particularly preferred embodiments has 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and more preferably methyl.

The term "cycloalkyl", alone or in combination, signifies a cycloalkyl ring with 3 to 8 carbon atoms. In preferred embodiments the cycloalkyl has 3 to 6 carbon atoms. Examples of C3-C8 cycloalkyls are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. Preferred cycloalkyls are cyclopropyl, cyclobutyl, cyclopentyl, cyclohexyl and cycloheptyl. Cyclopropyl and cyclohexyl are particularly preferred.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy and most preferred methoxy.

The term "hydrogen" or "hydro" refers to the moiety of a hydrogen atom (—H) and not $H_2$.

The term "halogen", alone or in combination, signifies fluoro, chloro, bromo or iodo. In certain preferred embodiments the halogen is fluoro or chloro.

The term "cycloalkoxy", alone or in combination, signifies a group of the formula cycloalkyl-O— in which the term "cycloalkyl" has the previously given significance, such as cyclopropyloxy, cyclobutyloxy, cyclopentyloxy and cyclohexyloxy. A preferred example of cycloalkoxy is cyclopropyloxy.

The term "haloalkyl", alone or in combination, signifies an alkyl group as defined above wherein one or more hydrogen atoms are replaced with a halogen atom. In particular embodiments, the haloalkyl preferably has one, two or three halogen atoms. A preferred example of a haloalkyl is trifluoromethyl.

The term "aryl", alone or in combination, signifies a phenyl group which optionally carries one or more substituents. In preferred embodiments, the aryl is a phenyl group which is optionally substituted by one, two or three substituents independently selected from halogen, trifluoromethyl, alkyl, alkoxy, carboxy, alkoxycarbonyl, cycloalkoxycarbonyl and the like, preferably fluorine, chlorine, carboxy, carboxymethoxy, carboxyethoxy, carboxycyclopropyloxy, methyl, methoxy and trifluoromethyl.

The term "heterocyclyl", alone or in combination signifies a saturated, partially unsaturated or aromatic 5- to 10-membered heterocycle which contains one or more hetero atoms selected from nitrogen, oxygen and sulphur. Examples include furyl, pyridinyl, 2-oxo-1,2-dihydro-pyridinyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzoimidazolyl, indolyl, isoindolyl, 1,3-dioxo-isoindolyl, quinolinyl, indazolyl, benzoisothiazolyl, benzoxazolyl and benzoisoxazolyl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, azetidin-2-one-1-yl, pyrrolidin-2-one-1-yl, piperid-2-one-1-yl, azepan-2-one-1-yl, 3-azabicyco[3.1.0]hexanyl, 3-azabicyclo[4.1.0]heptanyl, oxetanyl, azabicyclo[2.2.2]hexanyl, 3H-indolyl and quinolizinyl, isoxazol-3-one-5-yl, 1H-tetrazole-5-yl, [1,2,4]oxadiazolidine-3,5-dione-2-yl, thiazolidine-2,4-dione-5-yl and imidazolidine-2,4-dione-5-yl. Spiro moieties are also included in the scope of this definition. A heterocyclyl group may have a substitution pattern as described earlier in connection with the term "aryl". Preferred heterocyclyl groups are pyridinyl, pyrimidinyl, 1H-tetrazole-5-yl and thieno[3,2-c]pyridinyl.

The term "carboxy", alone or in combination, signifies the group —COOH.

The term "oxy", alone or in combination, signifies the —O— group.

Compounds of formula (I) can form pharmaceutically acceptable addition salts. Examples of such pharmaceutically acceptable salts are salts of compounds of formula (I) with physiologically compatible mineral bases, such as alkaline, earth-alkaline and ammonium salts such as e.g., Na—, K—, Ca— and trimethylammonium salts. The term "pharmaceutically acceptable salts" refers to such salts.

The term "pharmaceutically acceptable esters" embraces derivatives of the compounds of formula (I), in which a carboxy group has been converted to an ester. Alkyl, hydroxyalkyl, alkoxy-alkyl, amino-alkyl, mono- or di-alkyl-aminoalkyl, morpholino-alkyl, pyrrolidino-alkyl, piperidino-alkyl, piperazino-alkyl, alkyl-piperazino-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preferred are the compounds of formula (I). Further preferred are the pharmaceutically acceptable salts of the compounds of formula (I). Further preferred are the pharmaceutically acceptable esters of the compounds of formula (I).

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, in reference to a particular group or molecule, the term "substituted" refers to the fact that at least one of the hydrogen atoms of that group or molecule is replaced by some other substituent.

Unless otherwise indicated, the term "a compound of the formula" or "a compound of formula" or "compounds of the formula" or "compounds of formula" refers to any compound selected from the genus of compounds as defined by the formula.

In detail, the present invention relates to compounds of formula (I):

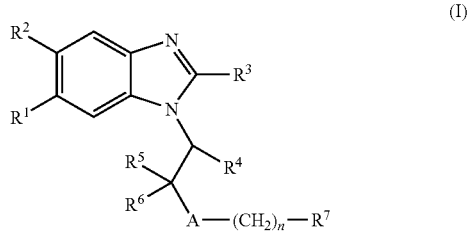

(I)

or pharmaceutically acceptable salts or esters thereof, wherein:
  A is oxygen, sulfur, $SO_2$, $CH_2$ or $NR^8$;
  $R^1$ is hydrogen or halogen;
  $R^2$ is hydrogen or halogen;
  $R^3$ is phenyl or pyridinyl, wherein said phenyl or pyridinyl is optionally substituted with one to three substituents independently selected from the group consisting of alkyl, haloalkyl, alkoxy and halogen;
  $R^4$ is alkyl, cycloalkyl, halocycloalkyl or phenyl;
  $R^5$ and $R^6$ are independently hydrogen or alkyl; or alternatively $R^5$ and $R^6$ together with the carbon atom to which they are attached form cycloalkyl;
  $R^7$ is cycloalkyl, phenyl, pyridinyl, pyrimidinyl, or thieno[2,3-c]pyridinyl; which is optionally substituted with one to three substituents independently selected from the group consisting of: (1) alkyl, (2) haloalkyl, (3) alkoxy, (4) carboxy, (5) carboxyalkoxy, (6) carboxycycloalkoxy, (7) halogen, (8) isoxazol-3-one-5-yl, (9) 1H-tetrazol-5-yl, (10) [1,2,4]oxadiazolidin-3,5-dione-2-yl, (11) thiazolidin-2,4-dione-5-yl, and (12) imidazolidin-2,4-dione-5-yl;
  $R^8$ is hydrogen, alkyl or haloalkyl; and
  n is 0 or 1.

Preferred are the compounds of formula (I) wherein A is oxygen or $NR^8$. $R^8$ is preferably hydrogen or alkyl, more preferably hydrogen or methyl, and in particular hydrogen.

Preferred are the compounds of formula (I) wherein A is oxygen or $NR^8$ wherein $R^8$ is hydrogen or methyl. Further preferred are the compounds of formula (I) wherein A is oxygen or $NR^8$ wherein $R^8$ is hydrogen. The compounds of formula (I) wherein A is oxygen are also particularly preferred.

Furthermore, the compounds of formula (I) wherein $R^1$ is hydrogen or fluorine are preferred.

The compounds of formula (I) wherein $R^2$ is hydrogen or fluorine are also preferred.

Particularly preferred are the compounds of formula (I) wherein $R^1$ and $R^2$ are both hydrogen or both fluorine at the same time.

The compounds of formula (I), wherein $R^3$ is phenyl, substituted phenyl, pyridinyl or substituted pyridinyl, wherein substituted phenyl and substituted pyridinyl are phenyl and pyridinyl substituted with one to three substituents independently selected from alkyl, haloalkyl, alkoxy and halogen are preferred.

The compounds of formula (I) wherein $R^3$ is substituted phenyl, pyridinyl or substituted pyridinyl, wherein substituted phenyl is phenyl substituted with one or two substituents selected from alkyl and halogen and substituted pyridinyl is pyridinyl substituted with two alkoxy.

In the definition of $R^3$, halogen is preferably chloro and alkoxy is preferably methoxy.

Particularly preferred are the compounds of formula (I) wherein $R^3$ is phenyl substituted with halogen or pyridinyl substituted with two alkoxy.

Further preferred are the compounds of formula (I) wherein $R^3$ is phenyl, chlorophenyl or dimethoxypyridinyl, preferably chlorophenyl or dimethoxypyridinyl.

The compounds of formula (I) wherein $R^3$ is chlorophenyl are particularly preferred. The compounds of formula (I), wherein $R^3$ is dimethoxypyridinyl are also particularly preferred.

Furthermore, the compounds of formula (I) wherein $R^4$ is alkyl, cycloalkyl or phenyl are preferred and the compounds of formula (I), wherein $R^4$ is tert-butyl, iso-butyl, cyclohexyl or phenyl are particularly preferred. Particularly preferred are the compounds of formula (I), wherein $R^4$ is cyclohexyl.

Also preferred are the compounds of formula (I) wherein $R^4$ is cycloalkyl or halocycloalkyl.

Further preferred are the compounds of formula (I) wherein $R^4$ is cyclopropyl, cyclopentyl, cyclohexyl, halocyclohexyl or cycloheptyl.

Moreover, preferred are the compounds of formula (I) wherein $R^4$ is cyclohexyl or difluorocyclohexyl.

Further preferred are the compounds of formula (I) wherein $R^5$ is hydrogen or methyl.

In particular, the compounds of formula (I) wherein $R^5$ and $R^6$ are both hydrogen or both methyl at the same time are preferred.

Furthermore, preferred are the compounds of formula (I) wherein $R^5$ and $R^6$ are both hydrogen at the same time.

Preferred are the compounds of formula (I) wherein $R^7$ is cyclohexyl, substituted cyclohexyl, phenyl, substituted phenyl, pyridinyl, substituted pyridinyl, pyrimidinyl, substituted pyrimidinyl, thieno[2,3-c]pyridinyl or substituted thieno[2,3-c]pyridinyl, wherein substituted cyclohexyl, substituted phenyl, substituted pyridinyl, substituted pyrimidinyl, and substituted thieno[2,3-c]pyridinyl are cyclohexyl, phenyl, pyridinyl, pyrimidinyl and thieno[2,3-c]pyridinyl substituted with one to three substituents independently selected from alkyl, haloalkyl, alkoxy, carboxy, carboxyalkoxy, carboxycycloalkoxy, halogen, isoxazol-3-one-5-yl, 1H-tetrazol-5-yl, [1,2,4]oxadiazolidin-3,5-dione-2-yl, thiazolidin-2,4-dione-5-yl and imidazolidin-2,4-dione-5-yl.

The compounds of formula (I) wherein $R^7$ is cyclohexyl, substituted cyclohexyl, phenyl, substituted phenyl, pyridinyl, substituted pyridinyl, pyrimidinyl, substituted pyrimidinyl, thieno[2,3-c]pyridinyl or substituted thieno[2,3-c]pyridinyl, wherein substituted cyclohexyl, substituted phenyl, substituted pyridinyl, substituted pyrimidinyl, and substituted thieno[2,3-c]pyridinyl are substituted with one to three substituents independently selected from methyl, trifluoromethyl, methoxy, carboxy, carboxymethoxy, carboxyethoxy, carboxylsopropyloxy, carboxycyclopropyloxy, 1H-tetrazol-5-yl, chlorine and fluorine are further preferred.

The compounds of formula (I), wherein $R^7$ is cyclohexyl, substituted cyclohexyl, phenyl, substituted phenyl, pyridinyl, substituted pyridinyl, pyrimidinyl, substituted pyrimidinyl, thieno[2,3-c]pyridinyl or substituted thieno[2,3-c]pyridinyl, wherein substituted cyclohexyl, substituted phenyl, substituted pyridinyl, substituted pyrimidinyl, and substituted thieno[2,3-c]pyridinyl are substituted with one to three substituents independently selected from alkyl, haloalkyl, alkoxy, carboxy, carboxyalkoxy, carboxycycloalkoxy, halogen and heterocyclyl are preferred.

The compounds of formula (I), wherein $R^7$ is cyclohexyl, substituted cyclohexyl, phenyl, substituted phenyl, pyridinyl, substituted pyridinyl, pyrimidinyl, substituted pyrimidinyl, thieno[2,3-c]pyridinyl or substituted thieno[2,3-c]pyridinyl, wherein substituted cyclohexyl, substituted phenyl, substituted pyridinyl, substituted pyrimidinyl, and substituted thieno[2,3-c]pyridinyl are substituted with one to three substituents independently selected from methyl, trifluoromethyl, methoxy, carboxy, carboxymethoxy, carboxyethoxy, carboxylsopropyloxy, carboxycyclopropyloxy, 1H-tetrazol-5-yl, chlorine and fluorine are further preferred.

The preferred heterocyclyl substituents, in the definition of $R^7$, are selected from isoxazol-3-one-5-yl, 1H-tetrazol-5-yl, [1,2,4]oxadiazolidin-3,5-dione-2-yl, thiazolidin-2,4-dione-5-yl and imidazolidin-2,4-dione-5-yl.

The compounds of formula (I) wherein $R^7$ is substituted cyclohexyl, substituted phenyl or substituted pyridinyl wherein substituted cyclohexyl, substituted phenyl and substituted pyridinyl are substituted with one to three substituents independently selected from alkyl, haloalkyl, carboxy, carboxycycloalkoxy, halogen and 1H-tetrazol-5-yl are also preferred.

Further preferred are the compounds of formula (I) wherein $R^7$ is substituted cyclohexyl, substituted phenyl or substituted pyridinyl wherein substituted cyclohexyl, substituted phenyl and substituted pyridinyl are substituted with one to three substituents independently selected from methyl, trifluoromethyl, carboxy, carboxycyclopropyloxy, chloro, fluoro and 1H-tetrazol-5-yl.

Further preferred are compounds of formula (I) wherein $R^8$ is hydrogen.

Furthermore, preferred are the compounds of formula (I), wherein n is zero.

Particularly preferred are the compounds of formula (I) selected from
2-(4-Chloro-phenyl)-1-(1-cyclohexyl-2-cyclohexyl-methoxy-ethyl)-5,6-difluoro-1H-benzoimidazole;
(−)-2-(4-Chloro-phenyl)-1-(1-cyclohexyl-2-cyclohexyl-methoxy-ethyl)-5,6-difluoro-1H-benzoimidazole;
(+)-2-(4-Chloro-phenyl)-1-(1-cyclohexyl-2-cyclohexyl-methoxy-ethyl)-5,6-difluoro-1H-benzoimidazole;
4-{2-[2-(4-Chloro-phenyl)-5,6-difluoro-benzoimidazol-1-yl]-2-cyclohexyl-ethoxy}-benzoic acid;
(+)-4-{2-[2-(4-Chloro-phenyl)-5,6-difluoro-benzoimidazol-yl]-2-cyclohexyl-ethoxy}-benzoic acid;
(−)-4-{2-[2-(4-Chloro-phenyl)-5,6-difluoro-benzoimidazol-1-yl]-2-cyclohexyl-ethoxy}-benzoic acid;
4-{2-[2-(4-Chloro-phenyl)-5,6-difluoro-benzoimidazol-1-yl]-2-cyclohexyl-ethoxy}-3-fluoro-benzoic acid;
(−)-4-{2-[2-(4-Chloro-phenyl)-5,6-difluoro-benzoimidazol-1-yl]-2-cyclohexyl-ethoxy}-3-fluoro-benzoic acid;
(+)-4-{2-[2-(4-Chloro-phenyl)-5,6-difluoro-benzoimidazol-1-yl]-2-cyclohexyl-ethoxy}-3-fluoro-benzoic acid;
3-Chloro-4-{2-[2-(4-chloro-phenyl)-5,6-difluoro-benzoimidazol-1-yl]-2-cyclohexyl-ethoxy}-benzoic acid;
4-{2-[2-(4-Chloro-phenyl)-5,6-difluoro-benzoimidazol-1-yl]-2-cyclohexyl-ethoxy}-3-methyl-benzoic acid;
(−)-4-{2-[2-(4-Chloro-phenyl)-5,6-difluoro-benzoimidazol-1-yl]-2-cyclohexyl-ethoxy}-3-methyl-benzoic acid;
(+)-4-{2-[2-(4-Chloro-phenyl)-5,6-difluoro-benzoimidazol-1-yl]-2-cyclohexyl-ethoxy}-3-methyl-benzoic acid;
2-{2-[2-(4-Chloro-phenyl)-5,6-difluoro-benzoimidazol-1-yl]-2-cyclohexyl-ethoxy}-benzoic acid;
3-{2-[2-(4-Chloro-phenyl)-5,6-difluoro-benzoimidazol-1-yl]-2-cyclohexyl-ethoxy}-benzoic acid;
3-{2-[2-(4-Chloro-phenyl)-5,6-difluoro-benzoimidazol-1-yl]-2-cyclohexyl-ethoxy}-4-methyl-benzoic acid;
3-{2-[2-(4-Chloro-phenyl)-5,6-difluoro-benzoimidazol-1-yl]-2-cyclohexyl-ethoxy}-2-methyl-benzoic acid;
5-{2-[2-(4-Chloro-phenyl)-5,6-difluoro-benzoimidazol-1-yl]-2-cyclohexyl-ethoxy}-pyridine-2-carboxylic acid;
6-{2-[2-(4-Chloro-phenyl)-5,6-difluoro-benzoimidazol-1-yl]-2-cyclohexyl-ethoxy}-nicotinic acid;
(+)-6-{2-[2-(4-Chloro-phenyl)-5,6-difluoro-benzoimidazol-1-yl]-2-cyclohexyl-ethoxy}-nicotinic acid;
(−)-6-{2-[2-(4-Chloro-phenyl)-5,6-difluoro-benzoimidazol-1-yl]-2-cyclohexyl-ethoxy}-nicotinic acid;
5-Chloro-6-{2-[2-(4-chloro-phenyl)-5,6-difluoro-benzoimidazol-1-yl]-2-cyclohexyl-ethoxy}-nicotinic acid;
(+)-5-Chloro-6-{2-[2-(4-chloro-phenyl)-5,6-difluoro-benzoimidazol-1-yl]-2-cyclohexyl-ethoxy}-nicotinic acid;
(−)-5-Chloro-6-{2-[2-(4-chloro-phenyl)-5,6-difluoro-benzoimidazol-1-yl]-2-cyclohexyl-ethoxy}-nicotinic acid;
5-{2-[2-(4-Chloro-phenyl)-5,6-difluoro-benzoimidazol-1-yl]-2-cyclohexyl-ethoxy}-4-methyl-pyrimidine-2-carboxylic acid;
4-{2-[2-(4-Chloro-phenyl)-5,6-difluoro-benzoimidazol-1-yl]-2-cyclohexyl-ethoxy}-thieno[3,2-c]pyridine-7-carboxylic acid;
(+)-4-{2-[2-(4-Chloro-phenyl)-5,6-difluoro-benzoimidazol-1-yl]-2-cyclohexyl-ethoxy}-thieno[3,2-c]pyridine-7-carboxylic acid;
(−)-4-{2-[2-(4-Chloro-phenyl)-5,6-difluoro-benzoimidazol-1-yl]-2-cyclohexyl-ethoxy}-thieno[3,2-c]pyridine-7-carboxylic acid;
2-(4-Chloro-phenyl)-1-[1-cyclohexyl-2-(pyridin-2-yloxy)-ethyl]-5,6-difluoro-1H-benzoimidazole;
6-{2-[2-(4-Chloro-phenyl)-5,6-difluoro-benzoimidazol-1-yl]-2-cyclohexyl-ethoxy}-pyridine-2-carboxylic acid;
2-{2-[2-(4-Chloro-phenyl)-5,6-difluoro-benzoimidazol-1-yl]-2-cyclohexyl-ethoxy}-6-methoxy-isonicotinic acid;
4-{2-[2-(4-Chloro-phenyl)-benzoimidazol-1-yl]-2-cyclohexyl-ethoxy}-benzoic acid;
4-{2-[2-(4-Chloro-phenyl)-benzoimidazol-1-yl]-2-cyclohexyl-ethoxy}-3-fluoro-benzoic acid;
2-(4-Chloro-phenyl)-1-[1-cyclohexyl-2-(2-fluoro-phenoxy)-ethyl]-5,6-difluoro-1H-benzoimidazole;
2-(4-Chloro-phenyl)-1-[1-cyclohexyl-2-(pyridin-3-yloxy)-ethyl]-5,6-difluoro-1H-benzoimidazole;
2-(4-Chloro-phenyl)-1-[1-cyclohexyl-2-(pyridin-4-yloxy)-ethyl]-5,6-difluoro-1H-benzoimidazole;
2-{2-[2-(4-Chloro-phenyl)-5,6-difluoro-benzoimidazol-1-yl]-2-cyclohexyl-ethoxy}-isonicotinic acid;
2-(4-Chloro-phenyl)-1-(1-cyclohexyl-2-phenoxy-ethyl)-5,6-difluoro-1H-benzoimidazole;

4-{2-[2-(4-Chloro-phenyl)-5,6-difluoro-benzoimidazol-1-yl]-2-cyclohexyl-ethoxy}-3-trifluoromethyl-benzoic acid;
(+)-4-{2-[2-(4-Chloro-phenyl)-5,6-difluoro-benzoimidazol-1-yl]-2-cyclohexyl-ethoxy}-3-trifluoromethyl-benzoic acid;
(−)-4-{2-[2-(4-Chloro-phenyl)-5,6-difluoro-benzoimidazol-1-yl]-2-cyclohexyl-ethoxy}-3-trifluoromethyl-benzoic acid;
4-{2-[2-(4-Chloro-phenyl)-5,6-difluoro-benzoimidazol-1-yl]-2-cyclohexyl-ethoxy}-2,6-difluoro-benzoic acid;
(+)-4-{2-[2-(4-Chloro-phenyl)-5,6-difluoro-benzoimidazol-1-yl]-2-cyclohexyl-ethoxy}-2,6-difluoro-benzoic acid;
(−)-4-{2-[2-(4-Chloro-phenyl)-5,6-difluoro-benzoimidazol-1-yl]-2-cyclohexyl-ethoxy}-2,6-difluoro-benzoic acid;
(6-{2-[2-(4-Chloro-phenyl)-5,6-difluoro-benzoimidazol-1-yl]-2-cyclohexyl-ethoxy}-pyridin-3-yloxy)-acetic acid;
4-{2-Cyclohexyl-2-[2-(2,6-dimethoxy-pyridin-3-yl)-5,6-difluoro-benzoimidazol-1-yl]-ethoxy}-3-fluoro-benzoic acid;
2-(6-{2-[2-(4-Chloro-phenyl)-5,6-difluoro-benzoimidazol-1-yl]-2-cyclohexyl-ethoxy}-pyridin-3-yloxy)-2-methyl-propionic acid;
(+)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid;
(−)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid;
1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;
(−)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;
(+)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;
4-{2-[2-(4-Chloro-phenyl)-5,6-difluoro-benzoimidazol-1-yl]-2-cyclohexyl-ethoxy}-3,5-dimethyl-benzoic acid;
(+)-4-{2-[2-(4-Chloro-phenyl)-5,6-difluoro-benzoimidazol-1-yl]-2-cyclohexyl-ethoxy}-3,5-dimethyl-benzoic acid;
(−)-4-{2-[2-(4-Chloro-phenyl)-5,6-difluoro-benzoimidazol-1-yl]-2-cyclohexyl-ethoxy}-3,5-dimethyl-benzoic acid;
2-(4-Chloro-phenyl)-1-{1-cyclohexyl-2-[5-(1H-tetrazol-5-yl)-pyridin-2-yloxy]-ethyl}-5,6-difluoro-1H-benzoimidazole;
4-{2-[2-(4-Chloro-phenyl)-5,6-difluoro-benzoimidazol-1-yl]-2-cyclohexyl-1,1-dimethyl-ethoxymethyl}-benzoic acid;
4-{2-[2-(4-Chloro-phenyl)-5,6-difluoro-benzoimidazol-1-yl]-2-cyclohexyl-ethoxymethyl}-benzoic acid;
4-{2-[2-(4-Chloro-phenyl)-5,6-difluoro-benzoimidazol-1-yl]-2-cyclohexyl-ethoxymethyl}-3-fluoro-benzoic acid; and
4-{2-[2-(4-Chloro-phenyl)-5,6-difluoro-benzoimidazol-1-yl]-2-cyclohexyl-ethoxymethyl}-3-methoxy-benzoic acid.

Also preferred are the compounds of formula (I) selected from
4-{2-[2-(4-Chloro-phenyl)-5,6-difluoro-benzoimidazol-1-yl]-2-cyclohexyl-ethoxy}-cyclohexanecarboxylic acid;
4-{2-Cyclohexyl-2-[2-(2,6-dimethoxy-pyridin-3-yl)-5,6-difluoro-benzoimidazol-1-yl]-ethoxy}-benzoic acid;
4-{2-Cyclohexyl-2-[2-(2,6-dimethoxy-pyridin-3-yl)-5,6-difluoro-benzoimidazol-1-yl]-ethoxy}-3-trifluoromethyl-benzoic acid;
2-(6-{2-Cyclohexyl-2-[2-(2,6-dimethoxy-pyridin-3-yl)-5,6-difluoro-benzoimidazol-1-yl]-ethoxy}-pyridin-3-yloxy)-2-methyl-propionic acid;
1-(6-{2-Cyclohexyl-2-[2-(2,6-dimethoxy-pyridin-3-yl)-5,6-difluoro-benzoimidazol-1-yl]-ethoxy}-pyridin-3-yloxy)-cyclopropanecarboxylic;
4-{2-[2-(4-Chloro-phenyl)-5,6-difluoro-benzoimidazol-1-yl]-2-cyclohexyl-1,1-dimethyl-ethoxy}-benzoic acid;
4-{2-[2-(4-Chloro-phenyl)-5,6-difluoro-benzoimidazol-1-yl]-2-cyclohexyl-1,1-dimethyl-ethoxy}-3-fluoro-benzoic acid;
6-{2-[2-(4-Chloro-phenyl)-5,6-difluoro-benzoimidazol-1-yl]-2-cyclohexyl-1,1-dimethyl-ethoxy}-nicotinic acid;
4-{2-[2-(4-Chloro-phenyl)-5,6-difluoro-benzoimidazol-1-yl]-2-cyclohexyl-ethoxy}-3,5-difluoro-benzoic acid;
6-{2-[2-(4-Chloro-phenyl)-5,6-difluoro-benzoimidazol-1-yl]-2-cyclohexyl-ethoxymethyl}-nicotinic acid;
(4-{2-[2-(4-Chloro-phenyl)-5,6-difluoro-benzoimidazol-1-yl]-2-cyclohexyl-ethoxy}-phenoxy)-acetic acid;
2-(4-{2-[2-(4-Chloro-phenyl)-5,6-difluoro-benzoimidazol-1-yl]-2-cyclohexyl-ethoxy}-phenoxy)-propionic acid;
2-(4-{2-[2-(4-Chloro-phenyl)-5,6-difluoro-benzoimidazol-yl]-2-cyclohexyl-ethoxy}-phenoxy)-2-methyl-propionic acid;
4-{2-[2-(4-Chloro-phenyl)-5,6-difluoro-benzoimidazol-1-yl]-2-cyclohexyl-ethylamino}-benzoic acid;
4-({2-[2-(4-Chloro-phenyl)-5,6-difluoro-benzoimidazol-1-yl]-2-cyclohexyl-ethyl}-methyl-amino)-benzoic acid;
4-[{2-[2-(4-Chloro-phenyl)-5,6-difluoro-benzoimidazol-1-yl]-2-cyclohexyl-ethyl}-(2,2,2-trifluoro-ethyl)-amino]-benzoic acid;
4-{2-[2-(4-Chloro-phenyl)-5,6-difluoro-benzoimidazol-1-yl]-2-cyclohexyl-ethylsulfanyl}-benzoic acid;
4-{2-[2-(4-Chloro-phenyl)-5,6-difluoro-benzoimidazol-1-yl]-2-cyclohexyl-ethanesulfonyl}-benzoic acid;
4-{3-[2-(4-Chloro-phenyl)-5,6-difluoro-benzoimidazol-1-yl]-3-cyclohexyl-propyl}-benzoic acid;
and their stereoisomers.

Also preferred are the compounds of formula (I) selected from
4-{2-[2-(4-Chloro-phenyl)-5,6-difluoro-benzoimidazol-1-yl]-2-cyclohexyl-ethoxy}-2,6-dimethyl-benzoic acid;
(+)-2-(4-Chloro-phenyl)-1-{1-cyclohexyl-2-[5-(1H-tetrazol-5-yl)-pyridin-2-yloxy]-ethyl}-5,6-difluoro-1H-benzoimidazole;
(−)-2-(4-Chloro-phenyl)-1-{1-cyclohexyl-2-[5-(1H-tetrazol-5-yl)-pyridin-2-yloxy]-ethyl}-5,6-difluoro-1H-benzoimidazole;
(+)-4-{2-[2-(4-Chloro-phenyl)-5,6-difluoro-benzoimidazol-1-yl]-2-cyclohexyl-ethoxymethyl}-3-fluoro-benzoic acid;
(−)-4-{2-[2-(4-Chloro-phenyl)-5,6-difluoro-benzoimidazol-1-yl]-2-cyclohexyl-ethoxymethyl}-3-fluoro-benzoic acid;
2-(4-Chloro-phenyl)-1-{1-cyclohexyl-2-[2-fluoro-4-(1H-tetrazol-5-yl)-phenoxy]-ethyl}-5,6-difluoro-1H-benzoimidazole;
6-{2-[2-(4-Chloro-phenyl)-5,6-difluoro-benzoimidazol-1-yl]-2-cyclohexyl-ethoxymethyl}-nicotinic acid;
(−)-4-{2-[2-(4-Chloro-phenyl)-5,6-difluoro-benzoimidazol-1-yl]-2-cyclohexyl-ethoxymethyl}-benzoic acid;
(+)-4-{2-[2-(4-Chloro-phenyl)-5,6-difluoro-benzoimidazol-1-yl]-2-cyclohexyl-ethoxymethyl}-benzoic acid;
2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;
(−)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;

(+)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;
6-{2-Cyclohexyl-2-[2-(2,6-dimethoxy-pyridin-3-yl)-5,6-difluoro-benzoimidazol-1-yl]-ethoxy}-nicotinic acid;
(+)-6-{2-Cyclohexyl-2-[2-(2,6-dimethoxy-pyridin-3-yl)-5,6-difluoro-benzoimidazol-1-yl]-ethoxy}-nicotinic acid;
(−)-6-{2-Cyclohexyl-2-[2-(2,6-dimethoxy-pyridin-3-yl)-5,6-difluoro-benzoimidazol-1-yl]-ethoxy}-nicotinic acid;
3-Chloro-4-{2-[2-(4-chloro-phenyl)-5,6-difluoro-benzoimidazol-1-yl]-2-cyclohexyl-ethoxy}-5-fluoro-benzoic acid;
(−)-3-Chloro-4-{2-[2-(4-chloro-phenyl)-5,6-difluoro-benzoimidazol-1-yl]-2-cyclohexyl-ethoxy}-5-fluoro-benzoic acid;
(+)-3-Chloro-4-{(S)-2-[2-(4-chloro-phenyl)-5,6-difluoro-benzoimidazol-1-yl]-2-cyclohexyl-ethoxy}-5-fluoro-benzoic acid;
4-(1-{2-[2-(4-Chloro-phenyl)-5,6-difluoro-benzoimidazol-1-yl]-2-cyclohexyl-ethoxy}-ethyl)-benzoic acid;
2-(4-Chloro-phenyl)-1-{1-cyclohexyl-2-[2-fluoro-4-(1H-tetrazol-5-yl)-phenoxy]-ethyl}-5,6-difluoro-1H-benzoimidazole;
(+)-2-(4-Chloro-phenyl)-1-{1-cyclohexyl-2-[2-fluoro-4-(1H-tetrazol-5-yl)-phenoxy]-ethyl}-5,6-difluoro-1H-benzoimidazole;
(−)-2-(4-Chloro-phenyl)-1-{(S)-1-cyclohexyl-2-[2-fluoro-4-(1H-tetrazol-5-yl)-phenoxy]-ethyl}-5,6-difluoro-1H-benzoimidazole;
4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
(+)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
(−)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
4-{2-[2-(4-Chloro-phenyl)-5,6-difluoro-benzoimidazol-1-yl]-2-cyclohexyl-ethoxy}-3,5-difluoro-benzoic acid;
(−)-4-{2-[2-(4-Chloro-phenyl)-5,6-difluoro-benzoimidazol-1-yl]-2-cyclohexyl-ethoxy}-3,5-difluoro-benzoic acid;
(−)-4-{2-[2-(4-Chloro-phenyl)-5,6-difluoro-benzoimidazol-1-yl]-2-cyclohexyl-ethoxy}-3,5-difluoro-benzoic acid;
(+)-2-(4-Chloro-phenyl)-1-{1-cyclohexyl-2-methyl-2-[4-(1H-tetrazol-5-yl)-phenoxy]-propyl}-5,6-difluoro-1H-benzoimidazole;
(−)-2-(4-Chloro-phenyl)-1-{1-cyclohexyl-2-methyl-2-[4-(1H-tetrazol-5-yl)-phenoxy]-propyl}-5,6-difluoro-1H-benzoimidazole;
(+)-4-{2-[2-(4-Chloro-phenyl)-5,6-difluoro-benzoimidazol-1-yl]-2-cyclohexyl-1,1-dimethyl-ethoxy}-benzoic acid;
(−)-4-{2-[2-(4-Chloro-phenyl)-5,6-difluoro-benzoimidazol-1-yl]-2-cyclohexyl-1,1-dimethyl-ethoxy}-benzoic acid;
2-(4-{2-[2-(4-Chloro-phenyl)-5,6-difluoro-benzoimidazol-1-yl]-2-cyclohexyl-ethoxy}-phenoxy)-2-methyl-propionic acid;
(4-{2-[2-(4-Chloro-phenyl)-5,6-difluoro-benzoimidazol-1-yl]-2-cyclohexyl-ethoxy}-phenoxy)-acetic acid;
(4-{2-[2-(4-Chloro-phenyl)-5,6-difluoro-benzoimidazol-1-yl]-2-cyclohexyl-ethoxy}-2-methyl-phenoxy)-acetic acid;
2-(4-{2-[2-(4-Chloro-phenyl)-5,6-difluoro-benzoimidazol-1-yl]-2-cyclohexyl-ethoxy}-2,3-dimethyl-phenoxy)-2-methyl-propionic acid;
2-(4-{2-[2-(4-Chloro-phenyl)-5,6-difluoro-benzoimidazol-1-yl]-2-cyclohexyl-ethoxy}-3-fluoro-phenoxy)-2-methyl-propionic acid;
2-(3-{2-[2-(4-Chloro-phenyl)-5,6-difluoro-benzoimidazol-1-yl]-2-cyclohexyl-ethoxy}-phenoxy)-2-methyl-propionic acid;
4-{2-Cyclohexyl-2-[2-(2,6-dimethoxy-pyridin-3-yl)-5,6-difluoro-benzoimidazol-1-yl]-ethoxy}-3,5-difluoro-benzoic acid;
(+)-4-{2-Cyclohexyl-2-[2-(2,6-dimethoxy-pyridin-3-yl)-5,6-difluoro-benzoimidazol-1-yl]-ethoxy}-3,5-difluoro-benzoic acid;
(−)-4-{2-Cyclohexyl-2-[2-(2,6-dimethoxy-pyridin-3-yl)-5,6-difluoro-benzoimidazol-1-yl]-ethoxy}-3,5-difluoro-benzoic acid;
1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
(+)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
(−)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
4-{2-[2-(4-Chloro-phenyl)-benzoimidazol-1-yl]-2-cyclohexyl-ethoxy}-3,5-difluoro-benzoic acid;
(+)-4-{2-[2-(4-Chloro-phenyl)-benzoimidazol-1-yl]-2-cyclohexyl-ethoxy}-3,5-difluoro-benzoic acid;
(−)-4-{2-[2-(4-Chloro-phenyl)-benzoimidazol-1-yl]-2-cyclohexyl-ethoxy}-3,5-difluoro-benzoic acid;
4-{2-[2-(4-Chloro-phenyl)-benzoimidazol-1-yl]-2-cyclohexyl-ethoxy}-3,5-dimethyl-benzoic acid;
(−)-4-{2-[2-(4-Chloro-phenyl)-benzoimidazol-1-yl]-2-cyclohexyl-ethoxy}-3,5-dimethyl-benzoic acid;
(+)-4-{2-[2-(4-Chloro-phenyl)-benzoimidazol-1-yl]-2-cyclohexyl-ethoxy}-3,5-dimethyl-benzoic acid;
3-Chloro-4-{2-[2-(4-chloro-phenyl)-benzoimidazol-1-yl]-2-cyclohexyl-ethoxy}-5-fluoro-benzoic acid;
(−)-3-Chloro-4-{2-[2-(4-chloro-phenyl)-benzoimidazol-1-yl]-2-cyclohexyl-ethoxy}-5-fluoro-benzoic acid;
(+)-3-Chloro-4-{2-[2-(4-chloro-phenyl)-benzoimidazol-1-yl]-2-cyclohexyl-ethoxy}-5-fluoro-benzoic acid;
2-(4-Chloro-phenyl)-1-{1-cyclohexyl-2-[2,6-dimethyl-4-(1H-tetrazol-5-yl)-phenoxy]-ethyl}-1H-benzoimidazole;
(−)-2-(4-Chloro-phenyl)-1-{1-cyclohexyl-2-[2,6-dimethyl-4-(1H-tetrazol-5-yl)-phenoxy]-ethyl}-1H-benzoimidazole;
(+)-2-(4-Chloro-phenyl)-1-{1-cyclohexyl-2-[2,6-dimethyl-4-(1H-tetrazol-5-yl)-phenoxy]-ethyl}-1H-benzoimidazole;
5-Bromo-6-{2-[2-(4-chloro-phenyl)-5,6-difluoro-benzoimidazol-1-yl]-2-cyclohexyl-ethoxy}-nicotinic acid;
(+)-2-(4-Chloro-phenyl)-1-{1-cyclohexyl-2-[2,6-difluoro-4-(1H-tetrazol-5-yl)-phenoxy]-2-methyl-propyl}-5,6-difluoro-1H-benzoimidazole;
(−)-2-(4-Chloro-phenyl)-1-{1-cyclohexyl-2-[2,6-difluoro-4-(1H-tetrazol-5-yl)-phenoxy]-2-methyl-propyl}-5,6-difluoro-1H-benzoimidazole;
(+)-4-{2-[2-(4-Chloro-phenyl)-5,6-difluoro-benzoimidazol-1-yl]-2-cyclohexyl-1,1-dimethyl-ethoxy}-3,5-difluoro-benzoic acid;
(−)-4-{2-[2-(4-Chloro-phenyl)-5,6-difluoro-benzoimidazol-1-yl]-2-cyclohexyl-1,1-dimethyl-ethoxy}-3,5-difluoro-benzoic acid;
1-(4-{2-[2-(4-Chloro-phenyl)-5,6-difluoro-benzoimidazol-1-yl]-2-cyclohexyl-ethoxy}-phenoxy)-cyclobutanecarboxylic acid;
(+)-1-(4-{2-[2-(4-Chloro-phenyl)-5,6-difluoro-benzoimidazol-1-yl]-2-cyclohexyl-ethoxy}-phenoxy)-cyclobutanecarboxylic acid;
(−)-1-(4-{2-[2-(4-Chloro-phenyl)-5,6-difluoro-benzoimidazol-1-yl]-2-cyclohexyl-ethoxy}-phenoxy)-cyclobutanecarboxylic acid;
1-(4-{2-[2-(4-Chloro-phenyl)-5,6-difluoro-benzoimidazol-1-yl]-2-cyclohexyl-ethoxy}-phenoxy)-cyclopropanecarboxylic acid;

(−)-1-(4-{2-[2-(4-Chloro-phenyl)-5,6-difluoro-benzoimidazol-1-yl]-2-cyclohexyl-ethoxy}-phenoxy)-cyclopropanecarboxylic acid;
(+)-1-(4-{2-[2-(4-Chloro-phenyl)-5,6-difluoro-benzoimidazol-1-yl]-2-cyclohexyl-ethoxy}-phenoxy)-cyclopropanecarboxylic acid;
6-{2-[2-(4-Chloro-2-methyl-phenyl)-5,6-difluoro-benzoimidazol-1-yl]-2-cyclohexyl-ethoxy}-nicotinic acid;
4-{2-[2-(4-Chloro-2-methyl-phenyl)-5,6-difluoro-benzoimidazol-1-yl]-2-cyclohexyl-ethoxy}-3,5-difluoro-benzoic acid;
(−)-4-{2-[2-(4-Chloro-2-methyl-phenyl)-5,6-difluoro-benzoimidazol-1-yl]-2-cyclohexyl-ethoxy}-3,5-difluoro-benzoic acid;
(+)-4-{2-[2-(4-Chloro-2-methyl-phenyl)-5,6-difluoro-benzoimidazol-1-yl]-2-cyclohexyl-ethoxy}-3,5-difluoro-benzoic acid;
2-(4-Chloro-phenyl)-1-{1-cyclohexyl-2-[2,6-difluoro-4-(1H-tetrazol-5-yl)-phenoxy]-ethyl}-5,6-difluoro-1H-benzimidazole;
2-(4-Chloro-phenyl)-1-{1-cyclohexyl-2-[2,6-difluoro-4-(1H-tetrazol-5-yl)-phenoxy]-ethyl}-1H-benzoimidazole;
1-{1-Cyclohexyl-2-[2,6-difluoro-4-(1H-tetrazol-5-yl)-phenoxy]-ethyl}-2-(2,6-dimethoxy-pyridin-3-yl)-5,6-difluoro-1H-benzoimidazole;
6-{2-[2-(4-Chloro-phenyl)-5,6-difluoro-benzoimidazol-1-yl]-2-cycloheptyl-ethoxy}-nicotinic acid;
4-{2-[2-(4-Chloro-phenyl)-5,6-difluoro-benzoimidazol-1-yl]-2-cycloheptyl-ethoxy}-3,5-difluoro-benzoic acid;
(−)-4-{2-[2-(4-Chloro-phenyl)-5,6-difluoro-benzoimidazol-1-yl]-2-cycloheptyl-ethoxy}-3,5-difluoro-benzoic acid;
(+)-4-{2-[2-(4-Chloro-phenyl)-5,6-difluoro-benzoimidazol-1-yl]-2-cycloheptyl-ethoxy}-3,5-difluoro-benzoic acid;
2-(4-Chloro-phenyl)-1-{1-(4,4-difluoro-cyclohexyl)-2-[2,6-dimethyl-4-(1H-tetrazol-5-yl)-phenoxy]-ethyl}-5,6-difluoro-1H-benzoimidazole;
2-(4-Chloro-phenyl)-1-{1-cyclopentyl-2-[2,6-dimethyl-4-(1H-tetrazol-5-yl)-phenoxy]-ethyl}-5,6-difluoro-1H-benzoimidazole;
2-(4-Chloro-phenyl)-1-{1-cyclopropyl-2-[2,6-dimethyl-4-(1H-tetrazol-5-yl)-phenoxy]-ethyl}-5,6-difluoro-1H-benzoimidazole;
(+)-4-{2-[2-(4-Chloro-phenyl)-5,6-difluoro-benzoimidazol-1-yl]-(2-cis-cyclohexyl-ethylamino)}-cyclohexanecarboxylic acid;
(−)-4-{2-[2-(4-Chloro-phenyl)-5,6-difluoro-benzoimidazol-1-yl]-(2-cis-cyclohexyl-ethylamino)}-cyclohexanecarboxylic acid;
(+)-4-{2-[2-(4-Chloro-phenyl)-5,6-difluoro-benzoimidazol-1-yl]-(2-trans-cyclohexyl-ethylamino)}-cyclohexanecarboxylic acid;
(−)-4-{2-[2-(4-Chloro-phenyl)-5,6-difluoro-benzoimidazol-1-yl]-(2-trans-cyclohexyl-ethylamino)}-cyclohexanecarboxylic acid;
{2-[2-(4-Chloro-phenyl)-5,6-difluoro-benzoimidazol-1-yl]-2-cyclohexyl-ethyl}-[4-(1H-tetrazol-5-yl)-phenyl]-amine;
4-{2-[2-(4-Chloro-phenyl)-5,6-difluoro-benzoimidazol-1-yl]-2-cyclohexyl-ethylsulfanyl}-benzoic acid;
4-{2-[2-(4-Chloro-phenyl)-5,6-difluoro-benzoimidazol-1-yl]-2-cyclohexyl-ethanesulfonyl}-benzoic acid;
4-[3-Cyclohexyl-3-(5,6-difluoro-2-phenyl-benzoimidazol-1-yl)-propyl]-benzoic acid;
(−)-4-[3-Cyclohexyl-3-(5,6-difluoro-2-phenyl-benzoimidazol-1-yl)-propyl]-benzoic acid;
(+)-4-[3-Cyclohexyl-3-(5,6-difluoro-2-phenyl-benzoimidazol-1-yl)-propyl]-benzoic acid;
4-{3-Cyclohexyl-3-[2-(2,6-dimethoxy-pyridin-3-yl)-5,6-difluoro-benzoimidazol-1-yl]-propyl}-benzoic acid;
(−)-4-{3-Cyclohexyl-3-[2-(2,6-dimethoxy-pyridin-3-yl)-5,6-difluoro-benzoimidazol-1-yl]-propyl}-benzoic acid; and
(+)-4-{3-Cyclohexyl-3-[2-(2,6-dimethoxy-pyridin-3-yl)-5,6-difluoro-benzoimidazol-1-yl]-propyl}-benzoic acid.

Also particularly preferred are the compounds of formula (I) selected from
(+)-4-{2-[2-(4-Chloro-phenyl)-5,6-difluoro-benzoimidazol-1-yl]-2-cyclohexyl-ethoxy}-3,5-dimethyl-benzoic acid;
(+)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;
(−)-3-Chloro-4-{2-[2-(4-chloro-phenyl)-5,6-difluoro-benzoimidazol-1-yl]-2-cyclohexyl-ethoxy}-5-fluoro-benzoic acid;
(−)-2-(4-Chloro-phenyl)-1-{(S)-1-cyclohexyl-2-[2-fluoro-4-(1H-tetrazol-5-yl)-phenoxy]-ethyl}-5,6-difluoro-1H-benzoimidazole;
(+)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
(−)-4-{2-[2-(4-Chloro-phenyl)-5,6-difluoro-benzoimidazol-1-yl]-2-cyclohexyl-ethoxy}-3,5-difluoro-benzoic acid;
(−)-4-{2-Cyclohexyl-2-[2-(2,6-dimethoxy-pyridin-3-yl)-5,6-difluoro-benzoimidazol-1-yl]-ethoxy}-3,5-difluoro-benzoic acid;
(−)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
(−)-3-Chloro-4-{2-[2-(4-chloro-phenyl)-benzoimidazol-1-yl]-2-cyclohexyl-ethoxy}-5-fluoro-benzoic acid;
(+)-2-(4-Chloro-phenyl)-1-{1-cyclohexyl-2-[2,6-dimethyl-4-(1H-tetrazol-5-yl)-phenoxy]-ethyl}-1H-benzoimidazole;
2-(4-Chloro-phenyl)-1-{1-cyclohexyl-2-[2,6-difluoro-4-(1H-tetrazol-5-yl)-phenoxy]-ethyl}-5,6-difluoro-1H-benzimidazole;
2-(4-Chloro-phenyl)-1-{1-(4,4-difluoro-cyclohexyl)-2-[2,6-dimethyl-4-(1H-tetrazol-5-yl)-phenoxy]-ethyl}-5,6-difluoro-1H-benzoimidazole;
(+)-4-{2-[2-(4-Chloro-phenyl)-5,6-difluoro-benzoimidazol-1-yl]-(2-trans-cyclohexyl-ethylamino)}-cyclohexanecarboxylic acid;
(−)-4-{2-[2-(4-Chloro-phenyl)-5,6-difluoro-benzoimidazol-1-yl]-(2-trans-cyclohexyl-ethylamino)}-cyclohexanecarboxylic acid;
{2-[2-(4-Chloro-phenyl)-5,6-difluoro-benzoimidazol-1-yl]-2-cyclohexyl-ethyl}-[4-(1H-tetrazol-5-yl)-phenyl]-amine;
(−)-4-[3-Cyclohexyl-3-(5,6-difluoro-2-phenyl-benzoimidazol-1-yl)-propyl]-benzoic acid; and
(+)-4-{3-Cyclohexyl-3-[2-(2,6-dimethoxy-pyridin-3-yl)-5,6-difluoro-benzoimidazol-1-yl]-propyl}-benzoic acid.

In particular, preferred are the compounds of formula (Ia):

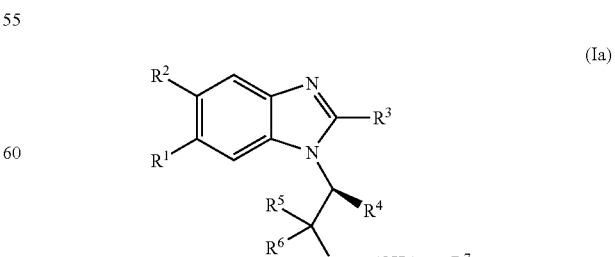

(Ia)

wherein A, $R^1$, $R^2$, $R^3$, $R^4$, $R^5$, $R^6$, $R^7$ and n are as defined above.

Further preferred are the compounds of formula (Ib):

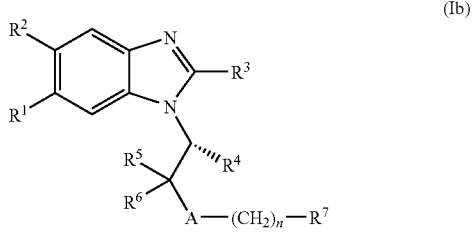

wherein A, $R^1$, $R^2$, $R^3$, $R^4$, $R^5$, $R^6$, $R^7$ and n are as defined above.
(S)-[2-(4-Chloro-phenyl)-5,6-difluoro-benzoimidazol-1-yl]-cyclohexyl-acetic acid methyl ester, (R)-[2-(4-Chloro-phenyl)-5,6-difluoro-benzoimidazol-1-yl]-cyclohexyl-acetic acid methyl ester, (S)-[2-(4-Chloro-phenyl)-5,6-difluoro-benzoimidazol-1-yl]-cyclohexyl-acetic acid and (R)-[2-(4-Chloro-phenyl)-5,6-difluoro-benzoimidazol-1-yl]-cyclohexyl-acetic acid are particularly useful synthetic intermediates.

The compounds of formula (I) have one or more asymmetric C atoms and can therefore exist as an enantiomeric mixture, diastereomeric mixture or as optically pure compounds.

Insofar as their preparation is not described in the examples, the compounds of formula (I) as well as all intermediate products can be prepared according to analogous methods or according to the methods set forth above. Starting materials are commercially available, are known in the art, or can be prepared by methods analogous to those described herein. Unless otherwise indicated, the substituents A, $R^1$ to $R^8$ and n are as described above.

A typical procedure for the preparation of compounds of formula (I) is illustrated in the following Scheme 1.

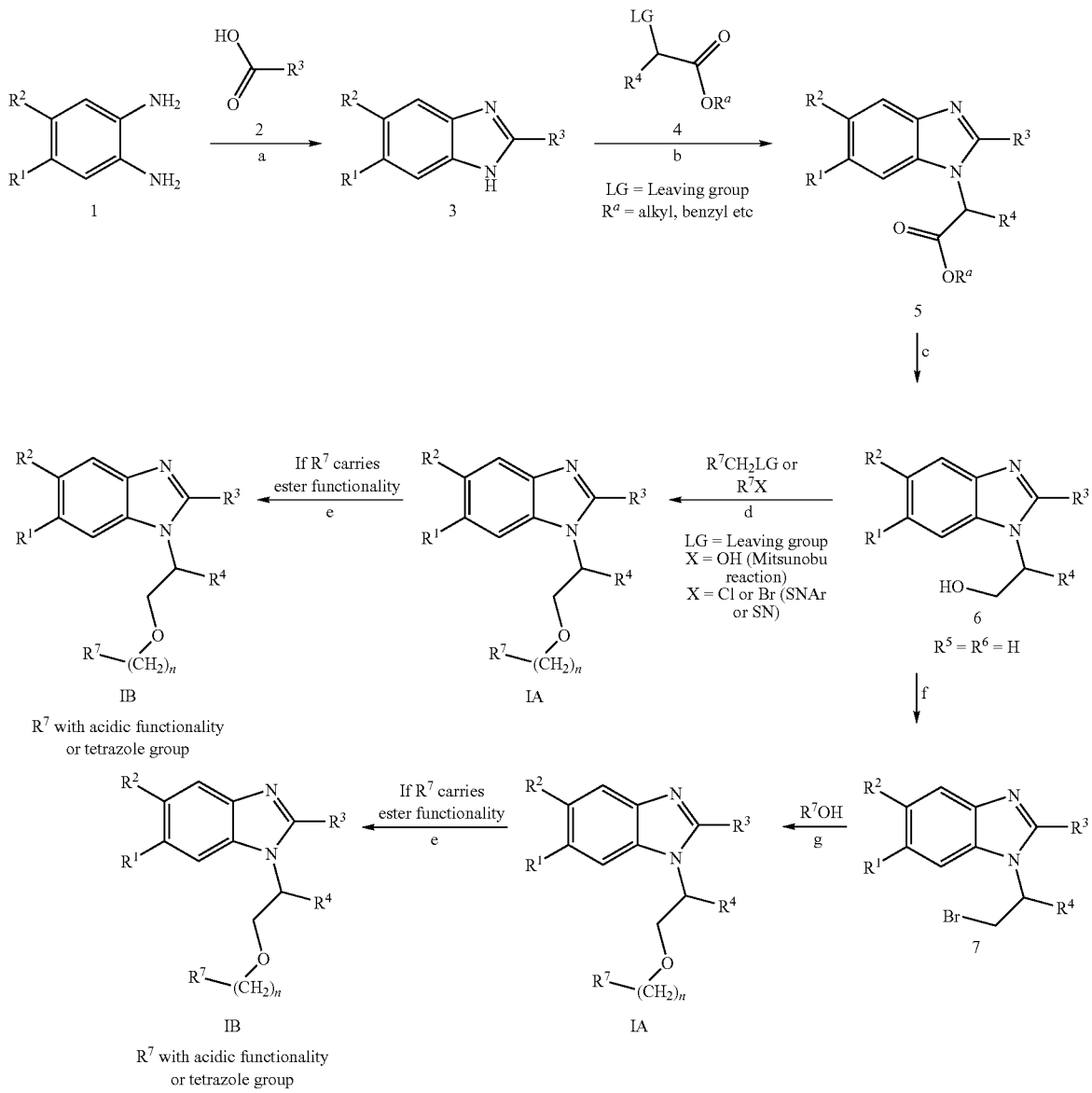

Benzimidazoles of the general structure 3 (either commercially available or accessible via, e.g. reaction of an appropriately substituted phenylene diamine 1 with an aryl-carboxylic acid 2 (step a) can be alkylated with, e.g. a 2-bromo (or another leaving group such as, e.g. $OSO_2$alkyl, $OSO_2$fluoroalkyl, $OSO_2$aryl)-alkylacetic acid ester 4 in an appropriate solvent such as, e.g. N,N'-dimethylformamide and a suitable base such as, e.g. cesium carbonate to give intermediates 5 (step b, $R^a$ signifies a benzyl or an alkyl group such as, e.g. methyl, ethyl or tert-butyl). Reduction of the ester functionality using, e.g. lithium aluminum hydride, yields the alcohol intermediate 6 (step c). Formation of the ether bond to give compounds of formula IA can be accomplished by, e.g. Mitsunobu couplings of intermediate 6 (step d) with optionally substituted phenols or hydroxy-substituted heterocycles (either commercially available or accessible by methods described in references or by methods known in the art). Mitsunobu reactions of this type are widely used and described in literature (e.g. "March's Advanced Organic Chemistry" by M. B. Smith and J. March, $7^{th}$ ed., 2007, Wiley & Sons N.Y.; Hughes, D. L. et al., Org. Prep. Proceed. Int. 1996, 28(2), 127-64; But, T. Y. S., Chemistry—An Asian Journal (2007), 2(11), 1340-1355). Alternatively, compounds of the formula IA can be obtained by either nucleophilic substitution with alkyl-, cycloalkyl-, cycloalkylmethyl- or aryl/heteroarylalkyl-halides or by nucleophilic aromatic substitution, for example by reacting an activated chloro or bromo heterocycle with intermediate 6 using an appropriate base such as, e.g. sodium hydride in a suitable solvent such as, e.g. N,N-dimethylformamide (step d). Reactions of this type are known to those skilled in the art and are widely used and described in literature (e.g. "March's Advanced Organic Chemistry" by M. B. Smith and J. March, $7^{th}$ ed., 2007, Wiley & Sons N.Y.; Vlasov, V. M., Russian Chem Rev 2003, 72(8), 681-703; Zoltewicz, J. A., Top. Curr. Chem. 1975, 59, 33).

Compounds of the formula IA can be also obtained by converting the alcohol group in intermediates 6 to a leaving group such as e.g. bromide (or other leaving group such as, e.g. —$OSO_2$alkyl, —$OSO_2$fluoroalkyl, —$OSO_2$aryl) to give intermediates 7 (step f) and reacting these with alcohols using an appropriate base such as, e.g. sodium hydride in a suitable solvent such as, e.g. N,N-dimethylformamide (step g).

In those cases where the substituent $R^7$ in compounds of formula IA carries an ester functionality, the ester functionality can be cleaved under basic (e.g. methyl or ethyl esters with lithium or sodium hydroxide in polar solvents such as, e.g. methanol, water or tetrahydrofuran or mixtures of said solvents) or under acidic conditions (e.g. tert-butyl ester using concentrated hydrochloric acid in tetrahydrofuran or formic acid in an appropriate solvent such as alcohols like, e.g. isopropanol) to furnish final compounds IB (step e). Further esters include, but are not limited to, e.g. allyl or benzyl esters that can be cleaved by methods known to those skilled in the art and as described for example in "Protective Groups in Organic Chemistry" by T. W. Greene and P. G. M. Wutts, $2^{nd}$ Ed., 1991, Wiley N.Y.). Optionally, the substituent $R^7$ in compounds IA can carry cyano groups that can be hydrolyzed to the carboxylic acid under basic (e.g. with aqueous sodium or lithium hydroxide) or acidic conditions (e.g. hydrochloric or sulphuric acid), or can be converted into the corresponding tetrazole group, to furnish compounds IB (step e). Preparation of Tetrazoles from Cyano Groups is Widely Described in Literature and can be accomplished by using standard procedures such as, e.g. by treatment with sodium azide in the presence of a Lewis acid in water or organic solvents like dichloromethane at temperatures between 0° C. and the boiling point of the solvent.

Optionally, compounds of formula (I) can contain cyano groups which can be converted to the corresponding tetrazoles using standard procedures such as, e.g. by treatment with sodium azide in the presence of a Lewis acid in water or organic solvents like dichloromethane at temperatures between 0° C. and the boiling point of the solvent.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

Intermediates 6 can be also obtained by reduction of the acid intermediate 8, using a reducing agent such as, e.g. lithium aluminum hydride in an appropriate solvent such as, e.g. tetrahydrofuran according to Scheme 2. The acid intermediate 8 can be prepared for example via ester cleavage of the ester intermediates 5 applying the conditions described under Scheme 1.

Scheme 2

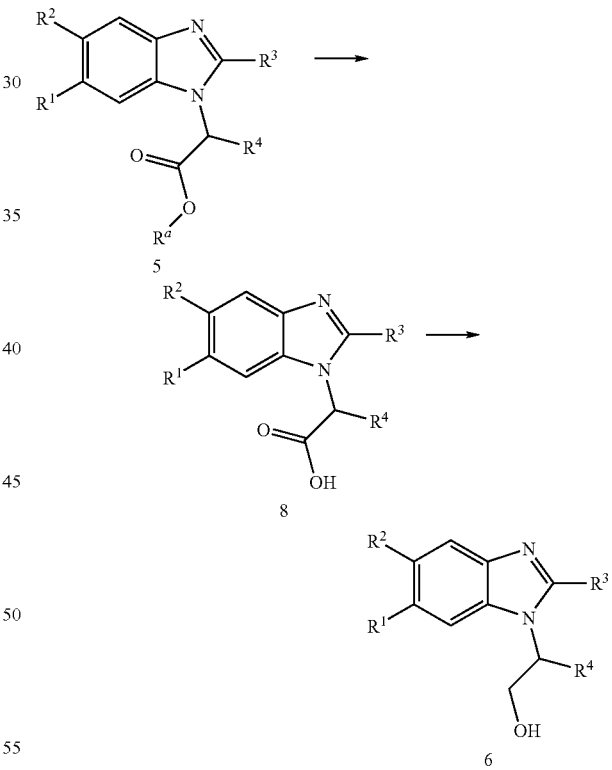

Intermediates of type 8 can also be prepared as described in Scheme 3. In this approach a mono Boc-protected ortho arylene diamine 9, a carboxylic acid 2, an isonitrile 10, and an aldehyde 11 are condensed in an organic solvent such as e.g. methanol in the presence of an acid (such as e.g. hydrochloric acid) to the bis-amide 12 in an Ugi-type condensation (step a). Bis-amide 12 is deprotected with an appropriate acid such as, e.g. trifluoroacetic acid and cyclised to the desired benzimidazole 13 (step b). Typical procedures applicable to this approach are described e.g. by Tempest et al. in Tet. Lett.

2001, 42, 4959-4962 and 4963-4968, or by Zhang et al. in Tet. Lett. 2004, 45, 6757-6760. Mono boc-protected ortho arylene diamines 9 are commercially available or may be prepared from the corresponding unprotected diamine by treatment with di-tert-butyl dicarbonate in an organic solvent such as e.g. tetrahydrofuran in the presence of a base such as, e.g. diisopropylethylamine.

Alternatively, intermediates of type 13 can be prepared according to Scheme 4. In a suitable organic solvent such as, e.g. methanol, a 2-azidoarylamine 14, a carboxylic acid 2, an isonitrile 10 and an aldehyde 11 are condensed to 15 again in a so called Ugi-type reaction (step a, typical procedures may be found, e.g. in "The Peptides" by Gross & Meienhofer vol. 2, Academic Press, N.Y., 1980, pp 365-381). In a subsequent intramolecular Staudinger-type reaction with a suitable reagent such as, e.g. triphenylphosphine, the azido bis-amide 15 is converted to the benzimidazole 13.

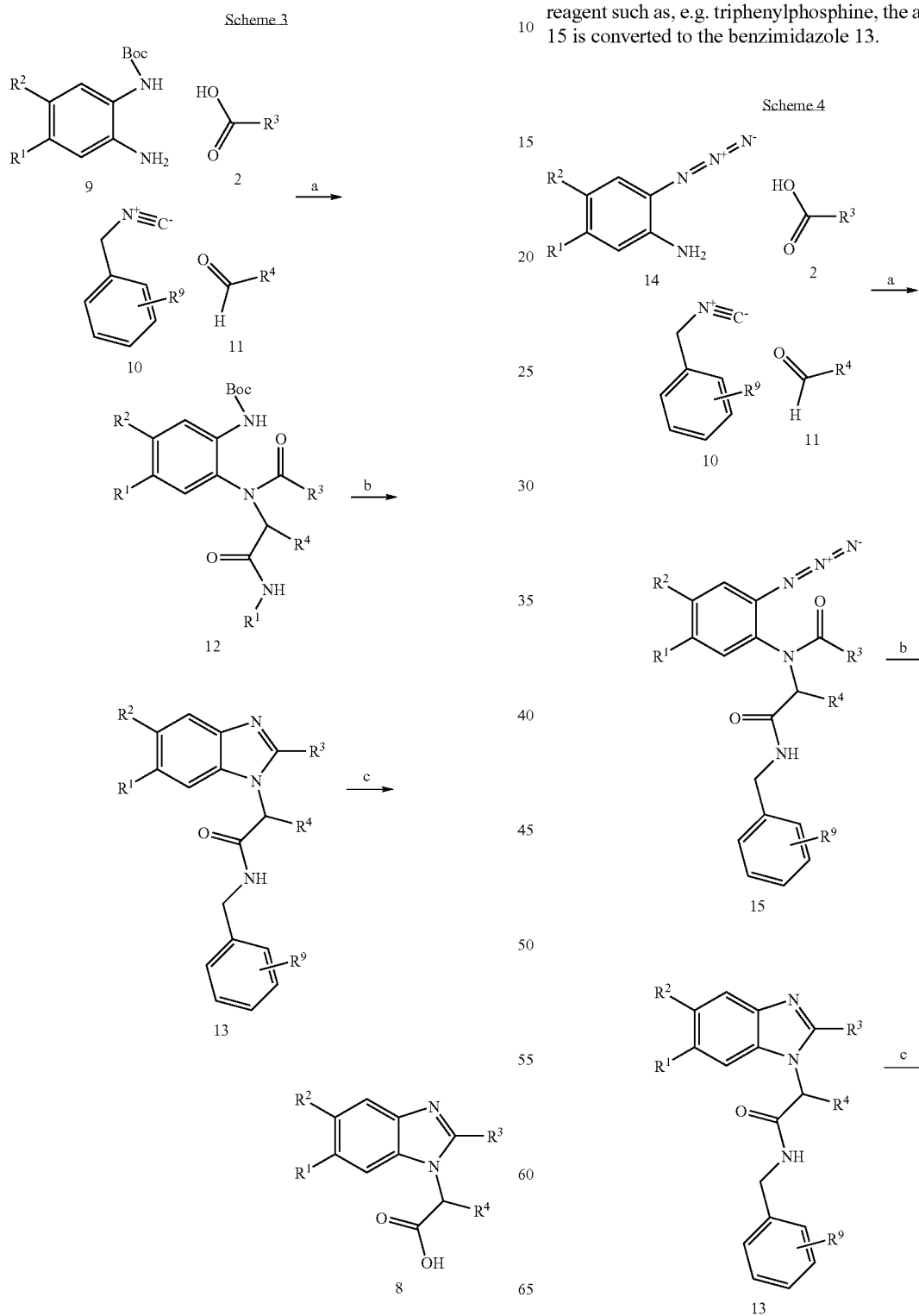

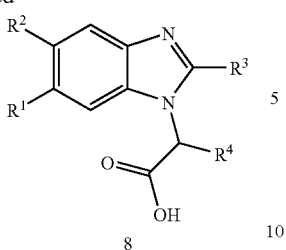

Compounds of general structure IA and IB in which n equals 1 and $R^5$ and $R^6$ equal a methyl group can be prepared according to Scheme 5 from intermediates of type 16 which in turn are accessible via reaction of intermediate 5 with, e.g. alkyl-magnesium halides such as, e.g. methylmagnesium bromide in an appropriate solvent such as, e.g. diethyl ether (step a). Alkylation of intermediates 16 can be accomplished according to the methods outline above (step b). Optionally, the substituent $R^7$ in compounds IA can carry an ester or a cyano group that can be converted into the corresponding carboxylic acid and tetrazole group applying the conditions described above, to furnish compounds IB (step c).

Scheme 5

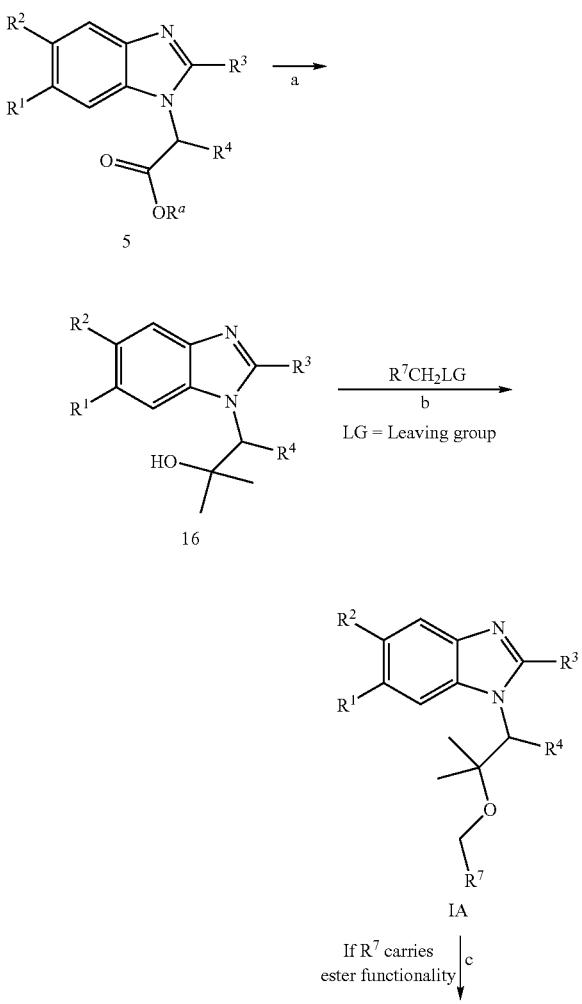

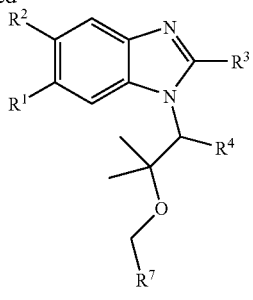

IB $R^7$ with acidic functionality or tetrazole group

Compounds of general structure IC to IF in which n equals 0 and A equals S or $SO_2$ can be prepared according to Scheme 6 from intermediates of type 17 which can be prepared as described above (intermediate 7: LG=Br) or in the case of LG signifies a —$OSO_2$alkyl, —$OSO_2$fluoroalkyl or —$OSO_2$aryl group by treatment of intermediate 6 with, e.g. an alkyl-, fluoroalkyl- or arylsulfonic acid chloride or -anhydride in a suitable solvent such as, e.g. dichloromethane and using an appropriate base such as, e.g. Hünig's base or pyridine (step a). Reaction of intermediates 17 with, e.g. optionally substituted alkyl- or aryl-thiols with a suitable base such as, e.g. sodium hydride in an appropriate solvent such as, e.g. N,N-dimethylformamide furnishes compounds IC (step b). Compounds IC can be converted into compounds ID through oxidation of the sulfur atom with an oxidizing agent such as, e.g. 3-chloroperoxybenzoic acid in a suitable solvent such as, e.g. dichloromethane (step c). In case compounds IC and ID carry a carboxylic ester group these can be can be cleaved by methods known to those skilled in the art and as described for example in "Protective Groups in Organic Chemistry" by T. W. Greene and P. G. M. Wutts, 2nd Ed., 1991, Wiley N.Y.) to yield the corresponding carboxylic acids. For example, a benzyl ester can be cleaved by catalytic hydrogenation using an appropriate catalyst such as, e.g. palladium on charcoal in a suitable solvent such as, e.g. methanol, ethanol, ethyl acetate, tetrahydrofuran or mixtures of said solvents. An alkyl ester such as, e.g. a methyl or ethyl ester can be cleaved under basic conditions (e.g. with lithium or sodium hydroxide in polar solvents such as, e.g. methanol, water or tetrahydrofuran or mixtures of said solvents). A tert-butyl ester can be cleaved for example under acidic conditions (e.g. using trifluoroacetic acid, optionally in an appropriate solvent such as, e.g. dichloromethane and optionally using a nucleophilic scavenger such as, e.g. 1,3-dimethoxybenzene or thioanisole, or using concentrated hydrochloric acid in tetrahydrofuran or formic acid in an appropriate solvent such as an alcohol like, e.g. isopropanol). An allyl ester can be cleaved for example in a transition metal-catalyzed reaction using, e.g. tetrakis(triphenylphenyl)palladium as catalyst together with pyrrolidine or morpholine in tetrahydrofuran as solvent.

Optionally, compounds IC and ID can also contain cyano groups which can be either hydrolyzed to the carboxylic acid under basic (e.g. with aqueous sodium or lithium hydroxide) or acidic conditions (e.g. hydrochloric or sulphuric acid) or can be converted to the corresponding tetrazoles using standard procedures such as, e.g. by treatment with sodium azide in the presence of a Lewis acid or ammonium chloride in water or organic solvents like dichloromethane or N,N-dimethylformamide at temperatures between 0° C. and the boiling point of the solvent to furnish compounds IE and IF (step d).

Alternatively, compounds of the formula IF can be synthesized by oxidation of compounds IE (step c) applying the methods described above.

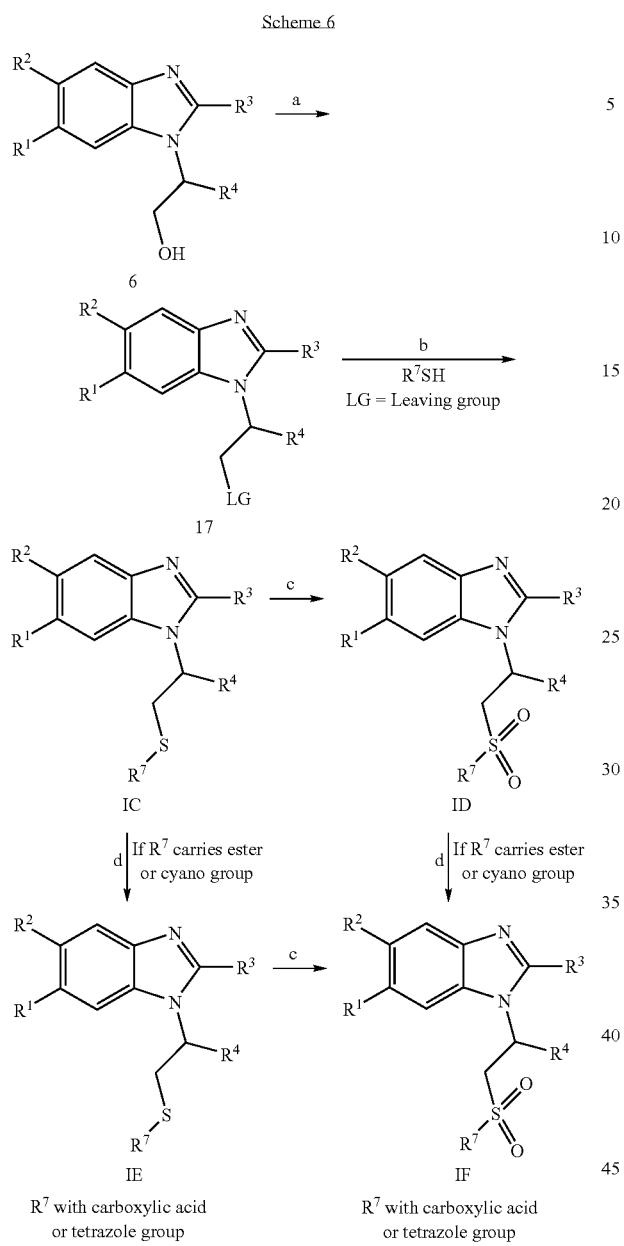

Scheme 6

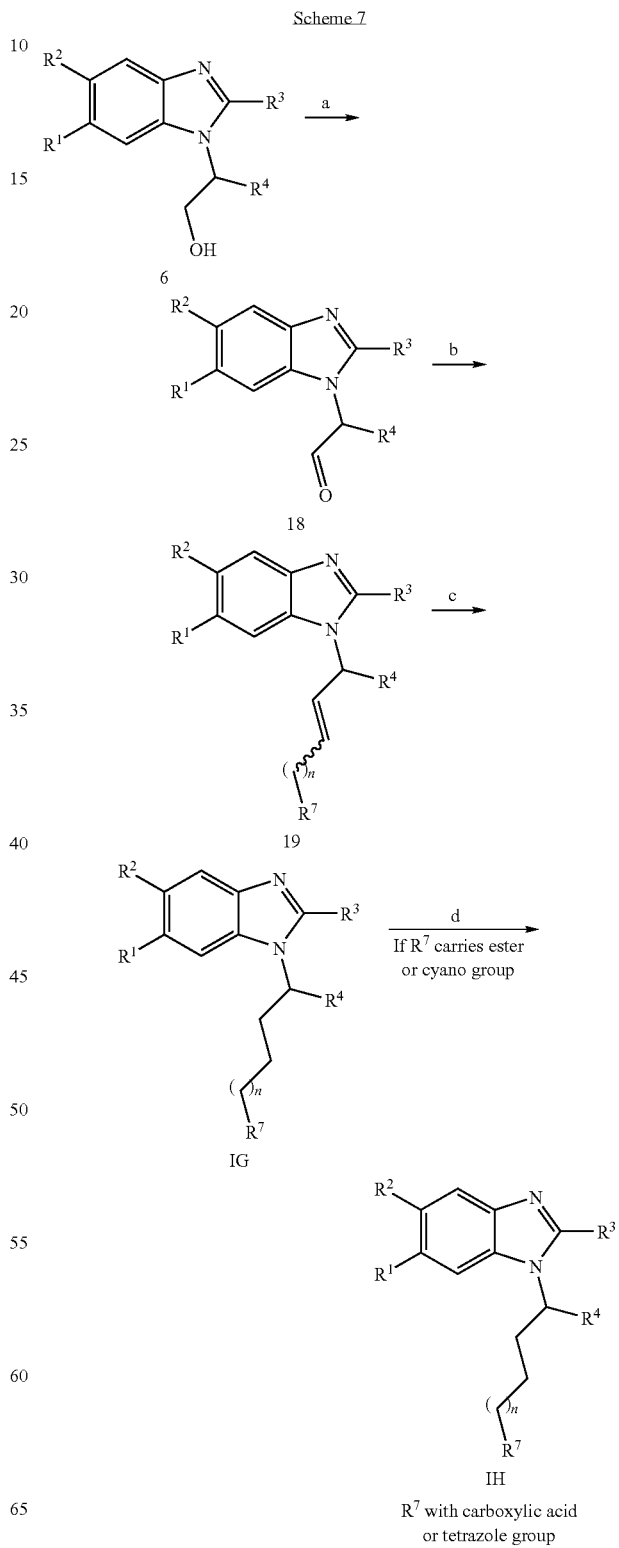

Scheme 7 compounds IG by, e.g. catalytic hydrogenation using a transition metal catalyst such as, e.g. palladium or palladium on charcoal in an appropriate solvent such as, e.g. ethyl acetate, methanol or ethanol or mixtures of said solvents (step c).

Optionally compounds IG can contain ester or cyano groups that can be converted into the corresponding carboxylic acid and tetrazole groups, respectively, applying the conditions described before, to furnish compounds IH (step d).

Compounds of general structure IG and IH in which n equals 0 and A equals $CH_2$ can be prepared according to Scheme 7. Intermediates 18 can be synthesized by oxidation of intermediates 6 (step a). Reactions of this type are known to those skilled in the art and are widely used and described in literature (e.g. "March's Advanced Organic Chemistry" by M. B. Smith and J. March, 7$^{th}$ ed., 2007, Wiley & Sons N.Y.). For example, intermediate 6 can be oxidized with, e.g. 1,1,1-triacetoxy-1,1-dihydro-1,2-benziodoxol-3(1H)-one in an appropriate solvent such as, e.g. dichloromethane or chloroform. Intermediates 19 are accessible by, e.g. Wittig reaction which is well known to those skilled in the art. For example, intermediate 18 is reacted with an optionally substituted benzyl-triphenyl-phosphonium chloride or bromide (either commercially available or synthesized by methods known in the art) in the presence of a suitable base and solvent such as, e.g. potassium tert-butylate, butyllithium or sodium hydride in, e.g. tetrahydrofuran (step b). Depending on the reaction conditions intermediates 19 can exists as cis, trans or mixture of cis/trans isomers. Intermediates 19 can be transformed into Compounds of the general formula IK-IN in which n equals 0 and A signifies nitrogen can be prepared described in Scheme 8. Intermediates 18 (prepared as described above) are reacted with an alkyl- or optionally substituted arylamine in the presence of a reducing agent such as, e.g. cyanoborohydride, sodium triacetoxyborohydride or di-n-butyltin dichloride with triphenylsilane in an appropriate solvent such as, e.g. tetrahydrofuran to furnish compounds IK (step a). In those cases where compounds IK contain ester or cyano groups, these can be converted into the corresponding carboxylic acid and tetrazole groups (step b), respectively, applying the conditions described before. Compounds IM can be prepared by alkylation of compounds IK for example with $R^8LG$ (LG signifies a leaving group such as, e.g. chloro, bromo, $OSO_2$alkyl, $OSO_2$fluoroalkyl or $OSO_2$aryl, $R^8$ is as defined above) in appropriate solvents such as, e.g. N,N'-dimethylformamide and using a suitable base such as, e.g. cesium carbonate or sodium hydride. In certain cases it can be advantageous to convert the amine to a carbamate function (e.g. a carbamic acid tert-butyl ester (Boc)) prior to the alkylation reaction and to remove the Boc protective group after the alkylation step under conditions described in literature and known to those skilled in the art. Alternatively, compounds IM can be synthesized from compounds IK via reductive amination using aldehydes of the type $R^8CHO$ and applying conditions as described before. If compounds IK and IM carry an ester or cyano group they can be converted into the corresponding carboxylic acid and tetrazole groups, respectively, applying the conditions described above.

Alternatively, compounds IK-IN can be prepared according to Scheme 9. Intermediates 8 can be transformed into intermediates 19 by, e.g. treating the acid group in 8 with an activating agent such as, e.g. N-hydroxybenzotriazole monohydrate, optionally together with 1-ethyl-3-(3-dimethylaminopropyl)carbodiimide hydrochloride, in the presence of a base such as, e.g. ethyl diisopropylamine in a suitable solvent such as, e.g. N,N-dimethylformamide and an ammonia source such as, e.g. ammonium chloride (step a). The amide group in intermediates 19 can be converted to the amine by, e.g. treatment with a reducing agent such as, e.g. lithium aluminium hydride in a suitable solvent such as, e.g. tetrahydrofuran to give intermediate 20 (step b). Intermediates 20 can be alternatively obtained from intermediates 17 (prepared as described above) by converting them to the azide (intermediate 20, step f) by, e.g. reaction with sodium azide in a suitable solvent such as, e.g. N,N-dimethylformamide and reduction of the azide to the amine (step g) by, e.g. catalytic hydrogenation applying the same methods as described above. Intermediates 20 can be transformed into compounds of formula IK though alkylation or reductive amination according to the methods described before (step c). Compounds IK can be further converted into compounds IL through alkylation or reductive amination applying the methods described before (step d). In case compounds IK and IL contain ester or cyano groups they can be converted into the corresponding carboxylic acid and tetrazole groups, respectively, applying the conditions described before, to furnish compounds IM and IN (step e).

Scheme 8

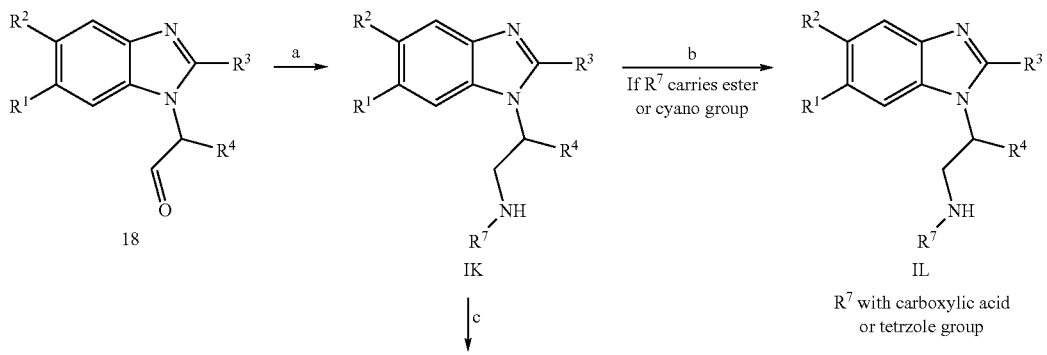

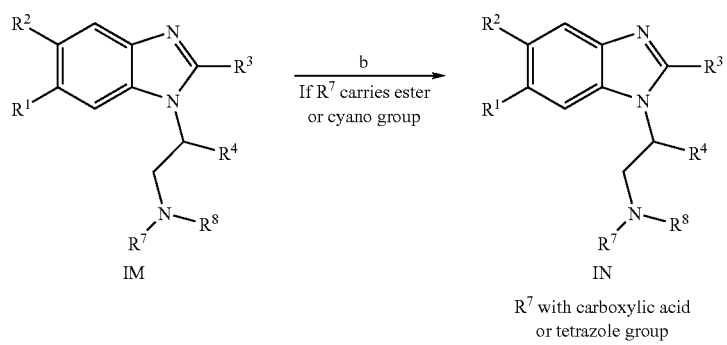

Scheme 9

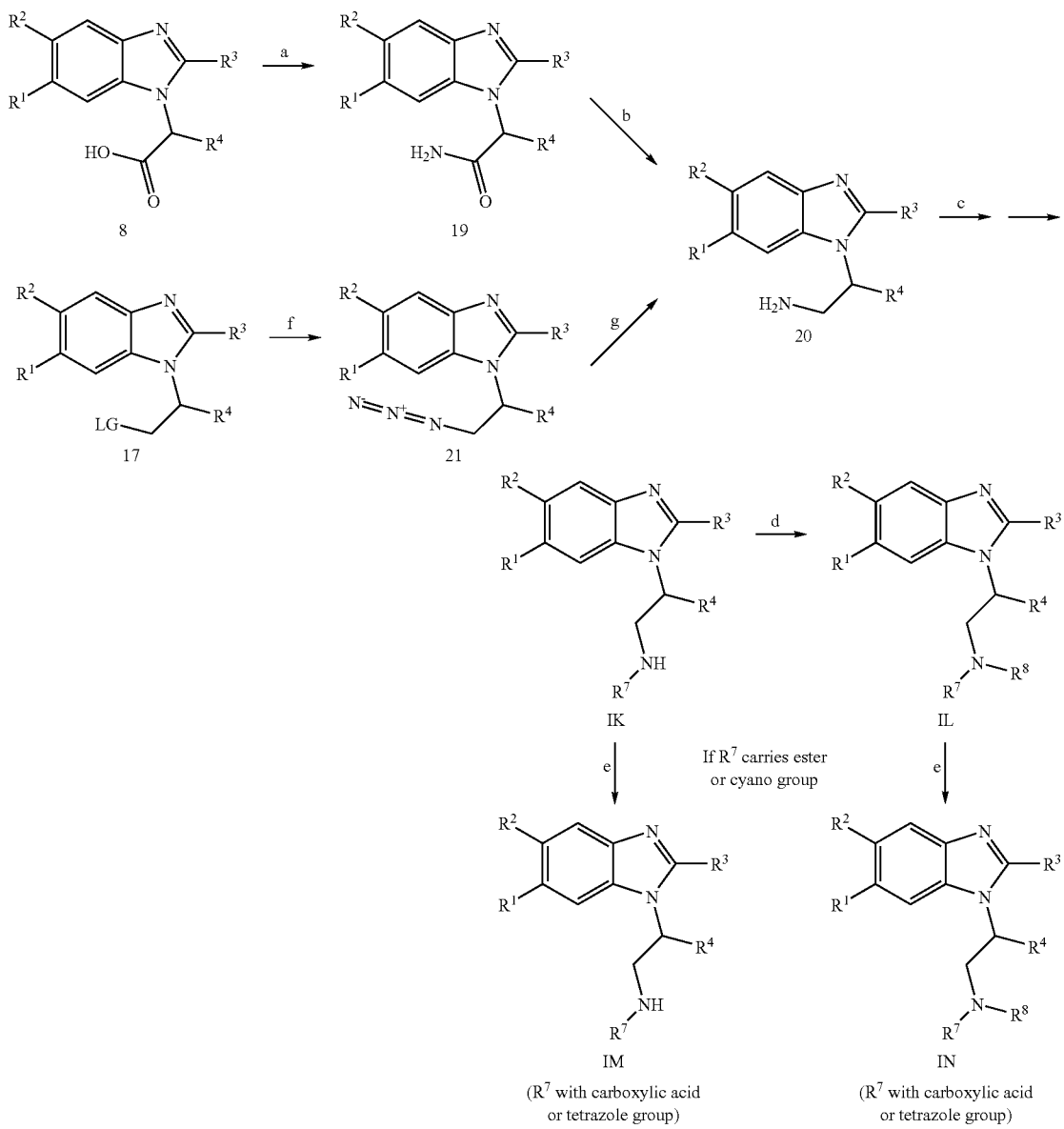

Compounds IK-IN can also be prepared according to Scheme 10 if substituents $R^1$ to $R^8$ are stable under the reducing conditions applied in steps b and f. Amide coupling of intermediates 8 with optionally substituted amines $R^7NH_2$ or $R^7R^8NH$ (either commercially available or accessible by methods described in references or by methods known in the art) gives compounds 22 (step a) or 23 (step e). Amide couplings of this type are widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent like, e.g. N,N-dimethylformamide (DMF) or dioxane, optionally in the presence of a base (e.g. triethylamine, diisopropylethylamine or 4-(dimethylamino)pyridine). Alternatively, intermediates 22 and 23 can be obtained by converting intermediates 8 into their acid chlorides by treatment with, e.g. thionyl chloride, optionally in a solvent such as, e.g. dichloromethane and reaction of the acid chloride with optionally substituted cycloalkyl/(hetero)aryl amines in an appropriate solvent such as, e.g. dichloromethane and a base such as, e.g. triethylamine, pyridine diisopropylethylamine or 4-(dimethylamino)pyridine. Intermediates 23 can also be obtained by alkylation of intermediates 22 (step g) by the methods described before. Conversion of intermediates 22 into compounds IK (step b) and of intermediates 23 into compounds IL (step f) can be accomplished for example by treating intermediates 22 or 23 with a suitable reducing agent such as, e.g. lithium aluminium hydride, di-isobutylaluminum hydride or borane dimethyl sulfide or tetrahydrofuran complex in a suitable solvent such as, e.g. diethyl ether, tert-butyl methyl ether or tetrahydrofuran at temperatures between 0° C. and the boiling point of the solvent. Conversion of compounds IK into IL (step c) and compounds IK and IL into compounds IM and IN, respectively (step d) can be accomplished according to the methods described above.

Scheme 10

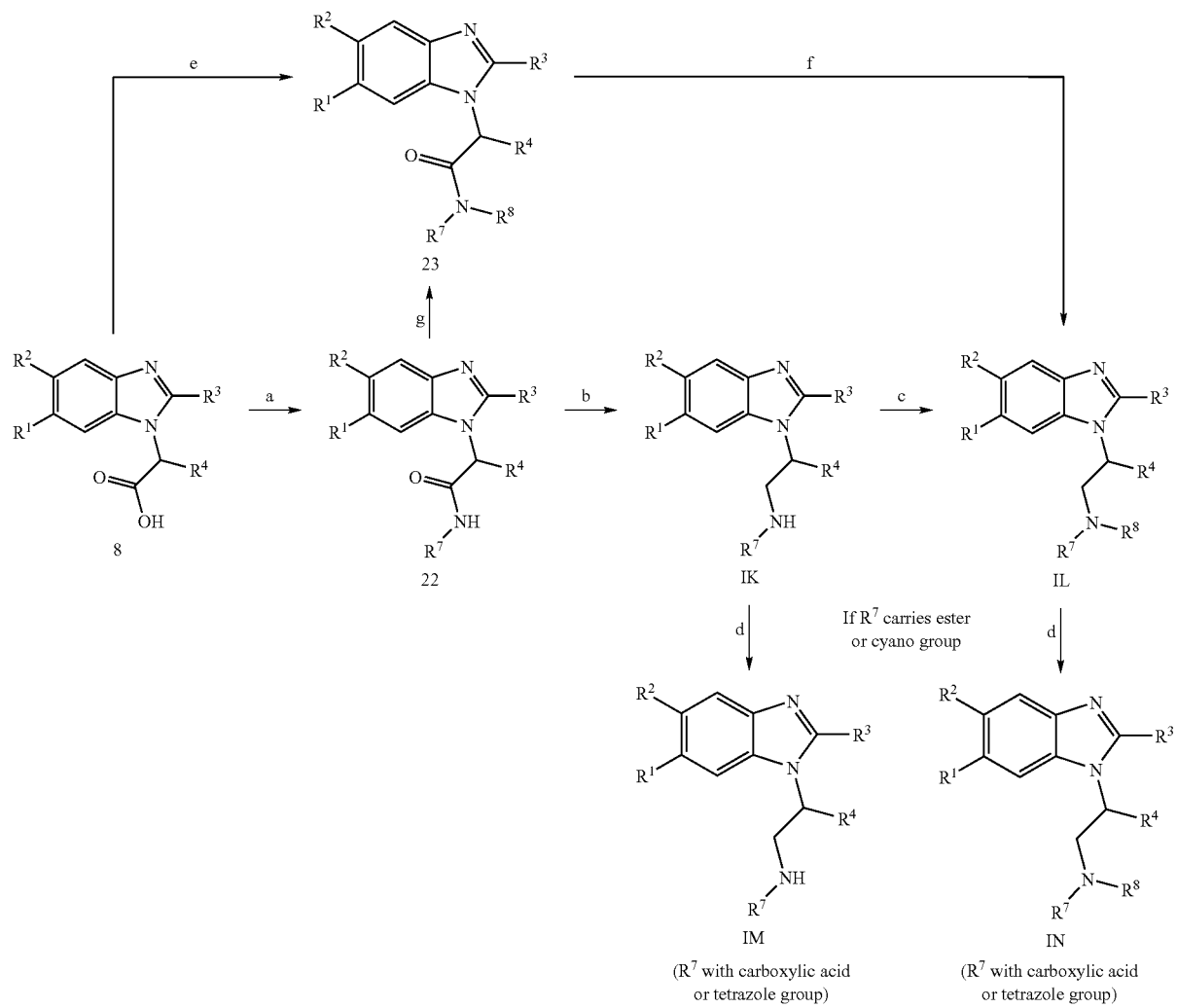

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wutts, $2^{nd}$ Ed., 1991, Wiley N.Y.) can be introduced before the critical step applying methods well known in the art. Such protecting groups can be removed at a later stage of the synthesis using standard methods described in the literature.

If compounds (1) to (7), (9) to (11) and (14) contain stereogenic centers, compounds (I) can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization with optically pure acids or by separation of the antipodes by specific chromatographic methods using either a chiral adsorbent or a chiral eluant.

If desired or required functional groups present in I (such as —$CO_2$ alkyl, amino groups, cyano groups and others) may be derivatized to other functional groups using typical standard procedures known to those skilled in the art (e.g. reduction of —$CO_2$ alkyl to —$CH_2$OH with $LiAlH_4$, hydrolysis of —$CO_2$ alkyl to —$CO_2H$ and subsequent optional conversion to an amide, acylation of amino groups).

The invention also relates to a process for the manufacture of compounds of formula (I), which process comprises one of the following steps:

(a) the reaction of a compound of formula (II)

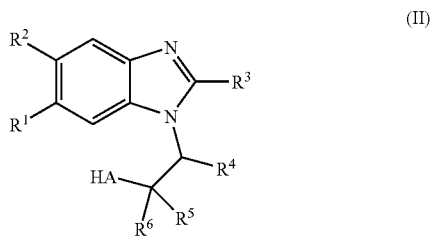

with a compound of formula $R^7$ $(CH_2)_n X$, optionally followed by the reaction of the resulting product in the presence of base or in the presence of acid, wherein A, $R^1$ to $R^7$ and n are as defined above and X is a leaving group;

(b) the reaction of a compound of formula (III)

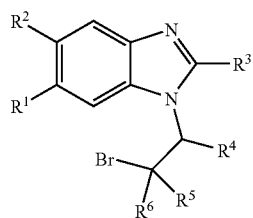
(III)

with a compound of formula $R^7$ $(CH_2)_n AH$, optionally followed by the reaction of the resulting product in the presence of base or in the presence of acid, wherein A, $R^1$ to $R^7$ and n are as defined above.

The base is, for example, an alkali metal hydroxyde like lithium or sodium hydroxide. In that case, the reaction is preferably carried out in a polar solvent, for example methanol, water, tetrahydrofuran or mixtures thereof.

The acid is, for example, hydrochloric acid or formic acid. Hydrochloric acid is used preferably in tetrahydrofuran and formic acid in an alcohol like isopropanol.

The leaving group X is, for example, bromide, $-OSO_2$-alkyl, $-OSO_2$-fluoroalkyl or $-OSO_2$-aryl.

The invention also relates to compounds of formula (I), when manufactured by the process as defined above.

As described above, the novel compounds of the present invention have been found to bind to and selectively activate FXR. They can therefore be used in the treatment and prophylaxis of diseases that are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and/or Alzheimer's disease.

Also contemplated herein is combination therapy using one or more compounds or compositions provided herein, or a pharmaceutically acceptable derivative thereof, in combination with one or more of the following: cholesterol biosynthesis inhibitors (HMG CoA reductase inhibitors, e.g. lovastatin, simvastatin, pravastatin, fluvastatin, atorvastatin, cerivastatin, nisvastatin and rivastatin); squalene epoxidase inhibitors (e.g. terbinafine); plasma HDL-raising agents (e.g. CETP inhibitors e.g. anacetrapib, R1658); human peroxisome proliferator activated receptor (PPAR) gamma agonists (e.g. thiazolidinediones e.g. rosiglitazone, troglitazone, and pioglitazone); PPAR alpha agonists (e.g. clofibrate, fenofibrate and gemfibronzil); PPAR dual alpha/gamma agonists (e.g. muraglitazar, aleglitazar, peliglitazar); bile acid sequestrants (e.g. anion exchange resins, or quaternary amines (e.g. cholestyramine or colestipol)); bile acid transport inhibitors (BATi); nicotinic acid, niacinamide; cholesterol absorption inhibitors (e.g. ezetimibe); acyl-Coenzyme A:cholesterol O-acyl transferase (ACAT) inhibitors (e.g. avasimibe); selective estrogen receptor modulators (e.g. raloxifene or tamoxifen); LXR alpha or beta agonists, antagonists or partial agonists (e.g. 22(R)-hydroxycholesterol, 24(S)-hydroxycholesterol, T0901317 or GW3965); microsomal triglyceride transfer protein (MTP) inhibitors, anti-diabetes agents such as, e.g. insulin and insulin analogs (e.g. LysPro insulin, inhaled formulations comprising insulin; sulfonylureas and analogues (e.g. tolazamide, chlorpropamide, glipizide, glimepiride, glyburide, glibenclamide, tolbutamide, acetohexamide, glypizide), biguanides (e.g. metformin or metformin hydrochloride, phenformin, buformin) alpha2-antagonists and imidazolines (e.g. midaglizole, isaglidole, deriglidole, idazoxan, efaroxan, fluparoxan), thiazolidinediones (e.g. pioglitazone hydrochloride, rosiglitazone maleate, ciglitazone, troglitazone or balaglitazone), alpha-glucosidase inhibitors (e.g. miglitol, acarbose, epalrestat, or voglibose), meglitinides (e.g. repaglinide or nateglinide), DPP-4 inhibitors (e.g. sitagliptin phosphate, saxagliptin, vildagliptin, alogliptin or denagliptin), incretins (e.g. glucagon-like peptide-1 (GLP-1) receptor agonists (e.g. Exenatide (Byetta™), NN2211 (Liraglutide), GLP-1(7-36) amide and its analogs, GLP-1(7-37) and its analogs, AVE-0010 (ZP-10), R1583 (Taspoglutide), GSK-716155 (albiglutide, GSK/Human Genome Sciences), BRX-0585 (Pfizer/Biorexis) and CJC-1134-PC (Exendin-4:PC-DAC™ and glucose-dependent insulinotropic peptide (GIP)); amylin agonists (e.g. pramlintide, AC-137); insulin secretagogues (e.g. linogliride, nateglinide, repaglinide, mitiglinide calcium hydrate or meglitinide); SGLT-2 inhibitors (e.g. dapagliflozin (BMS), sergliflozin (Kissei), AVE 2268 (Sanofi-Aventis); Glucokinase activators such as the compounds disclosed in e.g. WO 00/58293 A1; anti-obesity agents such as nerve growth factor agonist (e.g. axokine), growth hormone agonists (e.g. AOD-9604), adrenergic uptake inhibitors (e.g. GW-320659), 5-HT (serotonin) reuptake/transporter inhibitors (e.g. Prozac), 5-HT/NA (serotonin/noradrenaline) reuptake inhibitors (e.g. sibutramine), DA (dopamine) reuptake inhibitors (e.g. Buproprion), 5-HT, NA and DA reuptake blockers, steroidal plant extracts (e.g. P57), NPY1 or 5 (neuropeptide Y Y1 or Y5) antagonists, NPY2 (neuropeptide Y Y2) agonists, MC4 (melanocortin 4) agonists, CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g. SNAP 7941), MCH2R (melanin concentrating hormone 2R) agonist/antagonists, H3 (histamine receptor 3) inverse agonists or antagonists, H1 (histamine 1 receptor) agonists, FAS (Fatty acid synthase) inhibitors, ACC-2 (acetyl-CoA carboxylase-1) inhibitors, β3 (beta adrenergic receptor 3) agonists, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, GLP-1 (glucagons-like peptide-1) agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), NN2211, Topiramate, glucocorticoid antagonist, Exendin-4 agonists, $5\text{-HT}_{2C}$ (serotonin receptor 2C) agonists (e.g. Lorcaserin), PDE (phosphodiesterase) inhibitors, fatty acid transporter inhibitors, dicarboxylate transporter inhibitors, glucose transporter inhibitors, CB-1 (cannabinoid-1 receptor) inverse agonists or antagonists (e.g. SR141716), lipase inhibitors (e.g. orlistat); cyclooxygenase-2 (COX-2) inhibitors (e.g. rofecoxib and celecoxib); thrombin inhibitors (e.g. heparin, argatroban, melagatran, dabigatran); platelet aggregation inhibitors (e.g. glycoprotein IIb/IIIa fibrinogen receptor antagonists or aspirin); vitamin B6 and pharmaceutically acceptable salts thereof; vitamin B 12; folic acid or a pharmaceutically acceptable salt or ester thereof; antioxidant vitamins such as C and E and beta carotene; beta blockers (e.g. angiotensin II receptor antagonists such as losartan, irbesartan or valsartan; antiotensin converting enzyme inhibitors such as enalapril and captopril; calcium channel blockers such as nifedipine and diltiazam; endothelian antagonists; aspirin; agents other than LXR ligands that enhance ATP-Binding Cassette Transporter-A1 gene expression; and bisphosphonate compounds (e.g. alendronate sodium).

The invention therefore also relates to pharmaceutical compositions comprising a compound as defined above and a pharmaceutically acceptable carrier and/or adjuvant.

In another preferred embodiment, the invention relates to a method for the therapeutic and/or prophylactic treatment of diseases which are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and/or Alzheimer's disease, which method comprises administering an effective amount of a compound of formula (I) to a human being.

The invention also embraces the use of compounds as defined above for the therapeutic and/or prophylactic treatment of diseases which are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and/or Alzheimer's disease.

The invention also relates to the use of compounds as described above for the preparation of medicaments for the therapeutic and/or prophylactic treatment of diseases which are affected by FXR modulators, preferably FXR agonists. Such diseases include increased lipid and cholesterol levels, particularly high LDL-cholesterol, high triglycerides, low HDL-cholesterol, dyslipidemia, diseases of cholesterol absorption, atherosclerotic disease, peripheral occlusive disease, ischemic stroke, diabetes, particularly non-insulin dependent diabetes mellitus, metabolic syndrome, diabetic nephropathy, obesity, cholesterol gallstone disease, cholestasis/fibrosis of the liver, non-alcoholic steatohepatitis (NASH), non-alcoholic fatty liver disease (NAFLD), psoriasis, cancer, particularly gastrointestinal cancer, osteoporosis, Parkinson's disease and/or Alzheimer's disease. Such medicaments comprise a compound as described above.

Prevention and/or treatment of high LDL cholesterol levels, high triglycerides, dyslipidemia, cholesterol gallstone disease, cancer, non-insulin dependent diabetes mellitus and metabolic syndrome is preferred, particularly high LDL cholesterol, high triglyceride levels and dyslipidemia.

Also preferred is the prevention and/or treatment of non-insulin dependent diabetes mellitus and dyslipidemia.

The following tests were carried out in order to determine the activity of the compounds of formula (I). Background information on the binding assay can be found in: Nichols J S et al. "Development of a scintillation proximity assay for peroxisome proliferator-activated receptor gamma ligand binding domain", (1998) Anal. Biochem. 257: 112-119.

Bacterial and mammalian expression vectors were constructed to produce glutathione-s-transferase (GST) and Gal4 DNA binding domain (GAL) proteins fused to the ligand binding domain (LBD) of human FXR (aa 193-473). To accomplish this, the portions of the sequences encoding the FXR LBD were amplified by polymerase chain reaction (PCR) from a full-length clone by PCR and then subcloned into the plasmid vectors. The final clone was verified by DNA sequence analysis.

The induction, expression, and subsequent purification of GST-LBD fusion protein was performed in *E. coli* strain BL21(pLysS) cells by standard methods (Current Protocols in Molecular Biology, Wiley Press, ed. Ausubel et al.).

Radioligand Binding Assay

Binding of test substances to the FXR ligand binding domain was assessed in a radioligand displacement assay. The assay was performed in a buffer consisting of 50 mM Hepes, pH 7.4, 10 mM NaCl, 5 mM $MgCl_2$, 0.01% CHAPS. For each reaction well in a 96-well plate, 40 nM of GST-FXR LBD fusion protein was bound to 10 μg glutathione yttrium silicate SPA beads (Pharmacia Amersham) in a final volume of 50 μl by shaking. A radioligand (e.g., 20 nM of 2,N-dicyclohexyl-2-[2-(2,4 dimethoxy-phenyl)-benzoimidazol-1-yl]-acetamide) and test compounds were added, and scintillation proximity counting was performed. All binding assays were performed in 96-well plates and the amount of bound ligand was measured on a Packard TopCount using OptiPlates (Packard). Dose response curves were performed within a range of test compound concentrations from $6 \times 10^{-9}$ M to $2.5 \times 10^{-5}$ M and $IC_{50}$ values were calculated.

The compounds according to formula (I) have an activity in the above assay ($IC_{50}$), preferably of 0.001 μM to 10 μM, more preferably 0.001 μM to 0.1 μM.

For example, the following compounds showed the following $IC_{50}$ values in the assay described above.

| Example | h-$IC_{50}$ Binding [μM] |
| --- | --- |
| 1 | |
| 2 | 0.06 |
| 3 | 32.1 |
| 4 | 0.07 |
| 5 | 0.04 |
| 6 | 0.09 |
| 7 | 0.02 |
| 8 | 0.02 |
| 9 | 0.1 |
| 10 | 0.03 |
| 11 | 0.02 |
| 12 | 0.05 |
| 13 | 0.1 |
| 14 | 2.0 |
| 15 | 0.07 |
| 16 | 0.2 |
| 17 | 0.2 |
| 18 | 1.3 |
| 19 | 0.05 |
| 20 | 0.03 |
| 21 | 0.6 |
| 22 | 0.03 |
| 23 | 0.02 |
| 24 | 0.02 |
| 25 | 0.8 |
| 26 | 0.02 |
| 27 | 0.3 |
| 28 | 0.04 |
| 29 | 0.2 |
| 30 | 0.5 |
| 31 | 0.6 |
| 32 | 1.0 |
| 33 | 0.5 |
| 34 | 0.04 |
| 35 | 0.2 |
| 36 | 0.09 |
| 37 | 0.4 |

| Example | h-IC$_{50}$ Binding [μM] |
|---|---|
| 38 | 0.1 |
| 39 | 0.03 |
| 40 | 0.1 |
| 41 | 0.07 |
| 42 | 0.2 |
| 43 | 0.7 |
| 44 | 0.4 |
| 45 | 0.02 |
| 46 | 0.1 |
| 47 | 0.3 |
| 48 | 0.5 |
| 49 | 0.4 |
| 50 | 0.1 |
| 51 | 0.3 |
| 52 | 0.08 |
| 53 | 0.03 |
| 54 | 0.1 |
| 55 | 0.004 |
| 56 | 0.05 |
| 57 | 0.1 |
| 58 | 0.1 |
| 59 | 0.06 |
| 60 | 0.5 |
| 61 | 1.4 |
| 62 | 0.2 |
| 63 | 0.09 |
| 64 | 0.3 |
| 65 | 0.2 |
| 66 | 0.01 |
| 67 | 2.5 |
| 68 | 0.06 |
| 69 | 0.7 |
| 70 | 0.01 |
| 71 | 0.06 |
| 72 | 0.001 |
| 73 | 0.1 |
| 74 | 0.5 |
| 75 | 0.09 |
| 76 | 0.004 |
| 77 | 0.003 |
| 78 | 0.03 |
| 79 | 0.6 |
| 80 | 0.05 |
| 81 | 0.01 |
| 82 | 0.001 |
| 83 | 0.0002 |
| 84 | 0.06 |
| 85 | 0.01 |
| 86 | 0.003 |
| 87 | 0.04 |
| 88 | 0.003 |
| 89 | 0.01 |
| 90 | 0.2 |
| 91 | 0.06 |
| 92 | 0.09 |
| 93 | 0.3 |
| 94 | 0.1 |
| 95 | 0.6 |
| 96 | 0.002 |
| 97 | 0.05 |
| 98 | 0.001 |
| 99 | 0.002 |
| 100 | 0.02 |
| 101 | 0.0002 |
| 102 | 0.03 |
| 103 | 0.10 |
| 104 | 0.05 |
| 105 | 0.04 |
| 106 | 0.10 |
| 107 | 0.01 |
| 108 | 0.01 |
| 109 | 0.03 |
| 110 | 0.06 |
| 111 | 0.02 |
| 112 | 0.11 |
| 113 | 0.002 |
| 114 | 0.06 |
| 115 | 0.002 |
| 116 | 0.002 |
| 117 | 0.04 |
| 118 | 0.31 |
| 119 | 0.11 |
| 120 | 0.03 |
| 121 | 0.02 |
| 122 | 0.18 |
| 123 | 0.03 |
| 124 | 0.003 |
| 125 | 0.01 |
| 126 | 0.03 |
| 127 | 0.001 |
| 128 | 0.02 |
| 129 | 0.02 |
| 130 | 0.3 |
| 131 | 0.02 |
| 132 | 0.01 |
| 133 | 0.01 |
| 134 | 0.01 |
| 135 | 0.02 |
| 136 | 0.1 |
| 137 | 6.1 |
| 138 | 0.3 |
| 139 | 0.003 |
| 140 | 0.07 |
| 141 | 8.2 |
| 142 | 0.005 |
| 143 | 0.003 |
| 144 | 0.2 |
| 145 | 0.0003 |
| 146 | 0.001 |
| 147 | 0.0004 |

The compounds of formula (I) and/or their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Example 1

2-(4-Chloro-phenyl)-1-(1-cyclohexyl-2-cyclohexyl-methoxy-ethyl)-5,6-difluoro-1H-benzoimidazole To a solution of 0.58 g (1.48 mmol) 2-[2-(4-chloro-phenyl)-5,6-difluoro-benzoimidazol-1-yl]-2-cyclohexyl-ethanol (Ex. 1, int. c) in 6 mL N,N-dimethylformamide, 71 mg (1.5 mmol, 55% dispersion in mineral oil) sodium hydride and after 5 min. 0.32 g (1.78 mmol) bromomethylcyclohexane were added. The reaction mixture was warmed to 50° C. and after 4 h another 71 mg sodium hydride and 0.32 g (1.78 mmol) bromomethylcyclohexane were added. A third batch sodium hydride and bromomethylcyclohexane were added after 3 h. After stirring overnight the reaction mixture was poured on water and ethyl acetate, extracted, the aqueous phase extracted twice with ethyl acetate and the aqueous phase extracted twice with ethyl acetate. The combined organic layers were washed twice with water and once with brine, dried over magnesium sulfate and evaporated. The crude product was purified by silica gel column chromatography using a MPLC system (CombiFlash Companion, Isco Inc.) eluting with a gradient of n-heptane:ethylacetate (1:0 to 4:1) to yield the title compound as a white solid (39%). MS (Turbo Spray): m/z=487.3 [M+H].

Intermediates a)
2-(4-Chloro-phenyl)-5,6-difluoro-1H-benzoimidazole

The mixture of 50.7 g (0.35 mol) 1,2-diamino-4,5-difluorobenzene, 55.1 g (0.35 mol) 4-chlorobenzoic acid and 507 g polyphosphoric acid was heated to 160° C. and stirred at this temperature for 90 min. After cooling to 55° C., 1000 mL water and 500 mL ethyl acetate were added. Under ice cooling ca 1000 mL 32% aqueous sodium hydroxide solution was added (pH ca 9). The suspension was filtered over dicalite and the filter cake was washed with 1.5 L ethyl acetate. The phases were separated and the aqueous phase was washed with 0.5 L ethyl acetate. The organic phases were washed with 1M aqueous sodium hydroxide solution and brine, dried over magnesium sulfate and filtered. To the solution, silica gel was added and the solvent evaporated. The crude adsorbed product was purified by column chromatography over silica gel using a gradient of n-heptane:ethyl acetate (4:1 to 1:1, v/v) as eluant. The fractions containing the product in pure form were pooled and evaporated. The remaining fractions were dissolved in ethyl acetate, washed twice with 1M aqueous sodium hydroxide solution and brine, the combined aqueous layers extracted once with ethyl acetate and the combined organic layers dried over magnesium sulfate and filtered. Chromatography over silica gel afforded a second batch of compound. Total yield: 75 g (80%) light yellow solid. MS (Turbo Spray): m/z=264.9 [M+H].

b) [2-(4-Chloro-phenyl)-5,6-difluoro-benzoimidazol-1-yl]-cyclohexyl-acetic acid ethyl ester To the solution of 75 g (0.28 mol) 2-(4-chloro-phenyl)-5,6-difluoro-1H-benzoimidazole in 750 mL N,N-dimethylformamide 116 g (0.33 mol) cesium carbonate and 88 g (0.35 mol) bromo-cyclohexyl-acetic acid ethyl ester (commercially available) were added. The mixture was heated to 100° C. and after stirring for 90 min. another 116 g cesium carbonate and 88 g bromo-cyclohexyl-acetic acid ethyl ester were added. After 6 h another 116 g cesium carbonate and 88 g bromo-cyclohexyl-acetic acid ethyl ester were added. After 22 h (total reaction time) the reaction mixture was cooled to 30° C. and was poured on 1 L ice water and 2 L ethyl acetate. The phases were separated and the aqueous phase extracted with 500 mL ethyl acetate. The combined organic phases were washed three times with 500 mL ice water and once with brine, dried over magnesium sulfate and filtered. To the solution, silica gel was added and the solvent evaporated. The crude adsorbed product was purified by column chromatography over silica gel using n-heptane:ethyl acetate (9:1 v/v) as eluant. The product-containing fractions were pooled and the solvent evaporated until a suspension had formed. The suspension was cooled in an ice bath and filtered to give 92 g (75%) of the desired product as colorless solid. MS (Turbo Spray): 433.1 [M+H].

c) 2-[2-(4-Chloro-phenyl)-5,6-difluoro-benzoimidazol-1-yl]-2-cyclohexyl-ethanol

To the solution of 1.0 g (2.3 mmol) [2-(4-chloro-phenyl)-5,6-difluoro-benzoimidazol-1-yl]-cyclohexyl-acetic acid ethyl ester in 20 mL tetrahydrofuran, 88 mg (2.3 mmol) lithium aluminium hydride were added. A slight warming occurred. After 15 min. the reaction mixture was poured on water and ethyl acetate, extracted, the aqueous phase extracted twice with ethyl acetate and the aqueous phase extracted twice with ethyl acetate. The combined organic layers were washed with brine, dried over magnesium sulfate and evaporated. The crude product was purified by silica gel column chromatography using a MPLC system (CombiFlash Companion, Isco Inc.) eluting with a gradient of n-heptane:ethyl acetate (100:0 to 100:40 v/v) to yield the title compound as an off-white solid (67%). MS (Turbo Spray): m/z=391.2 [M+H].

Examples 2 and 3

The title compounds were obtained by separation of the stereoisomers of 2-(4-chloro-phenyl)-1-(1-cyclohexyl-2-cyclohexylmethoxy-ethyl)-5,6-difluoro-1H-benzoimidazole (Ex. 1) by chiral preparative HPLC (Chiralpak AD) eluting with a mixture of n-heptane/5% isopropanol.

(−)-2-(4-Chloro-phenyl)-1-(1-cyclohexyl-2-cyclohexylmethoxy-ethyl)-5,6-difluoro-1H-benzoimidazole White foam. MS (Turbo Spray): m/z=487.3 [M+H].

(+)-2-(4-Chloro-phenyl)-1-((S)-1-cyclohexyl-2-cyclohexylmethoxy-ethyl)-5,6-difluoro-1H-benzoimidazole White solid. MS (Turbo Spray): m/z=487.4 [M+H].

Example 4

4-{2-[2-(4-Chloro-phenyl)-5,6-difluoro-benzoimidazol-1-yl]-2-cyclohexyl-ethoxy}-benzoic acid To the solution of 0.22 g (0.4 mmol) 4-{2-[2-(4-chloro-phenyl)-5,6-difluoro-benzoimidazol-1-yl]-2-cyclohexyl-ethoxy}-benzoic acid ethyl ester in 3 mL dioxane, 50 mg (1.2 mmol) lithium hydroxide monohydrate and 3 mL water were added and the solution was stirred for 2 h at 100° C. After cooling to room temperature dioxane was evaporated and 7.6 mL 1N hydrochloric acid was added under stirring. The resulting suspension was filtered, thoroughly washed with water and the filter cake dried under high vacuum to give the product as a white solid (94%). MS (Turbo Spray): m/z=509.2 [M+H].
Intermediate 4-{2-[2-(4-Chloro-phenyl)-5,6-difluoro-benzoimidazol-1-yl]-2-cyclohexyl-ethoxy}-benzoic acid ethyl ester To the solution of 0.3 g (0.77 mmol) 2-[2-(4-chloro-phenyl)-5,6-difluoro-benzoimidazol-1-yl]-2-cyclohexyl-ethanol (Ex. 1, int. c) in 3 mL tetrahydrofuran, 0.13 g (0.84 mmol) ethyl 4-hydroxybenzoate and 0.22 g (084 mmol) triphenylphosphine were added. The solution was cooled to 0° C., 0.15 g (0.84 mmol) diethyl azodicarboxylate dissolved in 2 mL tetrahydrofuran were added dropwise and the reaction stirred at room temperature for 18 h. The reaction was adsorbed on silica gel and purified by silica gel column chromatography using a MPLC system (CombiFlash Companion, Isco Inc.) eluting with a gradient of n-heptane:ethyl acetate (100:0 to 100:40 v/v) to yield the title compound as a white foam (55%). MS (Turbo Spray): m/z=539.2 [M+H].

Examples 5 and 6

The title compounds were obtained by separation of the stereoisomers of 4-{2-[2-(4-chloro-phenyl)-5,6-difluoro-benzoimidazol-1-yl]-2-cyclohexyl-ethoxy}-benzoic acid (Ex. 4) by chiral preparative HPLC (Chiralpak AD) eluting with a mixture of n-heptane/30% ethanol/0.5% formic acid.

(+)-4-{2-[2-(4-Chloro-phenyl)-5,6-difluoro-benzoimidazol-1-yl]-2-cyclohexyl-ethoxy}-benzoic acid White solid. MS (Turbo Spray): m/z=511.0 [M+H].

(−)-4-{2-[2-(4-Chloro-phenyl)-5,6-difluoro-benzoimidazol-1-yl]-2-cyclohexyl-ethoxy}-benzoic acid White solid. MS (Turbo Spray): m/z=511.1 [M+H].

Example 7

4-{2-[2-(4-Chloro-phenyl)-5,6-difluoro-benzoimidazol-1-yl]-2-cyclohexyl-ethoxy}-3-fluorobenzoic acid The title compound was prepared in analogy to Example 4, from 4-{2-[2-(4-chloro-phenyl)-5,6-difluoro-benzoimidazol-1-yl]-2-cyclohexyl-ethoxy}-3-fluoro-benzoic acid methyl ester. White solid (99%). MS (Turbo Spray): m/z=527.0 [M−H].
Intermediate 4-{2-[2-(4-Chloro-phenyl)-5,6-difluoro-benzoimidazol-1-yl]-2-cyclohexyl-ethoxy}-3-fluoro-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 3-fluoro-4-hydroxy benzoic acid methyl ester (commercially available) and replacing di-ethyl azodicarboxylate by di-tert-butyl azodicarboxylate. White foam (81%). MS (Turbo Spray): m/z=543.0 [M+H].

Examples 8 and 9

The title compounds were obtained by separation of the stereoisomers of 4-{2-[2-(4-chloro-phenyl)-5,6-difluoro-benzoimidazol-1-yl]-2-cyclohexyl-ethoxy}-3-fluoro-benzoic acid (Ex. 7) by chiral preparative HPLC (Chiralpak AD) eluting with a mixture of n-heptane/10% ethanol/0.5% formic acid.

(−)-4-{2-[2-(4-Chloro-phenyl)-5,6-difluoro-benzoimidazol-1-yl]-2-cyclohexyl-ethoxy}-3-fluoro-benzoic acid White solid. MS (Turbo Spray): m/z=529.0 [M+H].

(+)-4-{2-[2-(4-Chloro-phenyl)-5,6-difluoro-benzoimidazol-1-yl]-2-cyclohexyl-ethoxy}-3-fluoro-benzoic acid White solid. (Turbo Spray): m/z=529.0 [M+H].

Example 10

3-Chloro-4-{2-[2-(4-chloro-phenyl)-5,6-difluoro-benzoimidazol-1-yl]-2-cyclohexyl-ethoxy}-benzoic acid The title compound was prepared in analogy to Example 4, from 3-chloro-4-{2-[2-(4-chloro-phenyl)-5,6-difluoro-benzoimidazol-1-yl]-2-cyclohexyl-ethoxy}-benzoic acid methyl ester. White solid (96%). MS (Turbo Spray): m/z=545.1 [M+H].
Intermediate 3-Chloro-4-{2-[2-(4-chloro-phenyl)-5,6-difluoro-benzoimidazol-1-yl]-2-cyclohexyl-ethoxy}-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and methyl 3-chloro-4-hydroxybenzoate (commercially available) and replacing di-ethyl azodicarboxylate by di-tert-butyl azodicarboxylate. White foam (81%). MS (Turbo Spray): m/z=559.1 [M+H].

Example 11

4-{2-[2-(4-Chloro-phenyl)-5,6-difluoro-benzoimidazol-1-yl]-2-cyclohexyl-ethoxy}-3-methyl-benzoic acid The title compound was prepared in analogy to Example 4, from 4-{2-[2-(4-chloro-phenyl)-5,6-difluoro-benzoimidazol-1-yl]-2-cyclohexyl-ethoxy}-3-methyl-benzoic acid methyl ester. White solid (87%). MS (Turbo Spray): m/z=523.0 [M−H].
Intermediate 4-{2-[2-(4-Chloro-phenyl)-5,6-difluoro-benzoimidazol-1-yl]-2-cyclohexyl-ethoxy}-3-methyl-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 4-hydroxy-3-methyl-benzoic acid methyl ester (commercially available) and replacing di-ethyl azodicarboxylate by di-tert-butyl azodicarboxylate. Colorless oil (60%). MS (Turbo Spray): m/z=539.2 [M+H].

Examples 12 and 13

The title compounds were obtained by separation of the stereoisomers of 4-{2-[2-(4-chloro-phenyl)-5,6-difluoro-benzoimidazol-1-yl]-2-cyclohexyl-ethoxy}-3-methyl-benzoic acid (Ex. 11) by chiral preparative HPLC (Chiralpak AD) eluting with a mixture of n-heptane/10% ethanol/0.5% formic acid.

(−)-4-{2-[2-(4-Chloro-phenyl)-5,6-difluoro-benzoimidazol-1-yl]-2-cyclohexyl-ethoxy}-3-methyl-benzoic acid White solid. MS (Turbo Spray): m/z=525.0 [M+H].

(+)-4-{2-[2-(4-Chloro-phenyl)-5,6-difluoro-benzoimidazol-1-yl]-2-cyclohexyl-ethoxy}-3-methyl-benzoic acid White solid. MS (Turbo Spray): m/z=525.0 [M+H].

Example 14

2-{2-[2-(4-Chloro-phenyl)-5,6-difluoro-benzoimidazol-1-yl]-2-cyclohexyl-ethoxy}-benzoic acid The title compound was prepared in analogy to Example 4, from 2-{2-[2-(4-chloro-phenyl)-5,6-difluoro-benzoimidazol-1-yl]-2-cyclohexyl-ethoxy}-benzoic acid methyl ester. White solid (66%). MS (Turbo Spray): m/z=509.2 [M−H].
Intermediate 2-{2-[2-(4-Chloro-phenyl)-5,6-difluoro-benzoimidazol-1-yl]-2-cyclohexyl-ethoxy}-benzoic acid methyl ester The title compound was prepared in analogy to Example 4, intermediate, from 2-[2-(4-chloro-phenyl)-5,6-difluoro-ben-zoimidazol-1-yl]-2-cyclohexyl-ethanol (Ex. 1, int. c) and methyl salicylate (commercially available) and replacing di-ethyl azodicarboxylate by di-tert-butyl azodicarboxylate. White solid (50%). MS (Turbo Spray): m/z=525.0 [M+H].

Example 15

3-{2-[2-(4-Chloro-phenyl)-5,6-difluoro-benzoimidazol-1-yl]-2-cyclohexyl-ethoxy}-benzoic acid The title compound was prepared in analogy to Example 4, from 3-{2-[2-(4-chloro-phenyl)-5,6-difluoro-benzoimidazol-1-yl]-2-cyclohexyl-ethoxy}-benzoic acid ethyl ester. White solid (57%). MS (Turbo Spray): m/z=509.2 [M−H].
Intermediate 3-{2-[2-(4-Chloro-phenyl)-5,6-difluoro-benzoimidazol-1-yl]-2-cyclohexyl-ethoxy}-benzoic acid ethyl ester The title compound was prepared in analogy to Example 4, intermediate, from 2-[2-(4-chloro-phenyl)-5,6-difluoro-ben-zoimidazol-1-yl]-2-cyclohexyl-ethanol (Ex. 1, int c) and ethyl 3-hydroxybenzoate (commercially available) and replacing di-ethyl azodicarboxylate by di-tert-butyl azodicarboxylate. White solid (32%). MS (Turbo Spray): m/z=539.2 [M+H].

Example 16

3-{2-[2-(4-Chloro-phenyl)-5,6-difluoro-benzoimidazol-1-yl]-2-cyclohexyl-ethoxy}-4-methyl-benzoic acid The title compound was prepared in analogy to Example 4, from 3-{2-[2-(4-chloro-phenyl)-5,6-difluoro-benzoimidazol-1-yl]-2-cyclohexyl-ethoxy}-4-methyl-benzoic acid ethyl ester. White solid (84%). MS (Turbo Spray): m/z=525.0 [M+H].
Intermediates a) 3-{2-[2-(4-Chloro-phenyl)-5,6-difluoro-benzoimidazol-1-yl]-2-cyclohexyl-ethoxy}-4-methyl-benzoic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 3-hydroxy-4-methyl-benzoic acid ethyl ester and replacing di-ethyl azodicarboxylate by di-tert-butyl azodicarboxylate. White solid (16%). MS (Turbo Spray): m/z=539.2 [M+H].

b) 3-Hydroxy-4-methyl-benzoic acid methyl ester

The solution of 3-hydroxy-4-methylbenzoic acid (commercially available) in 32 mL hydrochloric acid (1.25M in methanol) was refluxed for 5 h. After cooling to room temperature the solution was poured on saturated aqueous sodium bicarbonate solution and extracted three times with ethyl acetate. The organic layers were washed with brine, dried over magnesium sulfate and filtered to give the product as a white solid (99%) which was pure enough for the next step. MS (Turbo Spray): m/z=165.1 [M−H].

Example 17

3-{2-[2-(4-Chloro-phenyl)-5,6-difluoro-benzoimidazol-1-yl]-2-cyclohexyl-ethoxy}-2-methyl-benzoic acid The title compound was prepared in analogy to Example 4, from 3-{2-[2-(4-chloro-phenyl)-5,6-difluoro-benzoimidazol-1-yl]-2-cyclohexyl-ethoxy}-2-methyl-benzoic acid methyl ester. White solid (65%). MS (Turbo Spray): m/z=523.0 [M−H].
Intermediate 3-{2-[2-(4-Chloro-phenyl)-5,6-difluoro-benzoimidazol-1-yl]-2-cyclohexyl-ethoxy}-2-methyl-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and methyl 3-hydroxy-2-methylbenzoate (commercially available) and replacing di-ethyl azodicarboxylate by di-tert-butyl azodicarboxylate. White solid (9%). MS (Turbo Spray): m/z=539.2 [M+H].

Example 18

5-{2-[2-(4-Chloro-phenyl)-5,6-difluoro-benzoimidazol-1-yl]-2-cyclohexyl-ethoxy}-pyridine-2-carboxylic acid The title compound was prepared in analogy to Example 4, from 5-{2-[2-(4-chloro-phenyl)-5,6-difluoro-benzoimidazol-1-yl]-2-cyclohexyl-ethoxy}-pyridine-2-carboxylic acid methyl ester. White solid (56%). MS (Turbo Spray): m/z=510.3 [M−H].
Intermediate 5-{2-[2-(4-Chloro-phenyl)-5,6-difluoro-benzoimidazol-1-yl]-2-cyclohexyl-ethoxy}-pyridine-2-carboxylic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 5-hydroxy-pyridine-2-carboxylic acid methyl ester (commercially available). White solid (82%). MS (Turbo Spray): m/z=526.1 [M+H].

Example 19

6-{2-[2-(4-Chloro-phenyl)-5,6-difluoro-benzoimidazol-1-yl]-2-cyclohexyl-ethoxy}-nicotinic acid The title compound was prepared in analogy to Example 4, from 6-{2-[2-(4-chloro-phenyl)-5,6-difluoro-benzoimidazol-1-yl]-2-cyclohexyl-ethoxy}-nicotinic acid methyl ester. White solid (57%). MS (Turbo Spray): m/z=510.2 [M−H].
Intermediate 6-{2-[2-(4-Chloro-phenyl)-5,6-difluoro-benzoimidazol-1-yl]-2-cyclohexyl-ethoxy}-nicotinic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and methyl 6-hydroxynicotinate (commercially available) and replacing di-ethyl azodicarboxylate by di-tert-butyl azodicarboxylate. Colorless oil (78%). MS (Turbo Spray): m/z=526.2 [M+H].

Examples 20 and 21

The title compounds were obtained by separation of the stereoisomers of 6-{2-[2-(4-chloro-phenyl)-5,6-difluoro-benzoimidazol-1-yl]-2-cyclohexyl-ethoxy}-nicotinic acid (Ex. 19) by chiral preparative HPLC (Chiralpak AD) eluting with a mixture of n-heptane/10% ethanol/0.5% formic acid.

(+)-6-{2-[2-(4-Chloro-phenyl)-5,6-difluoro-benzoimidazol-1-yl]-2-cyclohexyl-ethoxy}-nicotinic acid White solid. MS (Turbo Spray): m/z=510.1 [M−H].

(−)-6-{2-[2-(4-Chloro-phenyl)-5,6-difluoro-benzoimidazol-1-yl]-2-cyclohexyl-ethoxy}-nicotinic acid White solid. MS (Turbo Spray): m/z=510.1 [M−H].

Example 22

5-Chloro-6-{2-[2-(4-chloro-phenyl)-5,6-difluoro-benzoimidazol-1-yl]-2-cyclohexyl-ethoxy}-nicotinic acid The title compound was prepared in analogy to Example 4, from 6-{2-[2-(4-chloro-phenyl)-5,6-difluoro-benzoimidazol-1-yl]-2-cyclohexyl-ethoxy}-nicotinic acid methyl ester. White solid (98%). MS (Turbo Spray): m/z=544.0 [M−H].
Intermediates a) 6-{2-[2-(4-Chloro-phenyl)-5,6-difluoro-benzoimidazol-1-yl]-2-cyclohexyl-ethoxy}-nicotinic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 5-chloro-6-hydroxy-nicotinic acid methyl ester and replacing di-ethyl azodicarboxylate by di-tert-butyl azodicarboxylate. White solid (83%). MS (Turbo Spray): m/z=560.3 [M+H].

b) 5-Chloro-6-hydroxy-nicotinic acid methyl ester

The solution of 2.0 g (11.5 mmol) 3-chloro-2-hydroxypyridine-5-carboxylic acid in 28 mL (35 mmol) hydrochloric acid (1.25M in methanol) was stirred for 5 h under reflux. The reaction was allowed to cool to room temperature, poured on 100 mL 10% aqueous sodium bicarbonate solution and 100 mL ethyl acetate, extracted and washed with 100 mL brine. The aqueous layer was extracted a second time with 100 mL ethyl acetate and the combined organic layers dried with magnesium sulfate, filtered and concentrated under vacuum. The light yellow residue was suspended in 30 mL tert-butyl methyl ether, stirred for 1 h at room temperature and filtered to give the desired compound as a white solid (55%) which was pure enough for the next step. MS (Turbo Spray): m/z=188.1 [M+H].

Examples 23 and 24

The title compounds were obtained by separation of the stereoisomers of 5-chloro-6-{2-[2-(4-chloro-phenyl)-5,6-difluoro-benzoimidazol-1-yl]-2-cyclohexyl-ethoxy}-nicotinic acid (Ex. 22) by chiral preparative HPLC (Chiralcel OD) eluting with a mixture of n-heptane/10% ethanol/0.5% formic acid).

(+)-5-Chloro-6-{2-[2-(4-chloro-phenyl)-5,6-difluoro-benzoimidazol-1-yl]-2-cyclohexyl-ethoxy}-nicotinic acid White solid. MS (Turbo Spray): m/z=543.9 [M+H].

(−)-5-Chloro-6-{2-[2-(4-chloro-phenyl)-5,6-difluoro-benzoimidazol-1-yl]-2-cyclohexyl-ethoxy}-nicotinic acid White solid. MS (Turbo Spray): m/z=543.9 [M+H].

Example 25

5-{2-[2-(4-Chloro-phenyl)-5,6-difluoro-benzoimidazol-1-yl]-2-cyclohexyl-ethoxy}-4-methyl-pyrimidine-2-carboxylic acid The title compound was prepared in analogy to Example 4, from 5-{2-[2-(4-chloro-phenyl)-5,6-difluoro-benzoimidazol-1-yl]-2-cyclohexyl-ethoxy}-4-methyl-pyrimidine-2-carboxylic acid ethyl ester. The white solid was purified by silica gel chromatography using a MPLC system (CombiFlash Companion, Isco Inc.) with a gradient of ethyl acetate:methanol (100:0 to 70:30 v/v) to give the desired product as a white solid (53%). MS (Turbo Spray): m/z=525.0 [M−H].
Intermediate 5-{2-[2-(4-Chloro-phenyl)-5,6-difluoro-benzoimidazol-1-yl]-2-cyclohexyl-ethoxy}-4-methyl-pyrimidine-2-carboxylic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 5-hydroxy-pyrazine-2-carboxylic acid ethyl ester (commercially available) and replacing di-ethyl azodicarboxylate by di-tert-butyl azodicarboxylate. White solid (81%). MS (Turbo Spray): m/z=555.3 [M+H].

Example 26

4-{2-[2-(4-Chloro-phenyl)-5,6-difluoro-benzoimidazol-1-yl]-2-cyclohexyl-ethoxy}-thieno[3,2-c]pyridine-7-carboxylic acid The title compound was prepared in analogy to Example 4, from 4-{2-[2-(4-chloro-phenyl)-5,6-difluoro-benzoimidazol-1-yl]-2-cyclohexyl-ethoxy}-thieno[3,2-c]pyridine-7-carboxylic acid ethyl ester. White solid (86%). MS (Turbo Spray): m/z=568.1 [M+H].
Intermediate 4-{2-[2-(4-Chloro-phenyl)-5,6-difluoro-benzoimidazol-1-yl]-2-cyclohexyl-ethoxy}-thieno[3,2-c]pyridine-7-carboxylic acid ethyl ester To the solution of 0.2 g (0.51 mmol) 2-[2-(4-chloro-phenyl)-5,6-difluoro-benzoimidazol-1-yl]-2-cyclohexyl-ethanol (Ex. 1, int. c) in 3 mL N,N-dimethylformamide, 27 mg (0.61 mmol) sodium hydride was added. After 15 min. 148 mg (0.61 mmol) chloro-thieno[3,2-c]pyridine-7-carboxylic acid ethyl ester was added and stirring was continued for another 2 h at room temperature. The reaction was poured on 20 mL 1N aqueous hydrochloric acid and 20 mL ethyl acetate. The phases were separated, the aqueous layers extracted with 20 mL ethyl acetate and the combined organic layers washed with 20 mL water and 20 mL brine, dried over magnesium sulfate, filtered and evaporated. The residue was purified by silica chromatography using a MPLC system (CombiFlash Companion, Isco Inc.) eluting with a gradient of n-heptane: ethyl acetate (100:0 to 75:25) to give the desired compound as a white solid (71%). MS (Turbo Spray): m/z=596.3 [M+H].

Examples 27 and 28

The title compounds were obtained by separation of the stereoisomers of 4-{2-[2-(4-chloro-phenyl)-5,6-difluoro-benzoimidazol-1-yl]-2-cyclohexyl-ethoxy}-thieno[3,2-c]pyridine-7-carboxylic acid (Ex. 26) by chiral preparative HPLC (Chiralpak AD) eluting with a mixture of n-heptane/15% ethanol/0.5% formic acid.

(+)-4-{2-[2-(4-Chloro-phenyl)-5,6-difluoro-benzoimidazol-1-yl]-2-cyclohexyl-ethoxy}-thieno[3,2-c]pyridine-7-carboxylic acid White solid. MS (Turbo Spray): m/z=566.0 [M−H].

(−)-4-{2-[2-(4-Chloro-phenyl)-5,6-difluoro-benzoimidazol-1-yl]-2-cyclohexyl-ethoxy}-thieno[3,2-c]pyridine-7-carboxylic acid White solid. MS (Turbo Spray): m/z=566.0 [M−H].

Example 29

2-(4-Chloro-phenyl)-1-[1-cyclohexyl-2-(pyridin-2-yloxy)-ethyl]-5,6-difluoro-1H-benzoimidazole The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 2-hydroxypyridine (commercially available) and replacing di-ethyl azodicarboxylate by di-tert-butyl azodicarboxylate. The crude product was purified by silica gel chromatography using a MPLC system (CombiFlash Companion, Isco Inc.) with a gradient of n-heptane:ethyl acetate (100:0 to 50:50). White solid (79%). MS (Turbo Spray): m/z=468.3 [M+H].

Example 30

6-{2-[2-(4-Chloro-phenyl)-5,6-difluoro-benzoimidazol-1-yl]-2-cyclohexyl-ethoxy}-pyridine-2-carboxylic acid The title compound was prepared in analogy to Example 4, from 6-{2-[2-(4-chloro-phenyl)-5,6-difluoro-benzoimidazol-1-yl]-2-cyclohexyl-ethoxy}-pyridine-2-carboxylic acid ethyl ester. White solid (91%). MS (Turbo Spray): m/z=510.3 [M−H].
Intermediate 6-{2-[2-(4-Chloro-phenyl)-5,6-difluoro-benzoimidazol-1-yl]-2-cyclohexyl-ethoxy}-pyridine-2-carboxylic acid ethyl ester The title compound was prepared in analogy to Example 26, intermediate, from 2-[2-(4-chloro-phenyl)-5,6-difluorobenzoimidazol-1-yl]-2-cyclohexyl-ethanol (Ex. 1, int. c) and ethyl 6-bromo-2-pyridinecarboxylate (commercially available) using a gradient of n-heptane:ethyl acetate (100:0 to 60:40). Light yellow foam (89%). MS (Turbo Spray): m/z=540.2 [M+H].

Example 31

2-{2-[2-(4-Chloro-phenyl)-5,6-difluoro-benzoimidazol-1-yl]-2-cyclohexyl-ethoxy}-6-methoxy-isonicotinic acid The title compound was prepared in analogy to Example 4, from 2-{2-[2-(4-chloro-phenyl)-5,6-difluoro-benzoimidazol-1-yl]-2-cyclohexyl-ethoxy}-6-methoxy-isonicotinic acid methyl ester. White solid (85%). MS (Turbo Spray): m/z=540.2 [M−H].
Intermediate 2-{2-[2-(4-Chloro-phenyl)-5,6-difluoro-benzoimidazol-1-yl]-2-cyclohexyl-ethoxy}-6-methoxy-isonicotinic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 2-hydroxy-6-methoxy-isonicotinic acid methyl ester (commercially available) and replacing di-ethyl azodicarboxylate by di-tert-butyl azodicarboxylate. Light yellow oil (77%). MS (Turbo Spray): m/z=556.2 [M+H].

Example 32

4-{2-[2-(4-Chloro-phenyl)-benzoimidazol-1-yl]-2-cyclohexyl-ethoxy}-benzoic acid

The title compound was prepared in analogy to Example 4, from 4-{2-[2-(4-chloro-phenyl)-benzoimidazol-1-yl]-2-cyclohexyl-ethoxy}-benzoic acid methyl ester. White solid (73%). MS (Turbo Spray): m/z=473.1 [M−H].
Intermediates a) [2-(4-Chloro-phenyl)-benzoimidazol-1-yl]-cyclohexyl-acetic acid ethyl ester To the solution of 1.0 g (4.4 mmol) 2-(4-chlorophenyl) benzimidazole (commercially available) in 10 mL N,N-dimethylformamide, 4.6 g (14.0 mmol) cesium carbonate and 3.3 g (13.1 mmol) bromo-cyclohexyl-acetic acid ethyl ester (commercially available) were added and the brown suspension was stirred for 22 h at 100° C. After cooling to room temperature the reaction was poured on water and extracted three times with ethyl acetate. The organic phases were washed with water and brine, dried over magnesium sulfate and filtered. To the filtrate silica gel was added and the solvent evaporated. The adsorbed crude product was purified by silica gel chromatography using a MPLC system (CombiFlash Companion, Isco Inc.) eluting with a gradient of n-heptane: ethyl acetate 100:0 to 50:50) to give the desired compound as a colorless solid (58%). MS (Turbo Spray): m/z=397.2 [M+H].

b) 2-[2-(4-Chloro-phenyl)-benzoimidazol-1-yl]-2-cyclohexyl-ethanol

The solution of 5.0 g (12.6 mmol) [2-(4-chloro-phenyl)-benzoimidazol-1-yl]-cyclohexyl-acetic acid ethyl ester in 75 mL dry tetrahydrofuran was cooled to 0° C. and 0.5 g (13.3 mmol) lithium aluminium hydride were added. The cooling bath was removed and stirring was continued for 2 h at room temperature. The reaction was poured on 300 mL 10% aqueous sodium-potassium-tartrate solution and 300 mL ethyl acetate. The phases were separated and the aqueous layer extracted with 300 mL ethyl acetate. The combined organic layers were washed with 300 mL brine, dried over magnesium sulfate, filtered and evaporated to give the desired compound as a white foam which was pure enough for the next step. MS (Turbo Spray): m/z=355.2 [M+H].

c) 4-{2-[2-(4-Chloro-phenyl)-benzoimidazol-1-yl]-2-cyclohexyl-ethoxy}-benzoic acid methyl ester The title compound was prepared in analogy to Example 4, intermediate, from 2-[2-(4-chloro-phenyl)-benzoimidazol-1-yl]-2-cyclohexyl-ethanol and methyl 4-hydroxy-benzoate (commercially available) and replacing di-ethyl azodicarboxylate by di-tert-butyl azodicarboxylate. White solid (58%). MS (Turbo Spray): m/z=489.3 [M+H].

Example 33

4-{2-[2-(4-Chloro-phenyl)-benzoimidazol-1-yl]-2-cyclohexyl-ethoxy}-3-fluoro-benzoic acid The title compound was prepared in analogy to Example 4, from 4-{2-[2-(4-chloro-phenyl)-benzoimidazol-1-yl]-2-cyclohexyl-ethoxy}-3-fluoro-benzoic acid methyl ester. White solid (91%). MS (Turbo Spray): m/z=493.3 [M+H].
Intermediate 4-{2-[2-(4-Chloro-phenyl)-benzoimidazol-1-yl]-2-cyclohexyl-ethoxy}-3-fluoro-benzoic acid methyl ester The title compound was prepared in analogy to Example 4, intermediate, from 2-[2-(4-chloro-phenyl)-benzoimidazol-1-yl]-2-cyclohexyl-ethanol and 3-fluoro-hydroxy-benzoic acid methyl ester (commercially available) and replacing di-ethyl azodicarboxylate by di-tert-butyl azodicarboxylate. White solid (91%). MS (Turbo Spray): m/z=507.3 [M+H].

Example 34

2-(4-Chloro-phenyl)-1-[1-cyclohexyl-2-(2-fluorophenoxy)-ethyl]-5,6-difluoro-1H-benzoimidazole To a solution of 27 mg (0.24 mmol) 2-fluorophenole in 2 mL N,N-dimethylformamide 11 mg (0.24 mmol, 55% dispersion in mineral oil) sodium hydride were added and the reaction mixture stirred for 10 min. at room temperature. To the suspension 100 mg (0.22 mmol) 1-(2-bromo-1-cyclohexyl-ethyl)-2-(4-chloro-phenyl)-5,6-difluoro-1H-benzoimidazole were added. The reaction mixture was stirred for 18 h at room temperature, and then poured on 30 mL 1N hydrochloric acid and 30 mL ethyl acetate. The phases were separated and the aqueous layer extracted a second time with 30 mL ethyl acetate. The combined organic layers were washed twice with 30 mL water and once with 30 mL brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate 100:0 to 70:30) to give the desired compound as white solid (9%). MS (Turbo Spray): m/z=485.3 [M+H].

Intermediate 1-(2-Bromo-1-cyclohexyl-ethyl)-2-(4-chloro-phenyl)-5,6-difluoro-1H-benzoimidazole The solution of 0.2 g (0.51 mmol) 2-[2-(4-chloro-phenyl)-5,6-difluoro-benzoimidazol-1-yl]-2-cyclohexyl-ethanol (Ex. 1, int. c) in 3 mL dichloromethane was cooled to 0° C. and 134 mg (0.51 mmol) triphenylphosphine and 170 mg (0.51 mmol) carbon tetrabromide were added. The reaction was stirred for 48 h at rt. and then evaporated. The residue was purified by silica gel chromatography using a MPLC system (CombiFlash Companion, Isco Inc.) eluting with a gradient of n-heptane:ethyl acetate (100:0 to 60:40) to give the desired compound as white solid (9%). MS (Turbo Spray): m/z=453.0 [M+H].

Example 35

2-(4-Chloro-phenyl)-1-[1-cyclohexyl-2-(pyridin-3-yloxy)-ethyl]-5,6-difluoro-1H-benzoimidazole To a solution of 46 mg (0.48 mmol) 3-hydroxypyridine in 3 mL N,N-dimethylformamide were added 21 mg (0.48 mmol, 55% dispersion in mineral oil) sodium hydride. The reaction mixture was stirred for 10 min. at room temperature. To this suspension 0.2 g (0.44 mmol) 1-(2-bromo-1-cyclohexyl-ethyl)-2-(4-chloro-phenyl)-5,6-difluoro-1H-benzoimidazole (Ex. 34, int.) were added and the reaction mixture stirred for 4 days at room temperature. The reaction mixture was poured on 30 mL 1N hydrochloric acid and 30 mL ethyl acetate and the phases separated. The aqueous layer was extracted with 30 mL ethyl acetate. The combined organic layers were washed twice with 30 mL water and once with 30 mL brine, dried over magnesium sulfate, filtered and evaporated. The residue was purified by silica gel chromatography using a MPLC system (CombiFlash Companion, Isco Inc.) eluting with a gradient of n-heptane:ethyl acetate (100:0 to 60:40) to give the desired compound as white solid (65%). MS (Turbo Spray): m/z=468.2 [M+H].

Example 36

2-(4-Chloro-phenyl)-1-[1-cyclohexyl-2-(pyridin-4-yloxy)-ethyl]-5,6-difluoro-1H-benzoimidazole The title compound was prepared in analogy to Example 35 from 1-(2-bromo-1-cyclohexyl-ethyl)-2-(4-chloro-phenyl)-5,6-difluoro-1H-benzoimidazole (Ex. 34, int.) and 4-hydroxypyridine after a reaction time of 3 days at room temperature. White solid (32%). MS (Turbo Spray): m/z=468.2 [M+H].

Example 37

2-{2-[2-(4-Chloro-phenyl)-5,6-difluoro-benzoimidazol-1-yl]-2-cyclohexyl-ethoxy}-isonicotinic acid The title compound was prepared in analogy to Example 4, from 2-{2-[2-(4-chloro-phenyl)-5,6-difluoro-benzoimidazol-1-yl]-2-cyclohexyl-ethoxy}-isonicotinic acid methyl ester. White solid (94%). MS (Turbo Spray): m/z=510.2 [M−H].

Intermediate

2-{2-[2-(4-Chloro-phenyl)-5,6-difluoro-benzoimidazol-1-yl]-2-cyclohexyl-ethoxy}-isonicotinic acid methyl ester The title compound was prepared in analogy to Example 35 from 1-(2-bromo-1-cyclohexyl-ethyl)-2-(4-chloro-phenyl)-5,6-difluoro-1H-benzoimidazole (Ex. 34, int.) and methyl 2-hydroxypyridine-4-carboxylate after a reaction time of 4 days at room temperature and using a gradient of n-heptane:ethyl acetate of 100:0 to 70:30. Light yellow solid (19%). MS: (Turbo Spray): m/z=526.2 [M+H].

Example 38

2-(4-Chloro-phenyl)-1-(1-cyclohexyl-2-phenoxyethyl)-5,6-difluoro-1H-benzoimidazole To a solution of 0.2 g (0.51 mmol) 2-[2-(4-chloro-phenyl)-5,6-difluoro-benzoimidazol-1-yl]-2-cyclohexyl-ethanol (Ex. 1, int. c) in 4 mL tetrahydrofuran were added 53 mg (0.56 mmol) phenol and 124 mg (0.61 mmol) tri-n-butylphosphin. The reaction mixture was cooled down to 0° C. and 106 mg (0.61 mmol) N,N,N',N'-tetramethylazodicarboxamide were added. After stirring for 18 h at room temperature the reaction mixture was evaporated. The residue was purified by silica gel chromatography using a MPLC system (CombiFlash Companion, Isco Inc.) with a gradient of n-heptane:Ethyl acetate (100:0 to 60:40). MS (Turbo Spray): m/z=467.2 [M+H].

Example 39

4-{2-[2-(4-Chloro-phenyl)-5,6-difluoro-benzoimidazol-1-yl]-2-cyclohexyl-ethoxy}-3-trifluoromethyl-benzoic acid The title compound was prepared in analogy to Example 4, from 4-{2-[2-(4-chloro-phenyl)-5,6-difluoro-benzoimidazol-1-yl]-2-cyclohexyl-ethoxy}-3-trifluoromethyl-benzoic acid methyl ester. The white solid was purified by silica chromatography using a MPLC system (CombiFlash Companion, Isco Inc.) eluting with a gradient of n-heptane:ethyl acetate (100:0 to 0:100) followed by ethyl acetate:methanol (100:0 to 50:50). White solid (45%). MS (Turbo Spray): m/z=576.9 [M−H].

Intermediate

4-{2-[2-(4-Chloro-phenyl)-5,6-difluoro-benzoimidazol-1-yl]-2-cyclohexyl-ethoxy}-3-trifluoromethyl-benzoic acid methyl ester The title compound was prepared in analogy to Example 26, intermediate, from 2-[2-(4-chloro-phenyl)-5,6-difluoro-benzoimidazol-1-yl]-2-cyclohexyl-ethanol (Ex. 1, int. c) and 4-chloro-3-trifluoromethyl-benzoic acid methyl ester (commercially available) after a reaction time of 6 h and using a gradient of n-heptane:Ethyl acetate (100:0 to 60:40). White solid (32%). MS (Turbo Spray): m/z=493.3 [M+H].

Examples 40 and 41

The title compounds were obtained by separation of the stereoisomers of 4-{2-[2-(4-chloro-phenyl)-5,6-difluoro-benzoimidazol-1-yl]-2-cyclohexyl-ethoxy}-3-trifluoromethyl-benzoic acid (Ex. 38) by chiral preparative HPLC (Chiralpak AD) eluting with a mixture of n-heptane/10% ethanol (containing 0.5% formic acid).

(+)-4-{2-[2-(4-Chloro-phenyl)-5,6-difluoro-benzoimidazol-1-yl]-2-cyclohexyl-ethoxy}-3-trifluoromethyl-benzoic acid White solid. MS (Turbo Spray): m/z=576.9 [M−H].

(−)-4-{2-[2-(4-Chloro-phenyl)-5,6-difluoro-benzoimidazol-1-yl]-2-cyclohexyl-ethoxy}-3-trifluoromethyl-benzoic acid White solid. MS (Turbo Spray): m/z=576.9 [M−H].

Example 42

4-{2-[2-(4-Chloro-phenyl)-5,6-difluoro-benzoimidazol-1-yl]-2-cyclohexyl-ethoxy}-2,6-difluoro-benzoic acid The title compound was prepared in analogy to Example 4, from 4-{2-[2-(4-chloro-phenyl)-5,6-difluoro-benzoimidazol-1-yl]-2-cyclohexyl-ethoxy}-2,6-difluoro-benzoic acid methyl ester. The white solid was purified by silica gel chromatography using a MPLC system (CombiFlash Companion, Isco Inc.) eluting with a gradient of n-heptane:ethyl acetate (100:0 to 0:100) followed by ethyl acetate:methanol (100:0 to 50:50). White solid (45%). MS (Turbo Spray): m/z=547.3 [M−H].
Intermediates a) 4-{2-[2-(4-Chloro-phenyl)-5,6-difluoro-benzoimidazol-1-yl]-2-cyclohexyl-ethoxy}-2,6-difluoro-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 2,6-difluoro-4-hydroxy-benzoic acid methyl ester and replacing di-ethyl azodicarboxylate by di-tert-butyl azodicarboxylate. Light yellow oil (85%). MS (Turbo Spray): m/z=561.2 [M+H].

b) 2,6-Difluoro-4-hydroxy-benzoic acid methyl ester

The title compound was prepared in analogy to Ex. 16, intermediate b, from 2,6-difluoro-4-hydroxy-benzoic acid (commercially available). MS (Turbo Spray): m/z=189.1 [M+H].

Examples 43 and 44

The title compounds were obtained by separation of the stereoisomers of 4-{2-[2-(4-chloro-phenyl)-5,6-difluoro-benzoimidazol-1-yl]-2-cyclohexyl-ethoxy}-2,6-difluoro-benzoic acid (Example 42) by chiral preparative HPLC (Chiralpak AD) eluting with n-heptane/10% ethanol (containing 0.5% formic acid).

(+)-4-{2-[2-(4-Chloro-phenyl)-5,6-difluoro-benzoimidazol-1-yl]-2-cyclohexyl-ethoxy}-2,6-difluoro-benzoic acid White solid. MS (Turbo Spray): m/z=547.3 [M+H].

(−)-4-{2-[2-(4-Chloro-phenyl)-5,6-difluoro-benzoimidazol-1-yl]-2-cyclohexyl-ethoxy}-2,6-difluoro-benzoic acid White solid. MS (Turbo Spray): m/z=547.3 [M+H].

Example 45

(6-{2-[2-(4-Chloro-phenyl)-5,6-difluoro-benzoimidazol-1-yl]-2-cyclohexyl-ethoxy}-pyridin-3-yloxy)-acetic acid To a solution of 0.18 g (0.32 mmol) (6-{2-[2-(4-chloro-phenyl)-5,6-difluoro-benzoimidazol-1-yl]-2-cyclohexyl-ethoxy}-pyridin-3-yloxy)-acetic acid ethyl ester in 2 mL tetrahydrofuran 2 mL water and 0.13 mL (0.77 mmol) 32% aqueous sodium hydroxide solution were added. The mixture was stirred at 75° C. for 1.5 h and then poured on 20 mL 1M aqueous hydrochloric acid. The aqueous layer was extracted three times with ethyl acetate. The combined organic layers were washed with water and brine, dried over magnesium sulfate and evaporated to dryness. The residue was suspended in a mixture of acetonitrile and water, filtered and washed with acetonitrile to give the desired product as a white solid (61%). MS (Turbo Spray): m/z=542.3 [M+H].
Intermediates a) (6-{2-[2-(4-Chloro-phenyl)-5,6-difluoro-benzoimidazol-1-yl]-2-cyclohexyl-ethoxy}-pyridin-3-yloxy)-acetic acid ethyl ester The title compound was prepared in analogy to Example 4, intermediate, from 2-[2-(4-chloro-phenyl)-benzoimidazol-1-yl]-2-cyclohexyl-ethanol (Ex. 1, intermediate c) and (6-hydroxy-pyridin-3-yloxy)-acetic acid ethyl ester and replacing di-ethyl azodicarboxylate by di-tert-butyl azodicarboxylate. The resulting solid was purified by silica gel chromatography using a MPLC system (CombiFlash Companion, Isco Inc.) eluting with a gradient of heptane and tert-butyl methyl ether (100:0 to 70:30) to give the desired compound as a yellow oil (60%). MS (Turbo Spray): m/z=570.4 [M+H].

b) (6-Hydroxy-pyridin-3-yloxy)-acetic acid ethyl ester

The suspension of 0.64 g (2.23 mmol) (6-benzyloxy-pyridin-3-yloxy)-acetic acid ethyl ester and 0.064 g 10% palladium on charcoal was hydrogenated for 1 h at 1.7 bar. The reaction mixture was filtered over Dicalite Speed Plus, washed with ethanol and the filtrate was treated with silica gel and evaporated. The residue was purified by silica gel chromatography using a MPLC system (CombiFlash Companion, Isco Inc.) with a gradient from heptane:ethyl acetate (100:0 to 0:100) followed by ethyl acetate:methanol (100:0 to 50:50) to give the product as a colorless solid (91%). MS (Turbo Spray): m/z=198.0 [M+H].

c) (6-Benzyloxy-pyridin-3-yloxy)-acetic acid ethyl ester

To an ice-cold solution of 0.5 g (2.5 mmol) 6-benzyloxy-3-hydroxypyridine (commercially available) in 5 mL tetrahydrofuran 0.12 g (2.7 mmol) sodium hydride (55% dispersion in mineral oil) was added. After the vigorous gas evolution had ceased the reaction mixture was stirred for 15 min. and then 0.41 mL (3.72 mmol) ethyl bromoacetate were added dropwise. The light brown suspension was stirred for 1 h at room temperature, poured on water and extracted three times with ethyl acetate. The organic layers were washed with brine, dried over magnesium sulfate, filtered, treated with silica gel and evaporated. The resulting solid is purified by silica gel chromatography using a MPLC system (Combi-Flash Companion, Isco Inc.) with a gradient of heptane:ethyl acetate (100:0 to 70:30) to give the desired product as a colorless oil (90%). MS (Turbo Spray): m/z=288.0 [M+H].

Example 46

4-{2-Cyclohexyl-2-[2-(2,6-dimethoxy-pyridin-3-yl)-5,6-difluoro-benzoimidazol-1-yl]-ethoxy}-3-fluoro-benzoic acid The title compound was prepared in analogy to Example 4, from 4-{2-cyclohexyl-2-[2-(2,6-dimethoxy-pyridin-3-yl)-5,6-difluoro-benzoimidazol-1-yl]-ethoxy}-3-fluoro-benzoic acid methyl ester. White solid (97%). MS (Turbo Spray): m/z=554.2 [M−H].
Intermediate 4-{2-Cyclohexyl-2-[2-(2,6-dimethoxy-pyridin-3-yl)-5,6-difluoro-benzoimidazol-1-yl]-ethoxy}-3-fluoro-benzoic acid methyl ester The title compound was prepared in analogy to Example 4, intermediate, from 2-[2-(4-chloro-phenyl)-benzoimidazol-1-yl]-2-cyclohexyl-ethanol (Ex. 1, int. c) and 3-fluoro-4-hydroxy benzoic acid methyl ester (commercially available), replacing di-ethyl azodicarboxylate by di-tert-butyl azodicarboxylate and a reaction time of 18 h. The residue was purified by silica gel chromatography using a MPLC system (CombiFlash Companion, Isco Inc.) eluting with a gradient of n-heptane:ethyl acetate (100:0 to 60:40) to give the product as a white solid (58%). MS (Turbo Spray): m/z=570.4 [M+H].

Example 47

2-(6-{2-[2-(4-Chloro-phenyl)-5,6-difluoro-benzoimidazol-yl]-2-cyclohexyl-ethoxy}-pyridin-3-yloxy)-2-methyl-propionic acid The title compound was prepared in analogy to Example 43, from 2-(6-{2-[2-(4-Chloro-phenyl)-5,6-difluoro-benzoimidazol-1-yl]-2-cyclohexyl-ethoxy}-pyridin-3-yloxy)-2-methyl-propionic acid ethyl ester. The crude product was purified on a Phenomenex Gemini HPLC preparative column (acetonitrile:water (with 0.5% formic acid) 50:50 to 98:2) to give the desired compound as a white foam (70%). MS (Turbo Spray): m/z=570.3 [M+H].
Intermediates a) 2-(6-{2-[2-(4-Chloro-phenyl)-5,6-difluoro-benzoimidazol-yl]-2-cyclohexyl-ethoxy}-pyridin-3-yloxy)-2-methyl-propionic acid ethyl ester The title compound was prepared in analogy to Example 4, intermediate, from 2-[2-(4-chloro-phenyl)-benzoimidazol-1-yl]-2-cyclohexyl-ethanol (Ex. 1, int. c) and 2-(6-hydroxy-pyridin-3-yloxy)-2-methyl-propionic acid ethyl ester, replacing di-ethyl azodicarboxylate by di-tert-butyl azodicarboxylate and a reaction time of 72 h. The residue was purified by silica gel chromatography using a MPLC system (CombiFlash Companion, Isco Inc.) eluting with a gradient of n-heptane:tert-butyl methyl ether (100:0 to 50:50) to give the product as a yellow foam (84%). MS (Turbo Spray): m/z=598.3 [M+H].

b) 2-(6-Hydroxy-pyridin-3-yloxy)-2-methyl-propionic acid ethyl ester

To a solution of 0.29 g (0.92 mmol) 2-(6-benzyloxy-pyridin-3-yloxy)-2-methyl-propionic acid ethyl ester in 3 mL ethanol 29 mg 10% palladium on charcoal was added. The suspension was hydrogenated at 1.5 bar for 0.75 h. The catalyst was filtered off over Dicalite Speed Plus, washed with ethanol and the filtrate evaporated to dryness to give the desired compound as a light brown solid (94%). MS (Turbo Spray): m/z=226.1 [M+H].

c) 2-(6-Benzyloxy-pyridin-3-yloxy)-2-methyl-propionic acid ethyl ester

To an ice-cold solution of 0.5 g (2.48 mmol) 6-benzyloxy-3-hydroxypyridine (commercially available) in 5 mL tetrahydrofuran 0.12 g (2.7 mmol) sodium hydride (55% dispersion in mineral oil) was added in portions. After the vigorous gas evolution had ceased the reaction mixture was stirred for another 20 min., then 0.44 mL (3.0 mmol) ethyl-alpha-bromoisobutyrate (commercially available) were added dropwise. The light brown suspension was stirred for 23 h at room temperature and then poured into water. The aqueous phase was extracted three times with ethyl acetate and the combined organic layers were washed with brine, dried over magnesium sulfate and filtered. Silica gel was added to the filtrate and the slurry evaporated. The resulting solid is purified by silica gel chromatography using a MPLC system (CombiFlash Companion, Isco Inc.) eluting with a gradient of heptane:ethyl acetate (100:0 to 70:30) to give the product as a colorless oil (38%). MS (Turbo Spray): m/z=316.1 [M+H].

Examples 48 and 49

The title compounds were obtained by separation of the stereoisomers of 2-(6-{2-[2-(4-chloro-phenyl)-5,6-difluoro-benzoimidazol-1-yl]-2-cyclohexyl-ethoxy}-pyridin-3-yloxy)-2-methyl-propionic acid (Example 47) by chiral preparative HPLC (Chiralpak AD) eluting with n-heptane/15% ethanol (containing 0.5% formic acid).

(+)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid White solid. MS (Turbo Spray): m/z=570.3 [M+H].

(−)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid White solid. MS (Turbo Spray): m/z=570.3 [M+H].

Example 50

1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid The title compound was prepared in analogy to Example 43, from 1-(6-{2-[2-(4-chloro-phenyl)-5,6-difluoro-benzoimidazol-1-yl]-2-cyclohexyl-ethoxy}-pyridin-3-yloxy)-cyclopropanecarboxylic acid methyl ester. The crude product was purified on a Phenomenex Gemini HPLC preparative column (acetonitrile:water (with 0.5% formic acid) 50:50 to 98:2) to give the desired compound as a white solid (62%). MS (Turbo Spray): m/z=568.3 [M+H].
Intermediates a) 1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid methyl ester The title compound was prepared in analogy to Example 4, intermediate, from 2-[2-(4-chloro-phenyl)-benzoimidazol-1-yl]-2-cyclohexyl-ethanol (Ex. 1, int. c) and 1-(6-hydroxy-pyridin-3-yloxy)-cyclopropanecarboxylic acid methyl ester, replacing di-ethyl azodicarboxylate by di-tert-butyl azodicarboxylate and a reaction time of 72 h. The residue was purified by silica gel chromatography using a MPLC system (CombiFlash Companion, Isco Inc.) eluting with a gradient of n-heptane:tert-butyl methyl ether (100:0 to 50:50) to give the product as a yellow foam (74%). MS (Turbo Spray): m/z=582.1 [M+H].

b) 1-(6-Hydroxy-pyridin-3-yloxy)-cyclopropanecarboxylic acid methyl ester

To a solution of 0.39 g (1.3 mmol) 1-(6-benzyloxy-pyridin-3-yloxy)-cyclopropanecarboxylic acid methyl ester in 4 mL ethanol, 39 mg 10% palladium on charcoal was added. The suspension was hydrogenated at 1.5 bar for 1 h. The catalyst was filtered off over Dicalite Speed Plus, washed with ethanol and the filtrate evaporated to dryness to the desired compound as a light brown solid (97%). MS (Turbo Spray): m/z=210.1 [M+H].

c) 1-(6-Benzyloxy-pyridin-3-yloxy)-cyclopropanecarboxylic acid methyl ester

The solution of 0.55 g (1.45 mmol) 2-(6-benzyloxy-pyridin-3-yloxy)-4-bromo-butyric acid methyl ester in 8 mL tetrahydrofuran was cooled to 0° C. and 0.17 g (1.5 mmol) potassium tert-butoxide were added. The resulting pale yellow solution was stirred for 3 h at room temperature and then poured onto water. The aqueous phase was extracted three times with ethyl acetate and the organic layers were washed with brine, dried over magnesium sulfate, filtered and evaporated to give the product as a colorless oil (92%) which was pure enough for the next step. MS (Turbo Spray): m/z=210.1 [M+H].

d) 2-(6-Benzyloxy-pyridin-3-yloxy)-4-bromo-butyric acid methyl ester

To an ice-cold solution of 0.5 g (2.5 mmol) 6-benzyloxy-3-hydroxypyridine (commercially available) in 5 mL tetrahydrofuran, 0.12 g (2.7 mmol) sodium hydride (55% dispersion in mineral oil) was added portion wise. After vigorous gas evolution had ceased, the reaction mixture was stirred for another 20 min. at 0° C. and then 0.44 mL (3.1 mmol) 2,4-dibromobutyrate (commercially available) were added dropwise. The light brown suspension was stirred for 23 h at room temperature and then poured onto water. The aqueous phase was extracted three times with ethyl acetate and the combined organic layers were washed with brine, dried over magnesium sulfate and filtered. To the filtrate silica gel was added and the slurry evaporated. The resulting solid was purified by silica gel chromatography using a MPLC system (CombiFlash Companion, Isco Inc.) eluting with a gradient of n-heptane:ethyl acetate (100:0 to 70:30) to give the product as a colorless oil (59%). MS (Turbo Spray): m/z=382.1 [M+H].

Examples 51 and 52

The title compounds were obtained by separation of the stereoisomers of 1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid (Example 50) by chiral preparative HPLC (Chiralpak AD) eluting with n-heptane/15% ethanol (containing 0.5% formic acid).

(−)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid White solid. MS (Turbo Spray): m/z=568.3 [M+H].

(+)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid White solid. MS (Turbo Spray): m/z=568.3 [M+H].

Example 53

4-{2-[2-(4-Chloro-phenyl)-5,6-difluoro-benzoimidazol-1-yl]-2-cyclohexyl-ethoxy}-3,5-dimethyl-benzoic acid The title compound was prepared in analogy to Example 4, from 4-{2-[2-(4-chloro-phenyl)-5,6-difluoro-benzoimidazol-1-yl]-2-cyclohexyl-ethoxy}-3,5-dimethyl-benzoic acid methyl ester to give the title compound as a white solid (94%). MS (Turbo Spray): m/z=539.4 [M+H].
Intermediate 4-{2-[2-(4-Chloro-phenyl)-5,6-difluoro-benzoimidazol-1-yl]-2-cyclohexyl-ethoxy}-3,5-dimethyl-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), 4-hydroxy-3,5-dimethyl-benzoic acid methyl ester and replacing di-ethyl azodicarboxylate by di-tert-butyl azodicarboxylate and a reaction time of 18 h. Light yellow solid (12%). MS (Turbo Spray): m/z=553.3 [M+H].

Examples 54 and 55

The title compounds were obtained by separation of the stereoisomers of 4-{2-[2-(4-chloro-phenyl)-5,6-difluoro-benzoimidazol-1-yl]-2-cyclohexyl-ethoxy}-3,5-dimethyl-benzoic acid methyl ester (Ex. 53) by chiral preparative HPLC (Chiralpak AD) eluting with n-heptane/10% ethanol (containing 0.5% formic acid).

(+)-4-{2-[2-(4-Chloro-phenyl)-5,6-difluoro-benzoimidazol-1-yl]-2-cyclohexyl-ethoxy}-3,5-dimethyl-benzoic acid White solid. MS (Turbo Spray): m/z=539.4 [M+H].

(−)-4-{2-[2-(4-Chloro-phenyl)-5,6-difluoro-benzoimidazol-1-yl]-2-cyclohexyl-ethoxy}-3,5-dimethyl-benzoic acid White solid. MS (Turbo Spray): m/z=539.4 [M+H].

Example 56

2-(4-Chloro-phenyl)-1-{1-cyclohexyl-2-[5-(1H-tetrazol-5-yl)-pyridin-2-yloxy]-ethyl}-5,6-difluoro-1H-benzoimidazole To a solution of 0.15 g (0.30 mmol) 6-{2-[2-(4-chlorophenyl)-5,6-difluoro-benzoimidazol-1-yl]-2-cyclohexylethoxy}-nicotinonitrile in 4 ml o-xylene were added 99 mg (1.52 mmol) sodium azide and 209 mg (1.52 mmol) triethylamine hydrochloride. The reaction mixture was stirred for 2 hours at 145° C. The reaction mixture was poured on 20 ml 1N aqueous hydrochloric acid in water and 20 ml ethyl acetate and the layers were separated. The aqueous layer was extracted with 20 ml ethyl acetate, the combined organic layers were washed again with ml 1N aqueous hydrochloric acid in water and 20 ml brine, dried with magnesium sulfate, filtered and concentrated under vacuum. The residue was suspended in 3 ml acetonitrile, stirred for 30 minutes at room temperature and filtered. White solid (80%). MS (Turbo Spray): m/z=536.2 [M+H].
Intermediate a) 6-{2-[2-(4-Chloro-phenyl)-5,6-difluoro-benzoimidazol-1-yl]-2-cyclohexyl-ethoxy}-nicotinonitrile The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), 3-cyano-6-hydroxy-pyridine and replacing di-ethyl azodicarboxylate by di-tert-butyl azodicarboxylate and a reaction time of 18 h. Light yellow solid (41%). MS (Turbo Spray): m/z=493.2 [M+H].

Example 57

4-{2-[2-(4-Chloro-phenyl)-5,6-difluoro-benzoimidazol-1-yl]-2-cyclohexyl-1,1-dimethyl-ethoxymethyl}-benzoic acid The title compound was prepared in analogy to Example 4, from 4-{2-[2-(4-chloro-phenyl)-5,6-difluoro-benzoimidazol-1-yl]-2-cyclohexyl-1,1-dimethyl-ethoxymethyl}-benzoic acid methyl ester to give the desired compound as a white solid (68%). MS (Turbo Spray): m/z=553.2 [M+H].
Intermediates a) 1-[2-(4-Chloro-phenyl)-5,6-difluoro-benzoimidazol-1-yl]-1-cyclohexyl-2-methyl-propan-2-ol To a solution of 3.0 g (6.93 mmol) [2-(4-chloro-phenyl)-5,6-difluoro-benzoimidazol-1-yl]-cyclohexyl-acetic acid ethyl ester (Example 1, intermediate b) in 50 ml tetrahydrofuran were added dropwise 8.1 ml (24.3 mmol) methylmagnesium bromide (3M solution in diethyl ether). During the addition a yellowish solution formed, which became slightly warm. After 23 h the light yellow solution was poured onto 300 ml aqueous saturated potassium sodium tartrate solution and was extracted three times with ethyl acetate. The combined organic layers were washed with water and brine, dried over magnesium sulfate, filtered, and evaporated until a suspension has formed. This light yellow suspension was filtered and washed with a small amount of ice-cold ethyl acetate. The resulting white solid (2.4 g, 84%) was pure enough for the next step. MS (Turbo Spray): m/z=419.2 [M+H].

b) 4-{2-[2-(4-Chloro-phenyl)-5,6-difluoro-benzoimidazol-1-yl]-2-cyclohexyl-1,1-dimethyl-ethoxymethyl}-benzoic acid methyl ester The title compound was prepared in analogy to Example 26, intermediate, from 1-[2-(4-chloro-phenyl)-5,6-difluoro-benzoimidazol-1-yl]-1-cyclohexyl-2-methyl-propan-2-ol and methyl 4-(bromomethyl)benzoate (commercially available) to give the desired compound as a white solid (12%). MS (Turbo Spray): m/z=567.3 [M+H].

Example 58

4-{2-[2-(4-Chloro-phenyl)-5,6-difluoro-benzoimidazol-1-yl]-2-cyclohexyl-ethoxymethyl}-benzoic acid The title compound was prepared in analogy to Example 4, from 4-{2-[2-(4-chloro-phenyl)-5,6-difluoro-benzoimidazol-1-yl]-2-cyclohexyl-ethoxymethyl}-benzoic acid methyl ester to give the desired product as a white solid (97%). MS (Turbo Spray): m/z=525.1 [M+H].
Intermediate 4-{2-[2-(4-Chloro-phenyl)-5,6-difluoro-benzoimidazol-1-yl]-2-cyclohexyl-ethoxymethyl}-benzoic acid methyl ester The title compound was prepared in analogy to Example 26, intermediate, from 2-[2-(4-chloro-phenyl)-5,6-difluoro-benzoimidazol-1-yl]-2-cyclohexyl-ethanol (Example 1, intermediate c) and methyl (4-bromomethyl)benzoate (commercially available) to give the compound as light yellow solid (64%). MS (Turbo Spray): m/z=539.4 [M+H].

Example 59

4-{2-[2-(4-Chloro-phenyl)-5,6-difluoro-benzoimidazol-1-yl]-2-cyclohexyl-ethoxymethyl}-3-fluoro-benzoic The title compound was prepared in analogy to Example 4, from 4-{2-[2-(4-chloro-phenyl)-5,6-difluoro-benzoimidazol-1-yl]-2-cyclohexyl-ethoxymethyl}-3-fluoro-benzoic methyl ester to give the compound as a white solid (93%). MS (Turbo Spray): m/z=543.3 [M+H].
Intermediate 4-{2-[2-(4-Chloro-phenyl)-5,6-difluoro-benzoimidazol-1-yl]-2-cyclohexyl-ethoxymethyl}-3-fluoro-benzoic methyl ester The title compound was prepared in analogy to Example 26, intermediate, from 2-[2-(4-chloro-phenyl)-5,6-difluoro-benzoimidazol-1-yl]-2-cyclohexyl-ethanol (Example 1, intermediate c) and 4-bromomethyl-3-fluorobenzoic acid methyl ester (commercially available) to give the compound as light yellow solid (34%). MS (Turbo Spray): m/z=557.4 [M+H].

Example 60

4-{2-[2-(4-Chloro-phenyl)-5,6-difluoro-benzoimidazol-1-yl]-2-cyclohexyl-ethoxymethyl}-3-methoxy-benzoic acid The title compound was prepared in analogy to Example 4, from 4-{2-[2-(4-chloro-phenyl)-5,6-difluoro-benzoimidazol-1-yl]-2-cyclohexyl-ethoxymethyl}-3-methoxy-benzoic acid methyl ester to gibe the desired product as a white solid (88%). MS (Turbo Spray): m/z=555.2 [M+H].
Intermediate 4-{2-[2-(4-Chloro-phenyl)-5,6-difluoro-benzoimidazol-1-yl]-2-cyclohexyl-ethoxymethyl}-3-methoxy-benzoic acid methyl ester The title compound was prepared in analogy to Example 26, intermediate, from 2-[2-(4-chloro-phenyl)-5,6-difluoro-benzoimidazol-1-yl]-2-cyclohexyl-ethanol (Example 1, intermediate c) and methyl 4-(bromomethyl)-3-methoxybenzoate (commercially available), to give the compound as light yellow solid (73%). MS (Turbo Spray): m/z=569.4 [M+H].

Example 61

4-{2-[2-(4-Chloro-phenyl)-5,6-difluoro-benzoimidazol-1-yl]-2-cyclohexyl-ethoxy}-2,6-dimethyl-benzoic acid The title compound was prepared in analogy to Example 4, from 4-{2-[2-(4-chloro-phenyl)-5,6-difluoro-benzoimidazol-1-yl]-2-cyclohexyl-ethoxy}-2,6-dimethyl-benzoic acid methyl ester. White solid (27%). MS (Turbo Spray): m/z=539.3 [M–H].
Intermediate 4-{2-[2-(4-Chloro-phenyl)-5,6-difluoro-benzoimidazol-1-yl]-2-cyclohexyl-ethoxy}-2,6-dimethyl-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 4-hydroxy-2,6-dimethyl-benzoic acid methyl ester (commercially available) and replacing di-ethyl azodicarboxylate by di-tert-butyl azodicarboxylate. The resulting solid was purified by silica gel chromatography using a MPLC system (CombiFlash Companion, Isco Inc.) eluting with a gradient of n-heptane and ethyl acetate (100:0 to 60:40) to give the desired compound as a light yellow solid (12%). MS (Turbo Spray): m/z=553.3 [M+H].

Examples 62 and 63

The title compounds were obtained by separation of the stereoisomers of 2-(4-chloro-phenyl)-1-{1-cyclohexyl-2-[5-(1H-tetrazol-5-yl)-pyridin-2-yloxy]-ethyl}-5,6-difluoro-1H-benzoimidazole (Example 56) by chiral preparative HPLC (Chiralpak AD) eluting with n-heptane/15% ethanol (containing 0.5% formic acid).

(+)-2-(4-Chloro-phenyl)-1-{1-cyclohexyl-2-[5-(1H-tetrazol-5-yl)-pyridin-2-yloxy]-ethyl}-5,6-difluoro-1H-benzoimidazole MS (Turbo Spray): m/z=567.9 [M–H].

(–)-2-(4-Chloro-phenyl)-1-{1-cyclohexyl-2-[5-(1H-tetrazol-5-yl)-pyridin-2-yloxy]-ethyl}-5,6-difluoro-1H-benzoimidazole MS (Turbo Spray): m/z=576.9 [M–H].

Examples 64 and 65

The title compounds were obtained by separation of the stereoisomers of 4-{2-[2-(4-chloro-phenyl)-5,6-difluoro-benzoimidazol-1-yl]-2-cyclohexyl-ethoxymethyl}-3-fluoro-benzoic (Example 56) by chiral preparative HPLC (Chiralpak AD) eluting with n-heptane/10% ethanol (containing 0.5% formic acid).

(+)-4-{2-[2-(4-Chloro-phenyl)-5,6-difluoro-benzoimidazol-yl]-2-cyclohexyl-ethoxymethyl}-3-fluoro-benzoic MS (Turbo Spray): m/z=543.3 [M+H].

(–)-4-{2-[2-(4-Chloro-phenyl)-5,6-difluoro-benzoimidazol-yl]-2-cyclohexyl-ethoxymethyl}-3-fluoro-benzoic MS (Turbo Spray): m/z=543.3 [M+H].

Example 66

2-(4-Chloro-phenyl)-1-{1-cyclohexyl-2-[2-fluoro-4-(1H-tetrazol-5-yl)-phenoxy]-ethyl}-5,6-difluoro-1H-benzoimidazole The title compound was prepared in analogy to Example 56 from 4-{2-[2-(4-chloro-phenyl)-5,6-difluoro-benzoimidazol-1-yl]-2-cyclohexyl-ethoxy}-3-fluoro-benzonitrile. White solid (53%). MS (Turbo Spray): m/z=553.2 [M+H].
Intermediate 4-{2-[2-(4-Chloro-phenyl)-5,6-difluoro-benzoimidazol-1-yl]-2-cyclohexyl-ethoxy}-3-fluoro-benzonitrile The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c) and 3-fluoro-4-hydroxybenzonitrile (commercially available) and replacing di-ethyl azodicarboxylate by di-tert-butyl azodicarboxylate. The resulting solid was purified by silica gel chromatography using a MPLC system (CombiFlash Companion, Isco Inc.) eluting with a gradient of n-heptane and ethyl acetate (100:0 to 50:50) to give the desired compound as a colorless foam (89%). MS (Turbo Spray): m/z=510.3 [M+H].

Example 67

6-{2-[2-(4-Chloro-phenyl)-5,6-difluoro-benzoimidazol-1-yl]-2-cyclohexyl-ethoxymethyl}-nicotinic acid The title compound was prepared in analogy to Example 4, from 6-{2-[2-(4-chloro-phenyl)-5,6-difluoro-benzoimidazol-1-yl]-2-cyclohexyl-ethoxymethyl}-nicotinic acid methyl ester to give the title compound as a light yellow solid (16%). MS (Turbo Spray): m/z=526.2 [M+H].

Intermediate

6-{2-[2-(4-Chloro-phenyl)-5,6-difluoro-benzoimidazol-1-yl]-2-cyclohexyl-ethoxymethyl}-nicotinic acid methyl ester The title compound was prepared in analogy to Example 26, from 2-[2-(4-chloro-phenyl)-5,6-difluoro-benzoimidazol-1-yl]-2-cyclohexyl-ethanol (Ex. 1, int. c) and 6-chloromethyl-nicotinic acid methyl ester (commercially available) to give the title compound after purification by silica gel chromatography using a MPLC system (CombiFlash Companion, Isco Inc.) eluting with a gradient of n-heptane and ethyl acetate (100:0 to 60:40) as a light yellow solid (10%). MS (Turbo Spray): m/z=540.4 [M+H].

Examples 68 and 69

The title compounds were obtained by separation of the stereoisomers of 4-{2-[2-(4-chloro-phenyl)-5,6-difluoro-benzoimidazol-1-yl]-2-cyclohexyl-ethoxymethyl}-benzoic acid (Example 58) by chiral preparative HPLC (Chiralpak AD) eluting with n-heptane/20% ethanol (containing 0.5% formic acid).

(−)-4-{2-[2-(4-Chloro-phenyl)-5,6-difluoro-benzoimidazol-1-yl]-2-cyclohexyl-ethoxymethyl}-benzoic acid Colorless solid. MS (Turbo Spray): m/z=525.2 [M+H].

(+)-4-{2-[2-(4-Chloro-phenyl)-5,6-difluoro-benzoimidazol-1-yl]-2-cyclohexyl-ethoxymethyl}-benzoic acid Colorless solid. MS (Turbo Spray): m/z=525.2 [M+H].

Example 70

2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole The title compound was prepared in analogy to Example 56 from 4-{2-[2-(4-chloro-phenyl)-5,6-difluoro-benzoimidazol-1-yl]-2-cyclohexyl-ethoxy}-3,5-dimethyl-benzonitrile. White solid (57%). MS (Turbo Spray): m/z=563.5 [M+H].
Intermediate 4-{2-[2-(4-Chloro-phenyl)-5,6-difluoro-benzoimidazol-1-yl]-2-cyclohexyl-ethoxy}-3,5-dimethyl-benzonitrile To an ice-cold solution of 0.38 g (0.97 mmol) 2-[2-(4-chloro-phenyl)-5,6-difluoro-benzoimidazol-1-yl]-2-cyclohexyl-ethanol (Ex. 1, int. c), 0.157 g (1.07 mmol) 3,5-dimethyl-4-hydroxybenzonitrile (commercially available) and 0.29 ml (1.17 mmol) tri-N-butylposphine in 8 ml tetrahydrofuran, 0.20 g (1.17 mmol) N'N'N'N-tetramethylazodicarboxylate were added in one portion. After 48 h stirring at RT another 0.29 ml (1.17 mmol) tri-N-butylposphine and 0.2 g (1.17 mmol) N'N'N'N-tetramethylazodicarboxylate were added. The reaction mixture was stirred at RT for another 5 days, silica gel was added and the suspension evaporated to dryness. The residue was chromatographed three times using a MPLC system (CombiFlash Companion, Isco Inc.) eluting with a gradient of heptane and tert-butyl methyl ether (100:0 to 60:40) to give the desired compound as a light yellow solid (22%). MS (Turbo Spray): m/z=520.3 [M+H].

Examples 71 and 72

The title compounds were obtained by separation of the stereoisomers of 2-(4-chloro-phenyl)-1-{1-cyclohexyl-2-[2,6-dimethyl-4-(1H-tetrazol-5-yl)-phenoxy]-ethyl}-5,6-difluoro-1H-benzoimidazole (Example 70) by chiral preparative HPLC (Reprosil Chiral NR) eluting with n-heptane:ethanol (with 0.01M ammonium acetate) 66:35.

(−)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole Light brown solid. MS (Turbo Spray): m/z=563.5 [M−H].

(+)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole Light brown solid. MS (Turbo Spray): m/z=563.4 [M−H].

Example 73

6-{2-Cyclohexyl-2-[2-(2,6-dimethoxy-pyridin-3-yl)-5,6-difluoro-benzoimidazol-1-yl]-ethoxy}-nicotinic acid The title compound was prepared in analogy to Example 4, from 6-{2-cyclohexyl-2-[2-(2,6-dimethoxy-pyridin-3-yl)-5,6-difluoro-benzoimidazol-1-yl]-ethoxy}-nicotinic acid methyl ester. Colorless solid (51%). MS (Turbo Spray): m/z=539.3 [M+H].
Intermediates a) 6-{2-Cyclohexyl-2-[2-(2,6-dimethoxy-pyridin-3-yl)-5,6-difluoro-benzoimidazol-1-yl]-ethoxy}-nicotinic acid methyl ester The title compound was prepared in analogy to Example 4, intermediate from 2-cyclohexyl-2-[2-(2,6-dimethoxy-pyridin-3-yl)-5,6-difluoro-benzoimidazol-1-yl]-ethanol and methyl 6-hydroxynicotinate (commercially available) and replacing di-ethyl azodicarboxylate by di-tert-butyl azodicarboxylate. The crude product was purified by silica gel chromatography using a MPLC system (CombiFlash Companion, Isco Inc.) eluting with a gradient of n-heptane:ethyl acetate (100:0 to 60:40) to give the desired compound as a white solid (4%). MS (Turbo Spray) m/z=553.4 [M+H].

b) 2-Cyclohexyl-2-[2-(2,6-dimethoxy-pyridin-3-yl-5,6-difluoro-benzoimidazol-1-yl]-ethanol To a solution of 5.3 g (11.9 mmol) cyclohexyl-[2-(2,6-dimethoxy-pyridin-3-yl)-5,6-difluoro-benzoimidazol-1-yl]-acetic acid methyl ester in 75 ml dry tetrahydrofuran was added 0.474 g (12.49 mmol) lithium aluminum hydride at 0° C. The reaction mixture was stirred for 2 h at room temperature. The reaction mixture was poured on 300 ml 10% aqueous sodium potassium tartrate and 300 ml ethyl acetate and the phases were separated. The aqueous layer was extracted again with 300 ml ethyl acetate. The combined organic layers were washed with 300 ml brine, dried over magnesium sulfate, filtered and evaporated. The residue was purified by silica gel chromatography using a MPLC system (Combi- Flash Companion, Isco Inc.) eluting with a gradient of n-heptane:ethyl acetate (2:1) to give the desired compound as a yellow foam. MS (Turbo Spray): 418.2 [M+H].

c) Cyclohexyl-[2-(2,6-dimethoxy-pyridin-3-yl)-5,6-difluoro-benzoimidazol-1-yl]-acetic acid methyl ester To a solution of 5.86 g (13.58 mmol) cyclohexyl-[2-(2,6-dimethoxy-pyridin-3-yl)-5,6-difluoro-benzoimidazol-1-yl]-acetic acid in 60 ml N,N-dimethylformamide was added 652 mg (14.94 mmol) sodium hydride (55% dispersion in mineral oil) and 2.02 g (14.26 mmol) methyl iodide. The reaction mixture was poured on 300 ml water and 300 ml ethyl acetate and the phases were separated. The aqueous layer was extracted a second time with 300 ml ethyl acetate. The combined organic layers were washed twice with 300 ml water and once with 300 ml brine, dried over magnesium sulfate, filtered and concentrated. The residue was purified by silica gel chromatography using a MPLC system (CombiFlash Companion, Isco Inc.) eluting with a gradient of n-heptane:ethyl acetate (100:0 to 60:40). Light yellow solid (88%). MS (Turbo Spray) m/z=446.3 [M+H].

d) Cyclohexyl-[2-(2,6-dimethoxy-pyridin-3-yl)-5,6-difluoro-benzoimidazol-1-yl]-acetic acid To a suspension of 12.1 g (22.02 mmol) N-benzyl-N-nitroso-2-cyclohexyl-2-[2-(2,6-dimethoxy-pyridin-3-yl)-5,6-difluoro-benzoimidazol-1-yl]-acetamide in 65 ml tetrahydrofuran and 15 ml water were added dropwise over 20 min. a solution of 9.24 g (220 mmol) lithium hydroxide monohydrate in 45 ml (440 mmol) hydrogen peroxide and 30 ml water. The reaction mixture turned into a turbid solution and a slight temperature raise was observed (cooled temporarily using an ice-bath). After 1 h the pH of the mixture was adjusted to pH 4 using acetic acid. The resulting light yellow solution was extracted three times with ethyl acetate. The combined organic layers were washed twice with saturated aqueous sodium bicarbonate solution, once with water and once with brine. The solution was dried over magnesium sulfate, filtered and evaporated. The residue was dissolved in 200 ml tert-butyl methyl ether and partially evaporated until a precipitation formed. The suspension was cooled in the refrigerator for 30 min, then the solid was filtered off, washed with 50 ml ice-cold tert-butyl methyl ether and dried in high vacuum. White solid (99%). MS (Turbo Spray): m/z=432.2 [M+H].

e) N-Benzyl-N-nitroso-2-cyclohexyl-2-[2-(2,6-dimethoxy-pyridin-3-yl)-5,6-difluoro-benzoimidazol-1-yl]-acetamide To an ice-cold solution of 15 g (28.81 mmol) N-benzyl-2-cyclohexyl-2-[2-(2,6-dimethoxy-pyridin-3-yl)-5,6-difluoro-benzoimidazol-1-yl]-acetamide in 94 ml (1642 mmol) acetic acid and 198 ml (3486 mmol) acetic anhydride were added in 5 portions over 30 min. 9.94 g (144 mmol) sodium nitrite. The resulting solution was allowed to warm to room temperature overnight. The resulting yellow suspension was evaporated and the yellow slurry was taken up in 500 ml saturated aqueous sodium bicarbonate solution and 1500 ml ethyl acetate. The aqueous layer was extracted twice with 1500 ml ethyl acetate and once with 500 ml ethyl acetate. The combined organic layers were washed with water and brine. The remaining unsoluble material was filtered off and the filtrate dried over magnesium sulfate, filtered and evaporated until a suspension has formed. This suspensions was filtered and the filter cake washed twice with 50 ml ice-cold ethyl acetate and dried in high vacuum. Light yellow solid. MS (Turbo Spray): m/z=550.3 [M+H].

f) N-Benzyl-2-cyclohexyl-2-[2-(2,6-dimethoxy-pyridin-3-yl)-5,6-difluoro-benzoimidazol-1-yl]-acetamide 10.0 g (40.94 mmol) (2-amino-4,5-difluoro-phenyl)-carbamic acid tert-butyl ester were dissolved in 60 ml methanol, then 5.91 ml (49.13 mmol) cyclohexylcarbaldehyde (commercially available) were added. After stirring for 5 min. at room temperature the solution was treated with 7.50 g (40.94 mmol) 2,6-dimethoxynicotinic acid commercially available), followed by an addition of 5.0 ml (40.94 mmol) benzylisocyanide (commercially available). From the clear, light brown and slightly warm solution a suspension formed within a few minutes. After 3 h another ml methanol were added. After stirring for 20 h, 51.18 ml (205 mmol) of a 1M hydrochloric acid solution in dioxane were added dropwise over 5 min. The resulting solution was stirred at room temperature for 29 h, then poured onto 500 ml saturated aqueous sodium bicarbonate solution and the layers were separated. The aqueous layer was extracted three times with ethyl acetate. The combined organic layers were washed with water and brine, dried over magnesium sulfate, filtered, treated with silica gel and evaporated to dryness. The resulting solid was purified by silica gel chromatography using a MPLC system (Combi-Flash Companion, Isco Inc.) eluting with n-heptane:tert-butyl methyl ether (1:1) as eluant. Off-white foam (72%). MS (Turbo Spray) m/z=521.5 [M+H].

g) (2-Amino-4,5-difluoro-phenyl)-carbamic acid tert-butyl ester

To a solution of di-tert-butyl dicarbonate (14.8 g, 67.8 mmol, 2.0 equiv; [CAS RN 24424-99-5]) and 4-dimethylaminopyridine (0.21 g, 1.7 mmol, 0.05 equiv; DMAP; [CAS RN 1122-58-3]) in tetrahydrofuran (100 mL) was added 4,5-difluoro-2-nitro-phenylamine (5.9 g, 33.9 mmol, 1.0 equiv; [CAS RN 78056-39-0]) and the mixture was stirred at room temperature for 72 h. The solvent was evaporated under reduced pressure and the crude reaction product extracted from a saturated aqueous sodium bicarbonate solution with ethyl acetate. The organic phases were dried over sodium sulfate, the residue taken up in dichloromethane and cooled to 0° C. Trifluoroacetic acid (7.73 g, 67.8 mmol, 2.0 equiv) was added slowly and the reaction mixture stirred at 0° C. for 48 h. A solution of 2M aqueous sodium hydroxide solution was added to adjust the pH of the solution to 7. The organic layer was separated and evaporated under reduced pressure. The residue was taken up in ethyl acetate and the product extracted from an aqueous saturated sodium bicarbonate solution, the organic phase dried over sodium sulfate and the intermediate isolated via silica gel chromatography. The purified product (4.28 g, 15.6 mmol, 1.0 equiv) was dissolved in N,N-dimethylformamide (50 mL) and an aqueous saturated solution of ammonium chloride (13 mL) was added. Zinc powder (5.10 g, 78.0 mmol, 5.0 equiv) was added and the suspension stirred for 30 min at 80° C. and for an additional 2 h at room temperature. The remaining solid was filtered off and the organic layer evaporated. The product was extracted from an aqueous saturated sodium bicarbonate solution with ethyl acetate, the organic layer dried over sodium sulfate and the crude reaction product purified via silica gel chromatography. $^1$H NMR (300 MHz, DMSO): ☐ 1.46 (s, 9H), 5.03 (br s, 2H), 6.65 (dd, =8.2 Hz, J=12.9 Hz, 1H), 7.30 (dd, J=8.9 Hz, J=12.3 Hz, 1H), 8.38 (br s, 1H). MS (ISN): m/z=243.4 [M–H].

Examples 74 and 75

The title compounds were obtained by separation of the stereoisomers of 6-{2-cyclohexyl-2-[2-(2,6-dimethoxy-pyridin-3-yl)-5,6-difluoro-benzoimidazol-1-yl]-ethoxy}-nicotinic acid (Example 73) by chiral preparative HPLC (Chiralpak AD) eluting with n-heptane/10% ethanol (containing 0.5% formic acid).

(+)-6-{2-Cyclohexyl-2-[2-(2,6-dimethoxy-pyridin-3-yl)-5,6-difluoro-benzoimidazol-1-yl]-ethoxy}-nicotinic acid Off-white foam. MS (Turbo Spray): m/z=539.4 [M+H].

(–)-6-{2-Cyclohexyl-2-[2-(2,6-dimethoxy-pyridin-3-yl)-5,6-difluoro-benzoimidazol-1-yl]-ethoxy}-nicotinic acid Off-white foam. MS (Turbo Spray): m/z=539.4 [M+H].

Example 76

3-Chloro-4-{2-[2-(4-chloro-phenyl)-5,6-difluoro-benzoimidazol-1-yl]-2-cyclohexyl-ethoxy}-5-fluoro-benzoic acid The title compound was prepared according to Example 4, from 3-chloro-4-{2-[2-(4-chloro-phenyl)-5,6-difluoro-benzoimidazol-1-yl]-2-cyclohexyl-ethoxy}-5-fluoro-benzoic acid methyl ester. White solid (90%). MS (Turbo Spray): m/z=561.1 [M–H].
Intermediate 3-Chloro-4-{2-[2-(4-chloro-phenyl)-5,6-difluoro-benzoimidazol-1-yl]-2-cyclohexyl-ethoxy}-5-fluoro-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), and 3-chloro-5-fluoro-4-hydroxy-benzoic acid methyl ester (CAS RN 369-15-3) and replacing di-ethyl azodicarboxylate by di-tert-butyl azodicarboxylate. The residue was purified by silica gel chromatography using a MPLC system (CombiFlash Companion, Isco Inc.) eluting with a gradient of n-heptane:ethyl acetate (100:0 to 70:30) to give the desired compound as a colorless foam (74%). MS (Turbo Spray): 577.1 [M+H].

Examples 77 and 78

The title compounds were obtained by separation of the stereoisomers of 3-chloro-4-{2-[2-(4-chloro-phenyl)-5,6-difluoro-benzoimidazol-1-yl]-2-cyclohexyl-ethoxy}-5-fluoro-benzoic acid by chiral preparative HPLC (Chiralpak AD) eluting with n-heptane/10% ethanol (containing 0.5% formic acid).

(–)-3-Chloro-4-{2-[2-(4-chloro-phenyl)-5,6-difluoro-benzoimidazol-1-yl]-2-cyclohexyl-ethoxy}-5-fluoro-benzoic acid White foam. MS (Turbo Spray): m/z=563.1 [M+H].

(+)-3-Chloro-4-{2-[2-(4-chloro-phenyl)-5,6-difluoro-benzoimidazol-1-yl]-2-cyclohexyl-ethoxy}-5-fluoro-benzoic acid White foam. MS (Turbo Spray): m/z=563.1 [M+H].

Example 79

4-(1-{2-[2-(4-Chloro-phenyl)-5,6-difluoro-benzoimidazol-1-yl]-2-cyclohexyl-ethoxy}-ethyl)-benzoic acid The title compound was prepared in analogy to Example 1, from 4-(1-{2-[2-(4-chloro-phenyl)-5,6-difluoro-benzoimidazol-1-yl]-2-cyclohexyl-ethoxy}-ethyl)-benzoic acid methyl ester. Colorless solid (88%). MS (Turbo Spray): m/z=539.3 [M+H].
Intermediate 4-(1-{2-[2-(4-Chloro-phenyl)-5,6-difluoro-benzoimidazol-1-yl]-2-cyclohexyl-ethoxy}-ethyl)-benzoic acid methyl ester The title compound was prepared in analogy to Example 34, from 1-(2-bromo-1-cyclohexyl-ethyl)-2-(4-chloro-phenyl)-5,6-difluoro-1H-benzoimidazole (Example 34, intermediate) and 4-(1-bromo-ethyl)-benzoic acid methyl ester (CAS RN: 16281-97-3). The residue was purified by preparative HPLC chromatography (phenomenex gemini column) eluting with a gradient of water:acetonitrile (100:0 to 5:95). Light yellow foam (22%). MS (Turbo Spray): m/z=553.3 [M+H].

Examples 80 and 81

The title compounds were obtained by separation of the stereoisomers of 2-(4-chloro-phenyl)-1-{1-cyclohexyl-2-[2-fluoro-4-(1H-tetrazol-5-yl)-phenoxy]-ethyl}-5,6-difluoro-1H-benzoimidazole (Example 66) by chiral preparative HPLC (Reprosil Chiral NR) eluting with n-heptane:ethanol (with 0.01M ammonium acetate) 70:30.

(+)-2-(4-Chloro-phenyl)-1-{1-cyclohexyl-2-[2-fluoro-4-(1H-tetrazol-5-yl)-phenoxy]-ethyl}-5,6-difluoro-1H-benzoimidazole White solid. MS (Turbo Spray): m/z=550.9 [M–H].

(–)-2-(4-Chloro-phenyl)-1-{1-cyclohexyl-2-[2-fluoro-4-(1H-tetrazol-5-yl)-phenoxy]-ethyl}-5,6-difluoro-1H-benzoimidazole White solid. MS (Turbo Spray): m/z=551.0 [M–H].

Example 82

4-{2-Cyclohexyl-2-[2-(2,6-dimethoxy-pyridin-3-yl)-5,6-difluoro-benzoimidazol-1-yl]-ethoxy}-3,5-dimethyl-benzoic acid The title compound was prepared according to Example 4, from 4-{2-cyclohexyl-2-[2-(2,6-dimethoxy-pyridin-3-yl)-5, 6-difluoro-benzoimidazol-1-yl]-ethoxy}-3,5-dimethyl-benzoic acid methyl ester. White solid (77%). MS (Turbo Spray): m/z=566.3 [M−H].
Intermediate 4-{2-Cyclohexyl-2-[2-(2,6-dimethoxy-pyridin-3-yl)-5,6-difluoro-benzoimidazol-1-yl]-ethoxy}-3,5-dimethyl-benzoic acid methyl ester The title compound was prepared according to Example 4, intermediate, from 2-cyclohexyl-2-[2-(2,6-dimethoxy-pyridin-3-yl)-5,6-difluoro-benzoimidazol-1-yl]-ethanol (Example 73, intermediate b), 4-hydroxy-3,5-dimethyl-benzoic acid methyl ester (commercially available), tri-N-butylposphine and N'N'N'N-tetramethylazodicarboxamide. The resulting powder was purified by silica gel chromatography using a MPLC system (CombiFlash Companion, Isco Inc.) eluting with a gradient of n-heptane:tert-butyl methyl ether (100:0 to 50:50) to give the desired compound as an off-white solid (27%). MS (Turbo Spray): m/z=580.3 [M+H].

Examples 83 and 84

The title compounds were obtained by separation of the stereoisomers of 4-{2-cyclohexyl-2-[2-(2,6-dimethoxy-pyridin-3-yl)-5,6-difluoro-benzoimidazol-1-yl]-ethoxy}-3,5-dimethyl-benzoic acid by chiral preparative HPLC (Chiralpak AD) eluting with n-heptane/10% ethanol (containing 0.5% formic acid).

(+)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid Colorless solid. MS (Turbo Spray): m/z=566.3 [M+H].

(−)-4-{2-Cyclohexyl-2-[2-(2,6-dimethoxy-pyridin-3-yl)-5,6-difluoro-benzoimidazol-yl]-ethoxy}-3,5-dimethyl-benzoic acid Colorless solid. MS (Turbo Spray): m/z=566.3 [M+H].

Example 85

4-{2-[2-(4-Chloro-phenyl)-5,6-difluoro-benzoimidazol-1-yl]-2-cyclohexyl-ethoxy}-3,5-difluoro-benzoic acid The title compound was prepared according to Example 4, from 4-{2-[2-(4-chloro-phenyl)-5,6-difluoro-benzoimidazol-1-yl]-2-cyclohexyl-ethoxy}-3,5-difluoro-benzoic acid methyl ester. The compound was purified by silica gel chromatography using a MPLC system (CombiFlash Companion, Isco Inc.) eluting with a gradient of n-heptane:ethyl acetate:methanol (100:0:0 to 0:100:0 to 0:50:50) to give the desired compound as a colorless solid (68%). MS (Turbo Spray): m/z=547.2 [M+H].
Intermediate 4-{2-[2-(4-Chloro-phenyl)-5,6-difluoro-benzoimidazol-1-yl]-2-cyclohexyl-ethoxy}-3,5-difluoro-benzoic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), 3,5-difluoro-4-hydroxy-benzoic acid methyl ester (commercially available) and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30) to give the desired compound as a light yellow foam (59%). MS (Turbo Spray): m/z=561.2 [M+H].

Examples 86 and 87

The title compounds were obtained by separation of the stereoisomers of 4-{2-[2-(4-chloro-phenyl)-5,6-difluoro-benzoimidazol-1-yl]-2-cyclohexyl-ethoxy}-3,5-difluoro-benzoic acid by chiral preparative HPLC (Chiralpak AD) eluting with n-heptane/15% ethanol (containing 0.5% formic acid).

(−)-4-{2-[2-(4-Chloro-phenyl)-5,6-difluoro-benzoimidazol-1-yl]-2-cyclohexyl-ethoxy}-3,5-difluoro-benzoic acid White solid. MS (Turbo Spray): m/z=547.2 [M+H].

(+)-4-{2-[2-(4-Chloro-phenyl)-5,6-difluoro-benzoimidazol-1-yl]-2-cyclohexyl-ethoxy}-3,5-difluoro-benzoic acid White solid. MS (Turbo Spray): m/z=547.2 [M+H].

Example 88

(−)-2-(4-Chloro-phenyl)-1-{1-cyclohexyl-2-methyl-2-[4-(1H-tetrazol-5-yl)-phenoxy]-propyl}-5,6-difluoro-1H-benzoimidazole The title compound was prepared in analogy to Example 56, from (−)-4-{2-[2-(4-chloro-phenyl)-5,6-difluoro-benzoimidazol-1-yl]-2-cyclohexyl-1,1-dimethyl-ethoxy}-benzonitrile. The compound was purified by preparative HPLC (Zorbas column) using a gradient od acetonitril and water (containing 0.5% formic acid) as eluant. Off-white solid (60%). MS (Turbo Spray): m/z=563.3 [M+H].
Intermediates a) (−)-4-{2-[2-(4-Chloro-phenyl)-5,6-difluoro-benzoimidazol-1-yl]-2-cyclohexyl-1,1-dimethyl-ethoxy}-benzonitrile A solution of 1.0 g (2.39 mmol) (−)-1-[2-(4-chloro-phenyl)-5,6-difluoro-benzoimidazol-1-yl]-1-cyclohexyl-2-methyl-propan-2-ol and 0.289 g (2.39 mmol) 4-fluorobenzonitrile (commercially available) in 10 ml anhydrous tetrahydrofuran was cooled down to 0° C. Then, 4.77 ml (2.39 mmol) potassium bis(trimethylsilyl)amide (0.5 M solution in toluene) were added dropwise to the reaction mixture. The cooling bath was removed and the reaction stirred at room temperature for 5 days. The yellow suspension was poured onto 10% aqueous ammonium chloride solution and the phases were separated. The aqueous layer was extracted three times with ethyl acetate, the combined organic layers were washed with brine, dried over magnesium sulfate, filtered and evaporated. The compound was purified twice by silica gel chromatography using a MPLC system (CombiFlash Companion, Isco Inc.) eluting first with n-heptane for 5 min, then with a gradient of dichloromethane:ethyl acetate (100:0 to 90:10). Colorless foam (40%). MS (Turbo Spray): m/z=520.2 [M+H].

b) (−)-1-[2-(4-Chloro-phenyl)-5,6-difluoro-benzoimidazol-1-yl]-1-cyclohexyl-2-methyl-propan-2-ol To the solution of 3.0 g (7.16 mmol) (−)-[2-(4-chloro-phenyl)-5,6-difluoro-benzoimidazol-1-yl]-cyclohexyl-acetic acid methyl ester in 50 ml tetrahydrofuran were added dropwise 8.36 ml (25.1 mmol) methyl magnesiumbromide (3M in diethyl ether, commercially available) during 5 min. at room temperature. After 18 h the reaction mixture was poured onto 300 ml aqueous saturated potassium sodium tartrate solution and the phases were separated. The aqueous phase was extracted three times with ethyl acetate and the combined organic layers were washed with water and brine, dried over magnesium sulfate, filtered and evaporated to dryness. The red oil was taken up in tert-butyl methyl ether and stored in the fridge for 1 h. The precipitated solid was filtered off and washed with tert-butyl methyl ether to give a first batch of the desired compound as a slight red solid (49%). The mother liquor was purified by silica gel chromatography using a MPLC system (CombiFlash Companion, Isco Inc.) eluting with a gradient of heptane:tert-butyl methyl ether (100:0 to 50:50) to give a second batch of compound. Colorless solid (40%). MS (Turbo Spray): m/z=419.3 [M+H[ ].

c) (+) and (−)-[2-(4-Chloro-phenyl)-5,6-difluoro-benzoimidazol-1-yl]-cyclohexyl-acetic acid methyl ester The title compounds were obtained by separation of the stereoisomers of [2-(4-chloro-phenyl)-5,6-difluoro-benzoimidazol-1-yl]-cyclohexyl-acetic acid methyl ester by chiral preparative HPLC (Reprosil Chiral NR) eluting with n-heptane/5% ethanol.

(+)-[2-(4-Chloro-phenyl)-5,6-difluoro-benzoimidazol-1-yl]-cyclohexyl-acetic acid methyl ester Colorless solid. MS (Turbo Spray): m/z=419.1 [M+H].

(−)-[2-(4-Chloro-phenyl)-5,6-difluoro-benzoimidazol-1-yl]-cyclohexyl-acetic acid methyl ester Colorless solid. MS (Turbo Spray): m/z=419.1 [M+H].

d) [2-(4-Chloro-phenyl)-5,6-difluoro-benzoimidazol-1-yl]-cyclohexyl-acetic acid methyl ester To the solution of 1 g (2.47 mmol) [2-(4-chloro-phenyl)-5,6-difluoro-benzoimidazol-1-yl]-cyclohexyl-acetic acid in 10 ml N,N-dimethylformamide, 129 mg (2.964 mmol) sodium hydride (55% dispersion in mineral oil) and 368 mg (2.594 mmol) methyl iodide were added. The reaction was stirred at room temperature for 2 h and then poured on 100 ml ethyl acetate and 100 ml 1M aqueous hydrochloric acid. The phases were separated and the organic layer washed two times with 100 ml water and 100 ml brine. The combined water layers were extracted with 100 ml ethyl acetate, dried over magnesium sulfate, filtered and evaporated. The residue was purified by silica gel chromatography using a MPLC system (CombiFlash Companion, Isco Inc.) eluting with a gradient of n-heptane:ethyl acetate (100:0 to 60:40). Colorless solid (92%). MS (Turbo Spray): m/z=419.1 [M+H].

e) [2-(4-Chloro-phenyl)-5,6-difluoro-benzoimidazol-1-yl]-cyclohexyl-acetic acid

To the suspension of 0.1 g (0.23 mmol) [2-(4-chloro-phenyl)-5,6-difluoro-benzoimidazol-1-yl]-cyclohexyl-acetic acid ethyl ester (Example 1, intermediate b) in 1 ml dioxane and 1 ml water, 17 mg (0.71 mmol) lithium hydroxide monohydrate were added and the reaction stirred under reflux for 3 h. After cooling to room temperature, the solution was partially evaporated, 2 ml water were added and the pH was adjusted to 2 with 3M aqueous hydrochloric acid. The resulting suspension was stirred for 1 h, then filtered and the filter cake was thoroughly washed with water and dried under high vacuum. Colorless solid (88%). MS (Turbo Spray): m/z=403.2 [M−H].

Example 89

(−)-4-{2-[2-(4-Chloro-phenyl)-5,6-difluoro-benzoimidazol-1-yl]-2-cyclohexyl-1,1-dimethyl-ethoxy}-benzoic acid A solution of 0.10 g (0.19 mmol) (−)-4-{2-[2-(4-chloro-phenyl)-5,6-difluoro-benzoimidazol-1-yl]-2-cyclohexyl-1,1-dimethyl-ethoxy}-benzonitrile (Example 88, intermediate a) in 1 ml ethanol was treated with 0.36 ml (3.85 mmol) 32% aqueous sodium hydroxide solution. The resulting suspension was heated to reflux and stirred at this temperature for 1 h during which a solution formed. After cooling down to room temperature the reaction mixture was poured onto 1M aqueous hydrochloric acid solution and the phases were separated. The aqueous layer was extracted three times with ethyl acetate and the combined organic layers were washed with brine, dried over magnesium sulfate, filtered and evaporated. The remaining solid was treated with tert-butyl methyl ether, homogenized, filtered and washed with tert-butyl methyl ether. White solid (63%). MS (Turbo Spray): m/z=539.3 [M+H].

Example 90

2-(4-{2-[2-(4-Chloro-phenyl)-5,6-difluoro-benzoimidazol-1-yl]-2-cyclohexyl-ethoxy}-phenoxy)-2-methyl-propionic acid The title compound was prepared in analogy to Example 4, from 2-(4-{2-[2-(4-chloro-phenyl)-5,6-difluoro-benzoimidazol-1-yl]-2-cyclohexyl-ethoxy}-phenoxy)-2-methyl-propionic acid ethyl ester. White solid (88%). MS (Turbo Spray): m/z=567.2 [M−H].

Intermediate 2-(4-{2-[2-(4-Chloro-phenyl)-5,6-difluoro-benzoimidazol-1-yl]-2-cyclohexyl-ethoxy}-phenoxy)-2-methyl-propionic acid ethyl ester To a solution of 200 mg (0.512 mmol) 2-[2-(4-chloro-phenyl)-5,6-difluoro-benzoimidazol-1-yl]-2-cyclohexyl-ethanol (Ex. 1, int. c) in 5 ml tetrahydrofuran were added 126 mg (0.563 mmol) 2-(4-hydroxy-phenoxy)-2-methyl-propionic acid ethyl ester (CAS RN 42806-90-6) and 124 mg (0.614 mmol) tri-n-butylphosphin. The reaction mixture was cooled down to 0° C. 106 mg (0.614 mmol) N,N,N',N'-tetramethylazodicarboxamide were added and the reaction mixture was stirred for 18 hours at room temperature. The reaction mixture was concentrated under vacuum and the residue was purified by silica gel chromatography using a MPLC system (CombiFlash Companion, Isco Inc.) eluting with a gradient of n-heptane:ethyl acetate (100:0 to 70:30) to give the title compound as colorless solid (74%). MS (Turbo Spray): m/z=597.2 [M+H].

Example 91

(4-{2-[2-(4-Chloro-phenyl)-5,6-difluoro-benzoimidazol-1-yl]-2-cyclohexyl-ethoxy}-phenoxy)-acetic acid The title compound was prepared in analogy to Example 4, from (4-{2-[2-(4-chloro-phenyl)-5,6-difluoro-benzoimidazol-1-yl]-2-cyclohexyl-ethoxy}-phenoxy)-acetic acid methyl ester. White solid (97%). MS (Turbo Spray): m/z=541.2 [M+H].

Intermediate (4-{2-[2-(4-Chloro-phenyl)-5,6-difluoro-benzoimidazol-1-yl]-2-cyclohexyl-ethoxy}-phenoxy)-acetic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), (4-hydroxy-phenoxy)-acetic acid methyl ester (commercially available), tri-n-butylphosphin and N,N',N'-tetramethylazodicarboxamide. The compound was purified by preparative HPLC (phenomenex gemini column) eluting with a gradient of acetonitril:water (50:50 to 95:5). Colorless oil. MS (Turbo Spray): m/z=555.2 [M+H].

Example 92

(4-{2-[2-(4-Chloro-phenyl)-5,6-difluoro-benzoimidazol-1-yl]-2-cyclohexyl-ethoxy}-2-methyl-phenoxy)-acetic acid The title compound was prepared in analogy to Example 4, from (4-{2-[2-(4-chloro-phenyl)-5,6-difluoro-benzoimidazol-1-yl]-2-cyclohexyl-ethoxy}-2-methyl-phenoxy)-acetic acid ethyl ester. Colorless solid (87%). MS (Turbo Spray): m/z=555.2 [M+H].

Intermediate (4-{2-[2-(4-Chloro-phenyl)-5,6-difluoro-benzoimidazol-1-yl]-2-cyclohexyl-ethoxy}-2-methyl-phenoxy)-acetic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), (4-hydroxy-2-methyl-phenoxy)-acetic acid (CAS RN 317319-10-1), tri-n-butylphosphin and N,N,N',N'-tetramethylazodicarboxamide. The residue was purified by silica gel chromatography using a MPLC system (CombiFlash Companion, Isco Inc.) eluting with a gradient of n-heptane:ethyl acetate (100:0 to 70:30) to give the title compound as a light yellow foam (16%). MS (Turbo Spray): m/z=583.3 [M+H].

Example 93

2-(4-{2-[2-(4-Chloro-phenyl)-5,6-difluoro-benzoimidazol-1-yl]-2-cyclohexyl-ethoxy}-2,3-dimethyl-phenoxy)-2-methyl-propionic acid The title compound was prepared in analogy to Example 4, from 2-(4-{2-[2-(4-chloro-phenyl)-5,6-difluoro-benzoimidazol-1-yl]-2-cyclohexyl-ethoxy}-2,3-dimethyl-phenoxy)-2-methyl-propionic acid ethyl ester. Colorless solid (49%). MS (Turbo Spray): m/z=597.3 [M+H].

Intermediate 2-(4-{2-[2-(4-Chloro-phenyl)-5,6-difluoro-benzoimidazol-1-yl]-2-cyclohexyl-ethoxy}-2,3-dimethyl-phenoxy)-2-methyl-propionic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), 2-(4-hydroxy-2,3-dimethyl-phenoxy)-2-methyl-propionic acid ethyl ester (CAS RN: 851508-28-6), tri-n-butylphosphin and N,N,N',N'-tetramethylazodicarboxamide. The compound was purified by silica gel chromatography using a MPLC system (CombiFlash Companion, Isco Inc.) eluting with a gradient of n-heptane:ethyl acetate (100:0 to 70:30). Colorless oil (11%). MS (Turbo Spray): m/z=625.5 [M+H].

Example 94

2-(4-{2-[2-(4-Chloro-phenyl)-5,6-difluoro-benzoimidazol-1-yl]-2-cyclohexyl-ethoxy}-3-fluoro-phenoxy)-2-methyl-propionic acid The title compound was prepared in analogy to Example 4, from 2-(4-{2-[2-(4-chloro-phenyl)-5,6-difluoro-benzoimidazol-1-yl]-2-cyclohexyl-ethoxy}-3-fluoro-phenoxy)-2-methyl-propionic acid ethyl ester. Colorless solid (68%). MS (Turbo Spray): m/z=587.2 [M+H].

Intermediate 2-(4-{2-[2-(4-Chloro-phenyl)-5,6-difluoro-benzoimidazol-yl]-2-cyclohexyl-ethoxy}-3-fluoro-phenoxy)-2-methyl-propionic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), 2-(3-fluoro-4-hydroxy-phenoxy)-2-methyl-propionic acid ethyl ester (CAS RN 851508-67-3), tri-n-butylphosphin and N,N,N',N'-tetramethylazodicarboxamide. The compound was purified by silica gel chromatography using a MPLC system (CombiFlash Companion, Isco Inc.) eluting with a gradient of n-heptane:ethyl acetate (100:0 to 70:30). Light yellow oil (64%). MS (Turbo Spray): m/z=615.3 [M+H].

Example 95

2-(3-{2-[2-(4-Chloro-phenyl)-5,6-difluoro-benzoimidazol-1-yl]-2-cyclohexyl-ethoxy}-phenoxy)-2-methyl-propionic acid The title compound was prepared in analogy to Example 4, from 2-(3-{2-[2-(4-chloro-phenyl)-5,6-difluoro-benzoimidazol-1-yl]-2-cyclohexyl-ethoxy}-phenoxy)-2-methyl-propionic acid ethyl ester. White solid (82%). MS (Turbo Spray): m/z=569.4 [M+H].

Intermediate 2-(3-{2-[2-(4-chloro-phenyl)-5,6-difluoro-benzoimidazol-1-yl]-2-cyclohexyl-ethoxy}-phenoxy)-2-methyl-propionic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Ex. 1, int. c), 2-(3-hydroxy-phenoxy)-2-methyl-propionic acid ethyl ester (CAS RN: 328919-24-0), tri-n-butylphosphin and N,N,N',N'-tet-

Example 96

4-{2-Cyclohexyl-2-[2-(2,6-dimethoxy-pyridin-3-yl)-5 6-difluoro-benzoimidazol-1-yl]-ethoxy}-3,5-difluoro-benzoic acid The title compound was prepared in analogy to Example 4, from 4-{2-Cyclohexyl-2-[2-(2,6-dimethoxy-pyridin-3-yl)-5,6-difluoro-benzoimidazol-1-yl]-ethoxy}-3,5-difluoro-benzoic acid methyl ester. White solid (84%). MS (Turbo Spray): m/z=574.3 [M+H].
Intermediate 4-{2-Cyclohexyl-2-[2-(2,6-dimethoxy-pyridin-3-yl)-5,6-difluoro-benzoimidazol-1-yl]-ethoxy}-3,5-difluoro-benzoic acid methyl ester The title compound was prepared in analogy to Example 4, intermediate, from 2-cyclohexyl-2-[2-(2,6-dimethoxy-pyridin-3-yl)-5,6-difluoro-benzoimidazol-1-yl]-ethanol (Example 73, intermediate b), 3,5-difluoro-4-hydroxy-benzoic acid methyl ester (commercially available), tri-N-butylphosphine and N'N'N'N-tetramethylazodicarboxylate. The compound was purified by silica gel chromatography using a MPLC system (CombiFlash Companion, Isco Inc.) eluting with a gradient of n-heptane:tert-butyl methyl ether (100:0 to 50:50). Off-white foam (45%). MS (Turbo Spray): m/z=588.3 [M+H].

Examples 97 and 98

The title compounds were obtained by separation of the stereoisomers of 4-{2-cyclohexyl-2-[2-(2,6-dimethoxy-pyridin-3-yl)-5,6-difluoro-benzoimidazol-1-yl]-ethoxy}-3,5-difluoro-benzoic acid (Example 97) by chiral preparative HPLC (Reprosil Chiral NR) eluting with n-heptane:ethanol (containing 0.5% formic acid) 80:20.

(+)-4-{2-Cyclohexyl-2-[2-(2,6-dimethoxy-pyridin-3-yl)-5,6-difluoro-benzoimidazol-1-yl]-ethoxy}-3,5-difluoro-benzoic acid Colorless solid. MS (Turbo Spray): m/z=574.3 [M+H].

(−)-4-{2-Cyclohexyl-2-[2-(2,6-dimethoxy-pyridin-3-yl)-5,6-difluoro-benzoimidazol-1-yl]-ethoxy}-3,5-difluoro-benzoic acid Colorless solid. MS (Turbo Spray): m/z=574.3 [M+H].

Example 99

1-{1-cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole To a solution of 0.18 g (0.33 mmol) 4-{2-cyclohexyl-2-[2-(2,6-dimethoxy-pyridin-3-yl)-5,6-difluoro-benzoimidazol-1-yl]-ethoxy}-3,5-dimethyl-benzonitrile in 3 ml o-xylene were added 0.227 g (1.65 mmol) triethylamine hydrochloride and 0.107 g (2.65 mMol) sodium azide and the solution was heated for 7 h at 145° C. (oil bath temperature). The reaction was allowed to cool down to room temperature overnight and then was poured onto 1M aqueous hydrochloric acid solution and extracted three times with ethyl acetate. The combined organic layers were washed with brine, dried over magnesium sulfate, filtered and evaporated. The remaining oil was dissolved in acetonitrile, the solution was completely evaporated and the residue dissolved in 20 ml tert-butyl methyl ether under warming to 45° C. The solution was partially evaporated, then stored at 4° C. overnight. The resulting suspension was filtered, washed with tert-butyl methyl ether and dried under high vacuum. Light brown solid (75%). MS (Turbo Spray): m/z=590.44 [M+H].
Intermediate 4-{2-Cyclohexyl-2-[2-(2,6-dimethoxy-pyridin-3-yl)-5,6-difluoro-benzoimidazol-1-yl]-ethoxy}-3,5-dimethyl-benzonitrile The title compound was obtained from 2-cyclohexyl-2-[2-(2,6-dimethoxy-pyridin-3-yl)-5,6-difluoro-benzoimidazol-1-yl]-ethanol (Example 73, intermediate b), 4-hydroxy-3,5-dimethyl-benzonitrile (commercially available), tri-N-butylposphine and N'N'N'N-tetramethylazodicarboxylate. The compound was purified by silica gel chromatography using a MPLC system (CombiFlash Companion, Isco Inc.) eluting first with n-heptane for 5 min., then with a gradient of dichloromethane:ethyl acetate (100:0 to 95:5). Light brown foam (28%). MS (Turbo Spray): m/z=547.3 [M+H].

Examples 100 and 101

The title compounds were obtained by separation of the stereoisomers of 1-{1-cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole (Example 100) by chiral preparative HPLC (Reprosil Chiral NR) eluting with n-heptane:ethanol (with 0.01M ammonium acetate) 60:40.

(+)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole Light brown foam. MS (Turbo Spray): m/z=590.4 [M+H].

(−)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole Light brown foam. MS (Turbo Spray): m/z=590.4 [M+H].

Example 102

4-{2-[2-(4-Chloro-phenyl)-benzoimidazol-1-yl]-2-cyclohexyl-ethoxy}-3,5-difluoro-benzoic acid The title compound was prepared in analogy to Example 4, from 4-{2-[2-(4-chloro-phenyl)-benzoimidazol-1-yl]-2-cyclohexyl-ethoxy}-3,5-difluoro-benzoic acid methyl ester. The compound was purified by preparative HPLC (phenomenex gemini column) eluting with a gradient of acetonitrile:water (50:50 to 95:5). Colorless solid (53%). MS (Turbo Spray): m/z=511.4 [M+H].

Intermediate

4-{2-[2-(4-Chloro-phenyl)-benzoimidazol-1-yl]-2-cyclohexyl-ethoxy}-3,5-difluoro-benzoic acid methyl ester The title compound was synthesized in analogy to Example 4, intermediate, from 2-[2-(4-chloro-phenyl)-benzoimidazol-1-yl]-2-cyclohexyl-ethanol (Example 32, intermediate b), 3,5-difluoro-4-hydroxy-benzoic acid methyl ester (commercially available), triphenylphosphine and di-tert-butyl azodicarboxylate. The residue was purified by silica gel chromatography using a MPLC system (CombiFlash Companion, Isco Inc.) eluting with a gradient of n-heptane:ethyl acetate (100:0 to 70:30). White foam. MS (Turbo Spray): m/z=525.1 [M+H].

Examples 103 and 104

The title compounds were obtained by separation of the stereoisomers of 4-{2-[2-(4-Chloro-phenyl)-benzoimidazol-1-yl]-2-cyclohexyl-ethoxy}-3,5-difluoro-benzoic acid (Example 103) by chiral preparative HPLC (Reprosil Chiral NR) eluting with n-heptane:ethanol (containing 0.5% formic acid) 85:15.

(+)-4-{2-[2-(4-Chloro-phenyl)-benzoimidazol-1-yl]-2-cyclohexyl-ethoxy}-3,5-difluoro-benzoic acid
Name Colorless solid. MS (Turbo Spray): m/z=511.3 [M+H].

(−)-4-{2-[2-(4-Chloro-phenyl)-benzoimidazol-1-yl]-2-cyclohexyl-ethoxy}-3,5-difluoro-benzoic acid
Name Colorless solid. MS (Turbo Spray): m/z=511.3 [M+H].

Example 105

4-{2-[2-(4-Chloro-phenyl)-benzoimidazol-1-yl]-2-cyclohexyl-ethoxy}-3,5-dimethyl-benzoic acid The title compound was prepared in analogy to Example 4, from 4-{2-[2-(4-chloro-phenyl)-benzoimidazol-1-yl]-2-cyclohexyl-ethoxy}-3,5-dimethyl-benzoic acid methyl ester. The compound was purified by preparative HPLC (phenomenex gemini column) eluting with a gradient of acetonitrile:water (50:50 to 95:5) to give the desired compound as a colorless solid (41%). MS (Turbo Spray): m/z=502.2 [M+H].
Intermediate 4-{2-[2-(4-Chloro-phenyl)-benzoimidazol-1-yl]-2-cyclohexyl-ethoxy}-3,5-dimethyl-benzoic acid methyl ester The title compound was prepared in analogy to Example 4, intermediate, from 2-[2-(4-chloro-phenyl)-benzoimidazol-1-yl]-2-cyclohexyl-ethanol (Example 32, intermediate b), 4-hydroxy-3,5-dimethyl-benzoic acid methyl ester (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30). White foam. MS (Turbo Spray): m/z=517.3 [M+H].

Examples 106 and 107

The title compounds were obtained by separation of the stereoisomers of 4-{2-[2-(4-chloro-phenyl)-benzoimidazol-1-yl]-2-cyclohexyl-ethoxy}-3,5-dimethyl-benzoic acid (Example 106) by chiral preparative HPLC (Reprosil Chiral NR) eluting with n-heptane:ethanol (containing 0.5% formic acid) 85:15.

(−)-4-{2-[2-(4-Chloro-phenyl)-benzoimidazol-1-yl]-2-cyclohexyl-ethoxy}-3,5-dimethyl-benzoic acid Colorless solid. MS (Turbo Spray): m/z=503.3 [M+H].

(+)-4-{2-[2-(4-Chloro-phenyl)-benzoimidazol-1-yl]-2-cyclohexyl-ethoxy}-3,5-dimethyl-benzoic acid Colorless solid. MS (Turbo Spray): m/z=503.3 [M+H].

Example 108

3-Chloro-4-{2-[2-(4-chloro-phenyl)-benzoimidazol-1-yl]-2-cyclohexyl-ethoxy}-5-fluoro-benzoic acid The title compound was prepared in analogy to Example 4, from 3-chloro-4-{2-[2-(4-chloro-phenyl)-benzoimidazol-1-yl]-2-cyclohexyl-ethoxy}-5-fluoro-benzoic acid methyl ester. Colorless solid (37%). MS (Turbo Spray): m/z=527.1 [M+H].
Intermediate 3-Chloro-4-{2-[2-(4-chloro-phenyl)-benzoimidazol-1-yl]-2-cyclohexyl-ethoxy}-5-fluoro-benzoic acid methyl ester The title compound was prepared in analogy to Example 4, intermediate, from 2-[2-(4-chloro-phenyl)-benzoimidazol-1-yl]-2-cyclohexyl-ethanol (Example 32, intermediate b), 3-chloro-5-fluoro-4-hydroxy-benzoic acid methyl ester (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30) as eluant. Colorless foam. MS (Turbo Spray): m/z=541.2 (M+H).

Examples 109 and 110

The title compounds were obtained by separation of the stereoisomers of 3-chloro-4-{2-[2-(4-chloro-phenyl)-benzoimidazol-1-yl]-2-cyclohexyl-ethoxy}-5-fluoro-benzoic acid (Example 109) by chiral preparative HPLC (Chiracel OD) eluting with n-heptane:ethanol (containing 0.5% formic acid) 93:7

(−)-3-Chloro-4-{2-[2-(4-chloro-phenyl)-benzoimidazol-1-yl]-2-cyclohexyl-ethoxy}-5-fluoro-benzoic acid Colorless solid. MS (Turbo Spray): m/z=527.1 [M+H].

(+)-3-Chloro-4-{2-[2-(4-chloro-phenyl)-benzoimidazol-1-yl]-2-cyclohexyl-ethoxy}-5-fluoro-benzoic acid Colorless solid. MS (Turbo Spray): m/z=527.1 [M+H].

Example 111

2-(4-Chloro-phenyl)-1-{1-cyclohexyl-2-[2,6-dimethyl-4-(1H-tetrazol-5-yl)-phenoxy]-ethyl}-1H-benzoimidazole The title compound was prepared in analogy to Example 56, from 4-{2-[2-(4-chloro-phenyl)-benzoimidazol-1-yl]-2-cyclohexyl-ethoxy}-3,5-dimethyl-benzonitrile. The crude product was purified by silica gel chromatography using a MPLC system (CombiFlash Companion, Isco Inc.) eluting with a gradient of n-heptane:ethyl acetate:methanol (100:0:0 to 0:100:0 to 50:50). Colorless solid (45%). MS (Turbo Spray): m/z=527.2 [M+H].

Intermediate

4-{2-[2-(4-Chloro-phenyl)-benzoimidazol-1-yl]-2-cyclohexyl-ethoxy}-3,5-dimethyl-benzonitrile The title compound was prepared in analogy to Example 4, intermediate, from 2-[2-(4-chloro-phenyl)-benzoimidazol-1-yl]-2-cyclohexyl-ethanol (Example 32, intermediate b), 3,5-dimethyl-4-hydroxybenzonitrile (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30). The residue was purified a second time by preparative HPLC (phenomenex gemini column) using a gradient of acetonitril:water (50:50 to 95:5). Colorless foam (57%). MS (Turbo Spray): m/z=484.4 [M+H].

Examples 112 and 113

The title compounds were obtained by separation of the stereoisomers of 2-(4-chloro-phenyl)-1-{1-cyclohexyl-2-[2,6-dimethyl-4-(1H-tetrazol-5-yl)-phenoxy]-ethyl}-1H-benzoimidazole (Example 112) by chiral preparative HPLC (Reprosil Chiral NR) eluting with n-heptane:ethanol (with 0.01M ammonium acetate) 65:35.

(−)-2-(4-Chloro-phenyl)-1-{1-cyclohexyl-2-[2,6-dimethyl-4-(1H-tetrazol-5-yl)-phenoxy]-ethyl}-1H-benzoimidazole Colorless solid. MS (Turbo Spray): m/z=527.2 [M+H].

(+)-2-(4-Chloro-phenyl)-1-{1-cyclohexyl-2-[2,6-dimethyl-4-(1H-tetrazol-5-yl)-phenoxy]-ethyl}-1H-benzoimidazole Colorless solid. MS (Turbo Spray): m/z=527.2 [M+H].

Example 114

5-Bromo-6-{2-[2-(4-chloro-phenyl)-5,6-difluoro-benzoimidazol-1-yl]-2-cyclohexyl-ethoxy}-nicotinic acid The title compound was prepared in analogy to Example 4, from 5-bromo-6-{2-[2-(4-chloro-phenyl)-5,6-difluoro-benzoimidazol-1-yl]-2-cyclohexyl-ethoxy}-nicotinic acid methyl ester. Colorless solid (67%). MS (Turbo Spray): m/z=587.9 [M+H].

Intermediate

5-Bromo-6-{2-[2-(4-chloro-phenyl)-5,6-difluoro-benzoimidazol-1-yl]-2-cyclohexyl-ethoxy}-nicotinic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), methyl 5-bromo-6-hydroxynicotinate (commercially available), triphenylphosphine and di-tert-butyl azodicarboxylate. The residue obtained after work-up was crystallized from acetonitrile. Colorless solid (86%). MS (Turbo Spray): m/z=604.3 [M+H].

Example 115

(+) or (−)-2-(4-Chloro-phenyl)-1-[1-cyclohexyl-2-[2,6-difluoro-4-(1H-tetrazol-5-yl)-phenoxy]-2-methyl-propyl]-5,6-difluoro-1H-benzoimidazole The title compound was prepared in analogy to Example 56, from (+)-4-{2-[2-(4-chloro-phenyl)-5,6-difluoro-benzoimidazol-1-yl]-2-cyclohexyl-1,1-dimethyl-ethoxy}-3,5-difluoro-benzonitrile. Light brown solid (73%). MS (Turbo Spray): m/z=599.3 [M+H].

Intermediate (+)-4-{2-[2-(4-Chloro-phenyl)-5,6-difluoro-benzoimidazol-1-yl]-2-cyclohexyl-1,1-dimethyl-ethoxy}-3,5-difluoro-benzonitrile A solution of 0.10 g (0.24 mmol) (−)-1-[2-(4-chloro-phenyl)-5,6-difluoro-benzoimidazol-1-yl]-1-cyclohexyl-2-methyl-propan-2-ol (Example 88, intermediate b) and 38 mg (0.24 mmol) 3,4,5-trifluorobenzonitrile in 2 ml anhydrous tetrahydrofuran was cooled down to 0° C. Then, 0.53 ml (0.26 mmol) potassium bis(trimethylsilyl)amide (0.5 M solution in toluene) were added dropwise to the reaction mixture. The cooling bath was removed and stirring was continued for 18 h. The reaction mixture was poured onto aqueous saturated ammonium chloride solution and the phases were separated. The aqueous layer was extracted three times with ethyl acetate. The combined organic layers were washed with brine, dried over magnesium sulfate, filtered and evaporated. The residue was purified by silica gel chromatography using a MPLC system (CombiFlash Companion, Isco Inc.) eluting with n-heptane for 5 min., then with a gradient of dichloromethane:ethyl acetate (100:0 to 95:5). Light brown foam (45%). MS (Turbo Spray): m/z=556.2 [M+H].

Example 116

(+)-4-{2-[2-(4-Chloro-phenyl)-5,6-difluoro-benzoimidazol-1-yl]-2-cyclohexyl-1,1-dimethyl-ethoxy}-3,5-difluoro-benzoic acid To a solution of 0.24 g (0.43 mmol) (+)-4-{2-[2-(4-chloro-phenyl)-5,6-difluoro-benzoimidazol-1-yl]-2-cyclohexyl-1,1-dimethyl-ethoxy}-3,5-difluoro-benzonitrile (Example 115, intermediate) in 1 ml ethanole were added 0.8 ml (8.63 mmol) 32% aqueous sodium hydroxide solution. The suspension was heated for 5 h at reflux to give a clear, light yellow solution. After cooling down to room temperature the reaction mixture was poured onto 1M aqueous hydrochloric acid and the phases were separated. The aqueous phase was extracted three times with ethyl acetate. The organic layers were washed with brine, dried over magnesium sulfate, filtered and evaporated. The residue was dissolved in tert-butyl methyl ether and stored in the fridge for 48 h. The mixture was evaporated and taken up in acetonitrile upon which a white suspension formed. This suspension was filtered, washed with acetonitrile and dried under high vacuum. White solid (79%). MS (Turbo Spray): m/z=575.4 [M+H].

Example 117

1-(4-{2-[2-(4-Chloro-phenyl)-5,6-difluoro-benzoimidazol-1-yl]-2-cyclohexyl-ethoxy}-phenoxy)-cyclobutanecarboxylic acid The title compound was prepared in analogy to Example 4, from 1-(4-{2-[2-(4-chloro-phenyl)-5,6-difluoro-benzoimidazol-1-yl]-2-cyclohexyl-ethoxy}-phenoxy)-cyclobutanecarboxylic acid ethyl ester. The compound was purified preparative HPLC (phenomenex gemini column) eluting with a gradient of acetonitrile:water (50:50 to 95:5). Colorless solid (81%). MS (Turbo Spray): m/z=581.2 [M+H].
Intermediate 1-(4-{2-[2-(4-Chloro-phenyl)-5,6-difluoro-benzoimidazol-1-yl]-2-cyclohexyl-ethoxy}-phenoxy)-cyclobutanecarboxylic acid ethyl ester The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), 1-(4-hydroxy-phenoxy)-cyclobutanecarboxylic acid ethyl ester (CAS RN: 879094-83-4), tri-n-butylphosphin and N,N,N',N'-tetramethylazodicarboxamide. The compound was purified by silica gel chromatography using a MPLC system (CombiFlash Companion, Isco Inc.) eluting with a gradient of n-heptane:ethyl acetate (100:0 to 70:30). Light yellow foam (45%). MS (Turbo Spray): m/z=609.3 [M+H].

Examples 118 and 119

The title compounds were obtained by separation of the stereoisomers of 1-(4-{2-[2-(4-chloro-phenyl)-5,6-difluoro-benzoimidazol-1-yl]-2-cyclohexyl-ethoxy}-phenoxy)-cyclobutanecarboxylic acid by chiral preparative HPLC (Reprosil Chiral NR) eluting with n-heptane:ethanol (containing 0.5% formic acid) 85:15.

(+)-1-(4-{2-[2-(4-Chloro-phenyl)-5,6-difluoro-benzoimidazol-1-yl]-2-cyclohexyl-ethoxy}-phenoxy)-cyclobutanecarboxylic acid Colorless solid. MS (Turbo Spray): m/z=581.2 [M+H].

(−)-1-(4-{2-[2-(4-Chloro-phenyl)-5,6-difluoro-benzoimidazol-1-yl]-2-cyclohexyl-ethoxy}-phenoxy)-cyclobutanecarboxylic acid Colorless solid. MS (Turbo Spray): m/z=581.2 [M+H].

Example 120

1-(4-{2-[2-(4-Chloro-phenyl)-5,6-difluoro-benzoimidazol-1-yl]-2-cyclohexyl-ethoxy}-phenoxy)-cyclopropanecarboxylic acid The title compound was prepared in analogy to Example 4, from 1-(4-{2-[2-(4-chloro-phenyl)-5,6-difluoro-benzoimidazol-1-yl]-2-cyclohexyl-ethoxy}-phenoxy)-cyclopropanecarboxylic acid methyl ester. The compound was purified by preparative HPLC (phenomenex gemini column) with a gradient of acetonitrile:water (50:50 to 95:5). Colorless solid (74%). MS (Turbo Spray): m/z=567.2 [M+H].
Intermediate 1-(4-{2-[2-(4-Chloro-phenyl)-5,6-difluoro-benzoimidazol-1-yl]-2-cyclohexyl-ethoxy}-phenoxy)-cyclopropanecarboxylic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), 1-(4-hydroxy-phenoxy)-cyclopropanecarboxylic acid (CAS RN: 857903-44-7) and N,N,N',N'-tetramethylazodicarboxamide. The compound was purified by silica gel chromatography using a MPLC system (CombiFlash Companion, Isco Inc.) eluting with a gradient of n-heptane:ethyl acetate (100:0 to 70:30). Light yellow foam (31%). MS (Turbo Spray): m/z=581.2 [M+H].

Examples 121 and 122

The title compounds were obtained by separation of the stereoisomers of 1-(4-{2-[2-(4-chloro-phenyl)-5,6-difluoro-benzoimidazol-1-yl]-2-cyclohexyl-ethoxy}-phenoxy)-cyclopropanecarboxylic acid (Example 121) by chiral preparative HPLC (Chiralpak AD) eluting with n-heptane/15% ethanol (containing 0.5% formic acid).

(−)-1-(4-{2-[2-(4-Chloro-phenyl)-5,6-difluoro-benzoimidazol-1-yl]-2-cyclohexyl-ethoxy}-phenoxy)-cyclopropanecarboxylic acid Colorless solid. MS (Turbo Spray): m/z=567.3 [M+H].

(+)-1-(4-{2-[2-(4-Chloro-phenyl)-5,6-difluoro-benzoimidazol-1-yl]-2-cyclohexyl-ethoxy}-phenoxy)-cyclopropanecarboxylic acid Name Colorless solid. MS (Turbo Spray): m/z=567.3 [M+H].

Example 123

6-{2-[2-(4-Chloro-2-methyl-phenyl)-5,6-difluoro-benzoimidazol-1-yl]-2-cyclohexyl-ethoxy}-nicotinic acid The title compound was prepared in analogy to Example 4, from 6-{2-[2-(4-chloro-2-methyl-phenyl)-5,6-difluoro-benzoimidazol-1-yl]-2-cyclohexyl-ethoxy}-nicotinic acid methyl ester. The compound was purified by preparative HPLC (phenomenex gemini column) eluting with a gradient of acetonitril:water (50:50 to 95:5). Colorless solid (81%). MS (Turbo Spray): m/z=526.1 [M+H].
Intermediates a) 6-{2-[2-(4-Chloro-2-methyl-phenyl)-5,6-difluoro-benzoimidazol-1-yl]-2-cyclohexyl-ethoxy}-nicotinic acid methyl ester To a solution of 200 mg (0.494 mmol) 2-[2-(4-chloro-2-methyl-phenyl)-5,6-difluoro-benzoimidazol-1-yl]-2-cyclohexyl-ethanol in 5 ml tetrahydrofuran were added 83 mg (0.543 mmol) methyl 6-hydroxynicotinate (commercially available) and 120 mg (0.593 mmol) tri-n-butylphosphin. The reaction mixture was cooled down to 0° C. 102 mg (0.593 mmol) N,N,N',N'-tetramethylazodicarboxamide were added. The reaction mixture was stirred for 18 hours at room temperature and then concentrated under vacuum. The residue was purified by silica gel chromatography using a MPLC system (CombiFlash Companion, Isco Inc.) eluting with a gradient of n-heptane:ethyl acetate (100:0 to 70:30). Light yellow solid (29%). MS (Turbo Spray): m/z=540.2 [M+H].

b) 2-[2-(4-Chloro-2-methyl-phenyl)-5,6-difluoro-benzoimidazol-1-yl]-2-cyclohexyl-ethanol To a solution of 0.94 g (2.244 mmol) [2-(4-chloro-2-methyl-phenyl)-5,6-difluoro-benzoimidazol-1-yl]-cyclohexyl-acetic acid in 15 ml dry tetrahydrofuran was added 98 mg (2.356 mmol) lithium aluminum hydride at 0° C. The reaction mixture was allowed to warm to room temperature and was stirred for 2 hours. The reaction mixture was poured on 50 ml 10% aqueous sodium potassium tartrate solution and 50 ml ethyl acetate. The layers were separated and the aqueous layers were extracted again with 50 ml ethyl acetate. The combined organic layers were washed with 50 ml brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate (100:0 to 60:40) to give the title compound as a light yellow solid (57%). MS (Turbo Spray): m/z=405.4 [M+H].

c) [2-(4-Chloro-2-methyl-phenyl)-5,6-difluoro-benzoimidazol-1-yl]-cyclohexyl-acetic acid N-benzyl-2-[2-(4-chloro-2-methyl-phenyl)-5,6-difluoro-benzoimidazol-1-yl]-2-cyclohexyl-acetamide (3.8 g, 6.508 mmol) were dissolved in 49.3 ml (521.9 mmol) acetic acid anhydride and 24.7 ml (431.5 mmol) acetic acid. The dark brown solution was cooled to 0-5° C. and 2.245 g (32.54 mmol) sodium nitrite were added in four portions within 10 min. After 30 min. the reaction mixture was allowed to warm to room temperature. The reaction mixture was then evaporated, taken up with toluene and evaporated again. The residue was extracted twice ethyl acetate, saturated aqueous sodium bicarbonate solution, water and brine. The organic layers were separated, dried over magnesium sulfate, filtered and evaporated. The crude intermediate was then dissolved in a mixture of tetrahydrofuran and water. To the dark brown solution slowly a solution of lithiumhydroxide monohydrate in 30% aqueous hydrogen peroxide was added dropwise over 20 min (gas evolution, exothermic). The mixture was stirred until all starting material had disappeared. The reaction mixture was then evaporated and the pH of the residue was adjusted to 4 with acetic acid. Ethyl acetate was added, the phases separated and the aqueous layer extracted another time with ethyl acetate. The combined organic layers were washed with water and brine, dried over magnesium sulfate and evaporated. The residue was taken up in toluene, stirred at 0-5° C. for 15', the solid was filtered off, washed with cold toluene and dried in vacuum to give the desired compound as a beige solid (54%). MS (ESI): 418.87 (M$^+$).

c) N-Benzyl-2-[2-(4-chloro-2-methyl-phenyl)-5,6-difluoro-benzoimidazol-1-yl]-2-cyclohexyl-acetamide To the solution of 1.5 g (6.145 mmol) 2-amino-4,5-difluoro-phenyl)-carbamic acid tert-butyl ester (Example 73, intermediate g), 1.080 g (6.145 mmol) 4-chloro-2-methyl-benzoic acid (commercially available), 985.5 ul (7.375 mmol) cyclohexenecarbaldehyde (commercially available) and 763.5 ul (6.145 mmol) benzyl isocyanide (commercially available) were dissolved in 15 ml methanol and the light brown solution was stirred at room temperature overnight. Then 15.00 ml (60.0 mmol) 4M hydrochloric acid in dioxane (commercially available) were added and the reaction mixture was stirred at room temperature for 4.5 h and then evaporated. The residue was taken up in ethyl acetate and aqueous saturated sodium bicarbonate solution, the phases were separated, the organic phase extracted a second time with ethyl acetate and the combined organic layers washed with water and brine to give, after evaporation, the compound as yellow foam which was pure enough for the next step without further purification. MS (ESI): m/z=508.02 (M$^+$).

Example 124

4-{2-[2-(4-Chloro-2-methyl-phenyl)-5,6-difluoro-benzoimidazol-1-yl]-2-cyclohexyl-ethoxy}-3,5-difluoro-benzoic acid The compound was prepared in analogy to Example 4, from 4-{2-[2-(4-chloro-2-methyl-phenyl)-5,6-difluoro-benzoimidazol-1-yl]-2-cyclohexyl-ethoxy}-3,5-difluoro-benzoic acid methyl ester. Colorless solid (69%). MS (Turbo Spray): m/z=561.1 [M+H].

Intermediate

4-{2-[2-(4-Chloro-2-methyl-phenyl)-5,6-difluoro-benzoimidazol-1-yl]-2-cyclohexyl-ethoxy}-3,5-difluoro-benzoic acid methyl ester The compound was prepared in analogy to Example 4, intermediate, from 2-[2-(4-chloro-2-methyl-phenyl)-5,6-difluoro-benzoimidazol-1-yl]-2-cyclohexyl-ethanol (example 123, intermediate b), 3,5-difluoro-4-hydroxy-benzoic acid methyl ester (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30). Light yellow foam (37%). MS (Turbo Spray): m/z=575.4 [M+H].

Examples 125 and 126

The title compounds were obtained by separation of the stereoisomers of 4-{2-[2-(4-chloro-2-methyl-phenyl)-5,6-difluoro-benzoimidazol-1-yl]-2-cyclohexyl-ethoxy}-3,5-difluoro-benzoic acid (Example 125) by chiral preparative HPLC (Chiralpak AD) eluting with n-heptane/10% ethanol (containing 0.5% formic acid).

(−)-4-{2-[2-(4-Chloro-2-methyl-phenyl)-5,6-difluoro-benzoimidazol-1-yl]-2-cyclohexyl-ethoxy}-3,5-difluoro-benzoic acid Colorless solid. MS (Turbo Spray): m/z=561.1 [M+H].

(+)-4-{2-[2-(4-Chloro-2-methyl-phenyl)-5,6-difluoro-benzoimidazol-1-yl]-2-cyclohexyl-ethoxy}-3,5-difluoro-benzoic acid Colorless solid. MS (Turbo Spray): m/z=561.1 [M+H].

Example 127

2-(4-Chloro-phenyl)-1-{1-cyclohexyl-2-[2,6-difluoro-4-(1H-tetrazol-5-yl)-phenoxy]-ethyl}-5,6-difluoro-1H-benzoimidazole The title compound was prepared in analogy to Example 56, from 4-{2-[2-(4-chloro-phenyl)-5,6-difluoro-benzoimidazol-1-yl]-2-cyclohexyl-ethoxy}-3,5-difluoro-benzonitrile. Off-white solid (52%). MS (Turbo Spray): m/z=571.2 [M+H].
Intermediate

4-{2-[2-(4-Chloro-phenyl)-5,6-difluoro-benzoimidazol-1-yl]-2-cyclohexyl-ethoxy}-3,5-difluoro-benzonitrile The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), 3,5-difluorobenzonitrile (commercially available), triphenylphosphine and di-tert-butyl azodicarboxylate. The compound was purified by silica gel chromatography using a MPLC system (CombiFlash Companion, Isco Inc.) eluting with a gradient of n-heptane:tert-butyl methyl ether (100:0 to 50:50). The product-containing fractions were pooled and chromatographed on a preparative HPLC system (Phenomenex Gemini column) using a gradient of acetonitrile and water. Colorless foam (49%). MS (Turbo Spray): m/z=528.1 [M+H].

Example 128

2-(4-Chloro-phenyl)-1-{1-cyclohexyl-2-[2,6-difluoro-4-(1H-tetrazol-5-yl)-phenoxy]-ethyl}-1H-benzoimidazole The title compound was prepared in analogy to Example 56, from 4-{2-[2-(4-chloro-phenyl)-benzoimidazol-1-yl]-2-cyclohexyl-ethoxy}-3,5-difluoro-benzonitrile. The product was purified by preparative HPLC (phenomenex gemini column) with a gradient of acetonitrile:water (50:50 to 95:5). Light yellow solid (22%). MS (Turbo Spray): m/z=535.2 [M+H].
Intermediate

4-{2-[2-(4-Chloro-phenyl)-benzoimidazol-1-yl]-2-cyclohexyl-ethoxy}-3,5-difluoro-benzonitrile The title compound was prepared in analogy to Example 4, intermediate, from 2-[2-(4-chloro-phenyl)-benzoimidazol-1-yl]-2-cyclohexyl-ethanol (Example 32, intermediate b), 3,5-difluoro-4-hydroxybenzonitrile (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30). Colorless foam. MS (Turbo Spray): m/z=492.4 [M+H].

Example 129

1-{1-Cyclohexyl-2-[2,6-difluoro-4-(1H-tetrazol-5-yl)-phenoxy]-ethyl}-2-(2,6-dimethoxy-pyridin-3-yl)-5,6-difluoro-1H-benzoimidazole The title compound was prepared in analogy to Example 56, from 4-{2-cyclohexyl-2-[2-(2,6-dimethoxy-pyridin-3-yl)-5,6-difluoro-benzoimidazol-1-yl]-ethoxy}-3,5-difluoro-benzonitrile. Colorless solid (68%). MS (Turbo Spray): m/z=598.3 [M+H].
Intermediate

4-{2-Cyclohexyl-2-[2-(2,6-dimethoxy-pyridin-3-yl)-5,6-difluoro-benzoimidazol-1-yl]-ethoxy}-3,5-difluoro-benzonitrile The title compound was prepared in analogy to Example 4, intermediate, from 2-cyclohexyl-2-[2-(2,6-dimethoxy-pyridin-3-yl)-5,6-difluoro-benzoimidazol-1-yl]-ethanol (Example 73, intermediate b), 3,5-difluorobenzonitrile (commercially available), tri-n-butylposphine and N'N'N'N'N-tetramethylazodicarboxamide. The compound was purified in a first step by silica gel chromatography using a MPLC system (CombiFlash Companion, Isco Inc.) eluting with a gradient of heptane:ethyl acetate (100:0 to 50:50). The resulting compound was further purified by preparative HPLC (phenomenex gemini column) with a gradient of acetonitrile:water). Colorless foam (18%). MS (Turbo Spray): m/z=555.2 [M+H].

Example 130

6-{2-[2-(4-Chloro-phenyl)-5,6-difluoro-benzoimidazol-1-yl]-2-cycloheptyl-ethoxy}-nicotinic acid The title compound was prepared in analogy to Example 4, from 6-{2-[2-(4-chloro-phenyl)-5,6-difluoro-benzoimidazol-1-yl]-2-cycloheptyl-ethoxy}-nicotinic acid methyl ester. Colorless solid (95%). MS (Turbo Spray): m/z=526.1 [M+H].
Intermediate

6-{2-[2-(4-Chloro-phenyl)-5,6-difluoro-benzoimidazol-1-yl]-2-cycloheptyl-ethoxy}-nicotinic acid methyl ester The title compound was prepared in analogy to Example 4, intermediate, from 2-[2-(4-chloro-phenyl)-5,6-difluoro-benzoimidazol-1-yl]-2-cyclohexyl-ethanol (Example 1, intermediate c), methyl 6-hydroxynicotinate (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30) to give the desired compound as a colorless solid (78%). MS (Turbo Spray): m/z=540.3 [M+H].

Example 131

4-{2-[2-(4-Chloro-phenyl)-5,6-difluoro-benzoimidazol-1-yl]-2-cycloheptyl-ethoxy}-3,5-difluoro-benzoic acid The title compound was prepared in analogy to Example 4, from 4-{2-[2-(4-Chloro-phenyl)-5,6-difluoro-benzoimidazol-1-yl]-2-cycloheptyl-ethoxy}-3,5-difluoro-benzoic acid methyl ester. Colorless solid (78%). MS (Turbo Spray): m/z=561.2 [M+H].
Intermediates a) 4-{2-[2-(4-Chloro-phenyl)-5,6-difluoro-benzoimidazol-1-yl]-2-cycloheptyl-ethoxy}-3,5-difluoro-benzoic acid methyl ester The title compound was prepared in analogy to Example 4, intermediate, from 2-[2-(4-chloro-phenyl)-5,6-difluoro-benzoimidazol-1-yl]-2-cycloheptyl-ethanol (Example 1, intermediate c), 3,5-difluoro-4-hydroxy-benzoic acid methyl ester (commercially available), triphenylphosphine and di-tert-butyl azodicarboxylate. The compound was purified by silica gel chromatography using a MPLC system (CombiFlash Companion, Isco Inc.) eluting with a gradient of n-heptane:ethyl acetate (100:0 to 70:30). Colorless solid. MS (Turbo Spray): 575.4 (M+H).

b) 2-[2-(4-Chloro-phenyl)-5,6-difluoro-benzoimidazol-1-yl]-2-cycloheptyl-ethanol To a solution of 1.4 g (3.13 mmol) [2-(4-chloro-phenyl)-5,6-difluoro-benzoimidazol-1-yl]-cycloheptyl-acetic acid ethyl ester in 20 ml dry tetrahydrofuran was added 0.125 g (3.29 mmol) lithium aluminum hydride at 0° C. The reaction mixture was stirred for 2 hours at room temperature and then poured on 100 ml 10% aqueous sodium-potassium-tartrate solution and 100 ml ethyl acetate. The aqueous layers were extracted again with 100 ml ethyl acetate. The organic layers were washed with 100 ml brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate (2:1). Colorless solid (74%). MS (TurboSpray): 405.3 [M+H].

c) [2-(4-Chloro-phenyl)-5,6-difluoro-benzoimidazol-1-yl]-cycloheptyl-acetic acid ethyl ester To a solution of 2.2 g (8.31 mmol) 2-(4-chloro-phenyl)-5,6-difluoro-1H-benzoimidazole (Example 1, intermediate a) in 22 ml N,N-dimethyl formamide was added 3.2 g (9.89 mmol) cesium carbonate and 2.6 g (9.89 mmol) bromo-cycloheptyl-acetic acid ethyl ester. The reaction mixture was stirred at 100° C. for 1 hour. Then, 3.2 g (9.89 mmol) cesium carbonate and 2.6 g (9.89 mmol) bromo-cycloheptyl-acetic acid ethyl ester were added. Stirring was continued at 100° C. for another 6 hours. Another 3.2 g (9.89 mmol) cesium carbonate and 2.6 g (9.89 mmol) bromo-cycloheptyl-acetic acid ethyl ester were added and the reaction mixture was stirred at 100° C. for 18 hours. The reaction mixture was poured on 200 ml water and 200 ml ethyl acetate and the layers were separated. The aqueous layer was extracted a second time with 200 ml ethyl acetate. The organic layers were washed with 200 ml brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate (100:0 to 60:40). Light yellow solid (63%). MS (Turbo Spray): m/z=447.2 [M+H].

d) Bromo-cycloheptyl-acetic acid ethyl ester

A solution of 4.0 g (25.604 mmol) cycloheptyl acetic acid (commercially available) in 3.81 ml (52.49 mmol) thionylchloride was stirred under reflux for 1 hour. To this solution was added 2.70 ml (52.49 mmol) bromine at room temperature. The reaction mixture was stirred for 5 hours at reflux temperature. The heating was removed and the reaction mixture was stirred at room temperature for 18 hours. The solution was cooled down to 0° C. and 20 ml ethanole were added dropwise. After stirring for 2 hours at room temperature the reaction mixture was poured on 300 ml 1M aqueous sodium hydroxide solution and 300 ml ethyl acetate and the layers were separated. The organic layer was washed a second time with 300 ml 1M aqueous sodium hydroxide solution and 300 ml brine. The aqueous layers were extracted a second time with 300 ml ethyl acetate. The organic layer were dried with magnesium sulfate, filtered and concentrated under vacuum. The so-obtained compound was pure enough for the next step without further purification. MS (GC Split): m/z=183 [M−Br].

Examples 132 and 133

The title compounds were obtained by separation of the stereoisomers of 4-{2-[2-(4-chloro-phenyl)-5,6-difluoro-benzoimidazol-1-yl]-2-cycloheptyl-ethoxy}-3,5-difluoro-benzoic acid (Examples 132) by chiral preparative HPLC (Chiralpak AD) eluting with n-heptane/15% ethanol (containing 0.5% formic acid).

(−)-4-{2-[2-(4-Chloro-phenyl)-5,6-difluoro-benzoimidazol-1-yl]-2-cycloheptyl-ethoxy}-3,5-difluoro-benzoic acid Colorless solid. MS (Turbo Spray): m/z=561.1 [M+H].

(+)-4-{2-[2-(4-Chloro-phenyl)-5,6-difluoro-benzoimidazol-1-yl]-2-cycloheptyl-ethoxy}-3,5-difluoro-benzoic acid Colorless solid. MS (Turbo Spray): m/z=561.1 [M+H].

Example 134

2-(4-Chloro-phenyl)-1-{1-(4,4-difluoro-cyclohexyl)-2-[2,6-dimethyl-4-(1H-tetrazol-5-yl)-phenoxy]-ethyl}-5,6-difluoro-1H-benzoimidazole To a solution of 0.16 g (0.29 mmol) 4-[2-[2-(4-chloro-phenyl)-5,6-difluoro-benzoimidazol-1-yl]-2-(4,4-difluoro-cyclohexyl)-ethoxy]-3,5-dimethyl-benzonitrile in 4 ml o-xylene were added 0.198 g (1.44 mmol) triethylamine hydrochloride and 0.094 g (1.45 mmol) sodium azide and heated for 21 h at 150° C. (oil bath temperature). Another 0.198 g (1.44 mmol) triethylamine hydrochloride and 0.094 g (1.45 mmol) sodium azide were added and the reaction mixture was heated for another 4 h and after cooling down to room temperature stirred 3 days. The reaction was then poured onto 1M aqueous hydrochloric acid solution, the phases were separated and the aqueous phase extracted three times with ethyl acetate. The combined organic layers were washed with brine, dried over magnesium sulfate, filtered and evaporated. The solid was suspended in acetonitrile, filtered, washed with acetonitrile and dried under high vacuum. White solid (77%). MS (Turbo Spray): m/z=599.194 [M+H].

Intermediates a) 4-[2-[2-(4-Chloro-phenyl)-5,6-difluoro-benzoimidazol-1-yl]-2-(4,4-difluoro-cyclohexyl)-ethoxy]-3,5-dimethyl-benzonitrile The title compound was prepared in analogy to Example 4, intermediate, from 2-[2-(4-chloro-phenyl)-5,6-difluoro-benzoimidazol-1-yl]-2-(4,4-difluoro-cyclohexyl)-ethanol, 3,5-dimethyl-4-hydroxybenzonitrile (commercially available), tri-n-butylphosphine and N'N'N'N-tetramethylazodicarboxamide. The compound was purified by silica gel chromatography using a MPLC system (CombiFlash Companion, Isco Inc.) eluting with a gradient of a gradient of heptane:ethyl b) 2-[2-(4-Chloro-phenyl)-5,6-difluoro-benzoimidazol-1-yl]-2-(4,4-difluoro-cyclohexyl)-ethanol To an ice-cold solution of 1.18 g (2.68 mmol) [2-(4-chloro-phenyl)-5,6-difluoro-benzoimidazol-1-yl]-(4,4-difluoro-cyclohexyl)-acetic acid in 20 ml tetrahydrofuran was added 0.15 g (4.01 mmol) lithium aluminium hydride. After removal of the cooling bath the reaction mixture was stirred for 1.25 h at room temperature. The reaction mixture was poured onto 100 ml aqueous saturated potassium sodium tartrate solution, the phases were separated and the aqueous layer was extracted three times with ethyl acetate. The combined organic layers were washed with brine, dried over magnesium sulfate, filtered and evaporated. The remaining oil was purified by silica gel chromatography using a MPLC system (CombiFlash Companion, Isco Inc.) eluting with a gradient of heptane:ethyl acetate (100:0 to 50:50). Light yellow solid (39%). MS (Turbo Spray): m/z=427.1 [M+H].

c) [2-(4-Chloro-phenyl)-5,6-difluoro-benzoimidazol-1-yl]-(4,4-difluoro-cyclohexyl)-acetic acid To a suspension of 3.05 g (5.46 mmol) N-benzyl-N-nitroso-2-[2-(4-chloro-phenyl)-5,6-difluoro-benzoimidazol-1-yl]-2-(4,4-difluoro-cyclohexyl)-acetamide in 15 ml tetrahydrofuran and 10 ml water were added dropwise over 5 min. a solution of 2.29 g (54.57 mmol) lithium hydroxide monohydrate in 11.14 ml (109 mmol) 30% hydrogen peroxide solution and 10 ml water. The reaction mixture turned into a turbid solution and became slightly warm (cooled temporarily using an ice-bath). After stirring for 2 h the pH was adjusted to pH 4 using 12.48 ml (218 mmol) acetic acid. The resulting light yellow solution was extracted three times with ethyl acetate. The combined organic layers were washed twice with saturated aqueous sodium bicarbonate solution, brine, dried over magnesium sulfate, filtered and evaporated. The remaining yellow foam was treated with 100 ml tert-butyl methylether and the resulting light yellow suspension was filtered, washed with tert-butyl methyl ether and dried under high vacuum to give a first batch of compound (yellow solid). The mother liquor was purified on a preparative HPLC system (Phenomenex Gemini column) eluting with a gradient of acetonitrile and water. to give another batch of compound (colorless solid). Overall yield 49%. MS (Turbo Spray): m/z=441.3 [M+H].

d) N-Benzyl-N-nitroso-2-[2-(4-chloro-phenyl)-5,6-difluoro-benzoimidazol-1-yl]-2-(4,4-difluoro-cyclohexyl)-acetamide To a ice-cold solution of 3.10 g (5.85 mMol) N-benzyl-2-[2-(4-chloro-phenyl)-5,6-difluoro-benzoimidazol-1-yl]-2-(4,4-difluoro-cyclohexyl)-acetamide in 19.1 ml (333 mmol) acetic acid and 40.14 ml (708 mmol) acetic anhydride were added in portions over 20 min. 2.02 g (29.25 mmol) sodium nitrite. The reaction mixture was stirred overnight at room temperature and evaporated. The residue was taken up in saturated aqueous sodium bicarbonate solution and ethyl acetate and the pH was adjusted to 7 by adding solid sodium bicarbonate. The aqueous layer was extracted twice with ethyl acetate and the combined organic layers were washed with brine, dried over magnesium sulfate, filtered and evaporated to dryness. Yellow foam (85%). MS (Turbo Spray): m/z=559.2 [M+H].

e) N-Benzyl-2-[2-(4-chloro-phenyl)-5,6-difluoro-benzoimidazol-1-yl]-2-(4,4-difluoro-cyclohexyl)-acetamide To a solution of 3.8 g (15.56 mmol) (2-amino-4,5-difluoro-phenyl)-carbamic acid tert-butyl ester (Example 73, intermediate g) in 38 ml methanol, 2.54 g (17.12 mmol) 4,4-difluorocyclohexanone (commercially available) were added. After stirring for 5 min. at room temperature the solution was treated with 2.44 g (15.58 mmol) p-chlorobenzoic acid, followed by an addition of 1.9 ml (15.56 mmol) benzyl isocyanide (commercially available). To the viscous slurry 12 ml methanol were added and the reaction for 22.5 h. Then 19.45 ml (77.80 mmol) 4M hydrochloric acid in dioxane were added dropwise over 5 min. After 4.5 h another 19.45 ml (77.80 mmol) 4M hydrochloric acid in dioxane were added. After 24 h, the suspension was poured onto 300 ml aqueous saturated sodium bicarbonate solution and the phases were separated. The aqueous layer was extracted three times with ethyl acetate and the organic layers were washed with brine, dried over magnesium sulfate, filtered, and evaporated. The residue was purified by silica gel chromatography using a MPLC system (CombiFlash Companion, Isco Inc.) eluting with a gradient of heptane:ethyl acetate (100:0 to 50:50). Light yellow solid (76%). MS (Turbo Spray): m/z=530.2 [M+H].

Example 135

2-(4-Chloro-phenyl)-1-{1-cyclopentyl-2-[2,6-dimethyl-4-(1H-tetrazol-5-yl)-phenoxy]-ethyl}-5,6-difluoro-1H-benzoimidazole To a solution of 0.17 g (0.34 mmol) 4-{2-[2-(4-chloro-phenyl)-5,6-difluoro-benzoimidazol-1-yl]-2-cyclopentyl-ethoxy}-3,5-dimethyl-benzonitrile in 4 ml o-xylene, were added 0.231 g (1.68 mmol) triethylamine hydrochloride and 0.109 g (1.68 mmol) sodium azide and the solution was heated at 150° C. (oil bath temperature) for 19.5 h. Another 0.231 g (1.68 mmol) triethylamine hydrochloride and 0.109 g (1.68 mmol) sodium azide were added and the reaction mixture was heated for an additional 4 h, then stirred for 3 days at room temperature. The reaction mixture was poured onto aqueous 1M hydrochloric acid solution, the phases were separated and the aqueous phase extracted three times with ethyl acetate. The combined organic layers were washed with brine, dried over magnesium sulfate, filtered and evaporated. The residue was suspended in acetonitrile, filtered and washed with acetonitrile. The obtained crude material was purified on a preparative HPLC (Zorbax column) eluting with a gradient of acetonitrile and water containing 0.5% formic acid. White solid (18%). MS (Turbo Spray): m/z=549.199 [M+H].

Intermediates a) 4-{2-[2-(4-Chloro-phenyl)-5,6-difluoro-benzoimidazol-1-yl]-2-cyclopentyl-ethoxy}-3,5-dimethyl-benzonitrile The title compound was prepared in analogy to Example 4, intermediate, from 2-[2-(4-chloro-phenyl)-5,6-difluoro-benzoimidazol-1-yl]-2-cyclopentyl-ethanol, 3,5-dimethyl-4-hydroxybenzonitrile (commercially available), tri-n-butylposphine and N'N'N'N-tetramethylazodicarboxamide. The compound was purified by silica gel chromatography using a MPLC system (CombiFlash Companion, Isco Inc.) eluting with a gradient of n-heptane:ethyl acetate (100:0 to 60:40).

The product containing fractions were pooled and evaporated. The resulting light yellow foam was dissolved in acetonitrile, upon which crystallisation occurred. The suspension was filtered, washed with a small amount of acetonitrile and dried under high vacuum. White solid (34%). MS (Turbo Spray): m/z=506.182 [M+H].

b) 2-[2-(4-Chloro-phenyl)-5,6-difluoro-benzoimidazol-1-yl]-2-cyclopentyl-ethanol To an ice-cold solution of 2.0 g (5.12 mmol) [2-(4-chloro-phenyl)-5,6-difluoro-benzoimidazol-1-yl]-cyclopentyl-acetic acid in 55 ml tetrahydrofuran were added in portions 0.29 g (7.64 mmol) lithium aluminium hydride. After removal of the cooling bath the reaction mixture was stirred for 2.5 h at room temperature and then poured onto 200 ml saturated aqueous tartrate solution. The phases were separated and the aqueous layer extracted three times with ethyl acetate. The combined organic layers were washed with brine, dried over magnesium sulfate, filtered and evaporated. The residue was purified by silica gel chromatography using a MPLC system (CombiFlash Companion, Isco Inc.) eluting with a gradient of heptane:ethyl acetate (100:0 to 50:50). Yellow solid (68%). MS (Turbo Spray): m/z=377.2 [M+H].

c) [2-(4-Chloro-phenyl)-5,6-difluoro-benzoimidazol-1-yl]-cyclopentyl-acetic acid To a ice-cold suspension of 8.10 g (15.91 mmol) N-benzyl-N-nitroso-2-[2-(4-chloro-phenyl)-5,6-difluoro-benzoimidazol-1-yl]-2-cyclopentyl-acetamide in 45 ml tetrahydrofuran and ml water were added dropwise over 30 min. a solution of 6.68 g (159 mmol) lithium hydroxide monohydrate in 32.50 ml (318 mmol) 30% hydrogen peroxide solution and 15 ml water. After stirring for 4.5 h at room temperature, 150 ml water and 100 ml ethyl acetate were added and the pH adjusted to 1 using 25% aqueous hydrochloric acid. The phases were separated and the aqueous phase extracted three times with ethyl acetate. The combined organic layers were washed with saturated aqueous sodium bicarbonate solution and brine, then dried over magnesium sulfate, filtered and evaporated. The residue was purified by silica gel chromatography using a MPLC system (CombiFlash Companion, Isco Inc.) eluting with a gradient of heptane:ethyl acetate:methanole (100:0:0 to 0:100:0 to 0:85:15). Off-white solid (55%). MS (Turbo Spray): m/z=391.1 [M+H].

d) N-Benzyl-N-nitroso-2-[2-(4-chloro-phenyl)-5,6-difluoro-benzoimidazol-1-yl]-2-cyclopentyl-acetamide To a ice-cold solution of 9.50 g (19.79 mmol) N-benzyl-2-[2-(4-chloro-phenyl)-5,6-difluoro-benzoimidazol-1-yl]-2-cyclopentyl-acetamide in 64.53 ml (1128 mmol) acetic acid and 135.84 ml (2395 mmol) acetic anhydride were added in portions over 60 min. 6.83 g (99 mmol) sodium nitrite. The reaction mixture was stirred for 1 h in an ice-bath, then at room temperature overnight. The mixture was evaporated and the residue was taken up in saturated aqueous sodium bicarbonate solution and ethyl acetate and solid sodium bicarbonate was added to adjust the pH to 7. The aqueous layer was extracted twice with ethyl acetate and the combined organic layers were washed with brine, dried over magnesium sulfate, filtered and evaporated. The remaining brown foam was purified by silica gel chromatography using a MPLC system (CombiFlash Companion, Isco Inc.) eluting with a gradient of heptane and ethyl acetate (100:0 to 50:50). Yellow solid (72%). MS (Turbo Spray): m/z=509.2 [M+H].

e) N-Benzyl-2-[2-(4-chloro-phenyl)-5,6-difluoro-benzoimidazol-1-yl]-2-cyclopentyl-acetamide To a solution of 5.0 g (20.47 mmol) (2-amino-4,5-difluoro-phenyl)-carbamic acid tert-butyl ester (Example 73, intermediate g) in 50 ml methanol, 2.21 g (22.57 mmol) cyclopentanecarbaldehyde (commercially available) were added. After stirring for 5 min. at room temperature, 3.2 g (20.5 mmol) p-chlorobenzoic acid and 2.5 ml (20.47 mmol) benzyl isocyanide (commercially available) were added. After stirring for 19 h, 38.38 ml (153.52 mmol) 4 M hydrochloric acid in dioxane were added dropwise over 5 min. After 5 h the solution was poured on 500 ml saturated aqueous sodium bicarbonate solution and the phases were separated. The organic layer was extracted three times with ethyl acetate and the combined organic layers were washed with water and brine, dried over magnesium sulfate, filtered, and evaporated. The residue was purified by silica gel chromatography using a MPLC system (CombiFlash Companion, Isco Inc.) eluting with a gradient of n-heptane:ethyl acetate (100:0 to 50:50). Light yellow foam (97%). MS (Turbo Spray): m/z=480.1 [M+H].

Example 136

2-(4-Chloro-phenyl)-1-{1-cyclopropyl-2-[2,6-dimethyl-4-(1H-tetrazol-5-yl)-phenoxy]-ethyl}-5,6-difluoro-1H-benzoimidazole The title compound was prepared in analogy to Example 56, from 4-{2-[2-(4-chloro-phenyl)-5,6-difluoro-benzoimidazol-1-yl]-2-cyclopropyl-ethoxy}-3,5-dimethyl-benzonitrile. Colorless solid (83%). MS (Turbo Spray): m/z=521.168 [M+H].
Intermediates a) 4-{2-[2-(4-Chloro-phenyl)-5,6-difluoro-benzoimidazol-1-yl]-2-cyclopropyl-ethoxy}-3,5-dimethyl-benzonitrile The title compound was prepared from 2-[2-(4-Chloro-phenyl)-5,6-difluoro-benzoimidazol-1-yl]-2-cyclopropyl-ethanol, 3,5-dimethyl-4-hydroxybenzonitrile (commercially available), tri-n-butylposphine and N'N'N'N-tetramethylazodicarboxamide. The compound was purified by silica gel chromatography using a MPLC system (CombiFlash Companion, Isco Inc.) eluting with a gradient of heptane:ethyl acetate (100:0 to 60:40). The so-obtained solid was again chromatographed on a preparative HPLC system using a Phenomenex Gemini column eluting with a gradient of acetonitril and water (containing 5% formic acid). White foam (20%). MS (Turbo Spray): m/z=478.149 [M+H].

b) 2-[2-(4-Chloro-phenyl)-5,6-difluoro-benzoimidazol-1-yl]-2-cyclopropyl-ethanol To an ice-cold suspension of 3.0 g (8.27 mmol) [2-(4-chloro-phenyl)-5,6-difluoro-benzoimidazol-1-yl]-cyclopropyl-acetic acid in 105 ml tetrahydrofuran were added in portions 0.47 g (12.4 mmol) lithium aluminium hydride. After removal of the cooling bath the reaction mixture was stirred for 1 h at room temperature. The reaction mixture was poured onto 200 ml potassium sodium tartrate solution wan was extracted three times with ethyl acetate. The combined organic layers were washed with brine, dried over magnesium sulfate, filtered and evaporated to give a yellow solid which was purified by silica gel chromatography using a MPLC system (CombiFlash Companion, Isco Inc.) eluting with a gradient of heptane:ethyl acetate (100:0 to 50:50). The product containing fractions were pooled and evaporated until precipitation started. The suspension was filtered and washed with n-heptane to give the desired compound as an off-white solid (56%). MS (Turbo Spray): m/z=349.2 [M+H].

c) [2-(4-Chloro-phenyl)-5,6-difluoro-benzoimidazol-1-yl]-cyclopropyl-acetic acid To a ice-cold suspension of 10.15 g (21.11 mmol) N-benzyl-N-nitroso-2-[2-(4-chloro-phenyl)-5,6-difluoro-benzoimidazol-1-yl]-2-cyclopropyl-acetamide in 60 ml tetrahydrofuran and 15 ml water were added dropwise over 30 min. a solution of 8.86 g (211 mmol) lithium hydroxide monohydrate in 43.1 ml (422 mmol) hydrogen peroxide 30% solution and 30 ml water. After stirring for 2.25 h at room temperature the pH was adjusted to 3 using 70 ml acetic acid and 25% aqueous hydrochloric acid. The resulting light yellow solution was extracted three times with ethyl acetate. The organic layers were washed with water, aqueous saturated sodium bicarbonate solution and brine. After drying over magnesium sulfate and filtration, the solution was evaporated until a suspension formed. This suspension was filtered and washed with ethyl acetate to give the compound as a white solid (56%). MS (Turbo Spray): m/z=363.2 [M+H].

d) N-Benzyl-N-nitroso-2-[2-(4-chloro-phenyl)-5,6-difluoro-benzoimidazol-1-yl]-2-cyclopropyl-acetamide To a ice-cold solution of 13.15 g (29.1 mmol) N-benzyl-2-[2-(4-chloro-phenyl)-5,6-difluoro-benzoimidazol-1-yl]-2-cyclopropyl-acetamide in 95 ml (1.659 mol) acetic acid and 199.7 ml (3.52 Mol) acetic anhydride were added in portions over 60 min. 10.04 g (145 mmol) sodium nitrite. The reaction mixture was stirred for 1 h at 0° C., then at room temperature overnight. The mixture was evaporated and the residue was taken up in saturated aqueous sodium bicarbonate solution and ethyl acetate and the pH was adjusted to 7 with solid sodium bicarbonate. The aqueous layer was extracted twice with ethyl acetate. The combined organic layers were washed with brine, dried over magnesium sulfate, filtered and evaporated to dryness. The residue was purified by silica gel column chromatography using a MPLC system (CombiFlash Companion, Isco Inc.) eluting with a gradient of n-heptane:ethyl acetate (100:0 to 50:50) to give the desired compound as a light yellow solid (53%). MS (Turbo Spray): m/z=481.1 [M+H].

e) N-Benzyl-2-[2-(4-chloro-phenyl)-5,6-difluoro-benzoimidazol-1-yl]-2-cyclopropyl-acetamide To a solution of 7.2 g (29.48 mmol) (2-amino-4,5-difluoro-phenyl)-carbamic acid tert-butyl ester (Example 73, intermediate g) in 75 ml methanole, 2.48 g (35.37 mmol) cyclopropanecarbaldehyde (commercially available) were added. After stirring for 5 min. at room temperature the solution was treated with 4.62 g (29.5 mmol) 4-chlorobenzoic acid (commercially available), followed by an addition of 3.6 ml (29.47 mmol) benzylisocyanide (commercially available). The formed solution was stirred at room temperature for 23 h, then 36.85 ml (147 mmol) 4 M hydrochloric acid in dioxane were added dropwise over 5 min. The resulting suspension was stirred for 23 h, then poured onto 500 ml saturated aqueous sodium bicarbonate solution. The aqueous layer was extracted three times with ethyl acetate. The combined organic layers were washed with water and brine, dried over magnesium sulfate, filtered, and evaporated. The residue was purified by silica gel column chromatography using a MPLC system (CombiFlash Companion, Isco Inc.) eluting with a gradient of heptane:ethyl acetate (100:0 to 50:50). Light yellow solid (99%). MS (Turbo Spray): m/z=452.1 [M+H].

Examples 137 and 138

The title compounds were prepared in analogy to Example 4, from (+) or (−)-4-{2-[2-(4-chloro-phenyl)-5,6-difluoro-benzoimidazol-1-yl]-(2-cis-cyclohexyl-ethylamino}-cyclohexanecarboxylic acid ethyl ester and (+) or (−)-4-{2-[2-(4-chloro-phenyl)-5,6-difluoro-benzoimidazol-1-yl]-(2-trans-cyclohexyl-ethylamino}-cyclohexanecarboxylic acid ethyl ester, respectively. The pH of the aqueous layer was adjusted to 1 and extracted three times with ethyl acetate. The combined organic layers were washed with brine, dried over magnesium sulfate, filtered and evaporated.

The residue was purified on a preparative HPLC system using a Phenomenex Gemini column eluting with a gradient of acetonitril and water (containing 0.5% formic acid).

(+) or (−)-4-{2-[2-(4-Chloro-phenyl)-5,6-difluoro-benzoimidazol-1-yl]-(2-cis-cyclohexyl-ethylamino}-cyclohexanecarboxylic acid Colorless foam. MS (Turbo Spray): m/z=516.3 [M+H].

(+) or (−)-4-{2-[2-(4-Chloro-phenyl)-5,6-difluoro-benzoimidazol-1-yl]-(2-trans-cyclohexyl-ethylamino}-cyclohexanecarboxylic acid Colorless foam. MS (Turbo Spray): m/z=516.3 [M+H].

Intermediates a) (+) or (−)-4-{2-[2-(4-Chloro-phenyl)-5,6-difluoro-benzoimidazol-1-yl]-(2-cis-cyclohexyl-ethylamino}-cyclohexanecarboxylic acid ethyl ester and (+) or (−)-4-{2-[2-(4-chloro-phenyl)-5,6-difluoro-benzoimidazol-1-yl]-(2-trans-cyclohexyl-ethylamino}-cyclohexanecarboxylic acid ethyl ester To a solution of 0.008 g (0.026 mmol) dibutyltin dichloride in 1 ml tetrahydrofuran were added 0.10 g (0.26 mmol) (−)-2-[2-(4-chloro-phenyl)-5,6-difluoro-benzoimidazol-1-yl]-2-cyclohexyl-ethylamine, 0.044 g (0.26 mmol) ethyl 4-oxocyclohexanecarboxylate (commercially available) and 0.06 ml (0.52 mmol) phenylsilane. The pale yellow solution was heated to 100° C. under microwave irradiation for 7 min. The reaction mixture was treated with silica gel and the slurry evaporated to dryness and stored at 4° C. overnight. The residue was purified and the isomers separated by silica gel chromatography using a MPLC system (CombiFlash Companion, Isco Inc.) eluting with a gradient of n-heptane:ethyl acetate (100:0 to 60:40).

(+) or (−)-4-{2-[2-(4-Chloro-phenyl)-5,6-difluoro-benzoimidazol-1-yl]-(2-cis-cyclohexyl-ethylamino}-cyclohexanecarboxylic acid ethyl ester and Colorless foam. MS (Turbo Spray): m/z=544.3 [M+H].

(+) or (−)-4-{2-[2-(4-chloro-phenyl)-5,6-difluoro-benzoimidazol-1-yl]-(2-trans-cyclohexyl-ethylamino}-cyclohexanecarboxylic acid ethyl ester Light brown waxy solid. MS (Turbo Spray): m/z=544.3 [M+H].

b) (−)-2-[2-(4-Chloro-phenyl)-5,6-difluoro-benzoimidazol-1-yl]-2-cyclohexyl-ethylamine To a solution of 0.93 g (2.3 mmol) (+) or (−)-2-[2-(4-chloro-phenyl)-5,6-difluoro-benzoimidazol-1-yl]-2-cyclohexyl-acetamide in tetrahydrofuran were added 0.29 ml (2.3 mmol) boron trifluoride ethyl etherate. The mixture was stirred for 5 min. and then 4.61 ml (4.61 mmol) borane THF complex (1M solution in tetrahydrofuran) were added dropwise. The mixture was stirred at 50° C. for 55 h. The solution was poured onto 12 ml tetrahydrofuran and 5 ml methanol (gas evolution) and stirred for 1 h. Then 50 ml 1M aqueous hydrochloric acid were added and the layers were separated. The aqueous phase was extracted twice with ethyl acetate and the combined organic layers were washed with 10 ml 1M aqueous hydrochloric acid. The combined aqueous layers were adjusted to pH 10 using 32% aqueous sodium hydroxide and 1M aqueous sodium hydroxide solution. The turbid mixture was extracted three times with dichloromethane. The organic layers were washed with brine, dried over magnesium sulfate and evaporated to dryness. White foam (22%). MS (Turbo Spray): m/z=390.3 [M+H].

c) (+) or (−)-2-[2-(4-Chloro-phenyl)-5,6-difluoro-benzoimidazol-1-yl]-2-cyclohexyl-acetamide To a turbid solution of 1 g (2.47 mMol) (−)-[2-(4-chloro-phenyl)-5,6-difluoro-benzoimidazol-1-yl]-cyclohexyl-acetic acid in 15 ml N,N-dimethyl formamide were added 0.264 g (4.94 mmol) ammonium chloride, 0.42 ml (2.47 mmol) ethyl diisopropylamine, 0.378 g (2.47 mmol) N-hydroxybenzotriazole monohydrate and 0.947 g (4.94 mmol) N-(3-dimethylaminopropyl)-N'-ethylcarbodiimide hydrochloride. The reaction mixture is stirred for 14 h at room temperature and then poured onto water. The phases were separated and the aqueous phase extracted three times with ethyl acetate. The combined organic layers were twice washed with water, once with brine, dried over magnesium sulfate, filtered and evaporated. The residue was purified by silica gel column chromatography using a MPLC system (CombiFlash Companion, Isco Inc.) eluting with ethyl acetate. Colorless solid (93%). MS (Turbo Spray): m/z=404.3 [M+H].

d) (+) and (−)-[2-(4-Chloro-phenyl)-5,6-difluoro-benzoimidazol-1-yl]-cyclohexyl-acetic acid The title compounds were obtained by separation of the stereoisomers of [2-(4-chloro-phenyl)-5,6-difluoro-benzoimidazol-1-yl]-cyclohexyl-acetic acid by chiral preparative HPLC (Chiralpak AD) eluting with n-heptane/5% ethanol (containing 0.5% trifluoroacetic acid).

(−)-[2-(4-Chloro-phenyl)-5,6-difluoro-benzoimidazol-1-yl]-cyclohexyl-acetic acid Colorless solid. MS (Turbo Spray): m/z=403.3 [M−H].

(+)-[2-(4-Chloro-phenyl)-5,6-difluoro-benzoimidazol-1-yl]-cyclohexyl-acetic acid Colorless solid. MS (Turbo Spray): m/z=403.3 [M−H].

e) [2-(4-Chloro-phenyl)-5,6-difluoro-benzoimidazol-1-yl]-cyclohexyl-acetic acid To the solution of 0.17 g (0.469 mmol) [2-(4-chloro-phenyl)-5,6-difluoro-benzoimidazol-1-yl]-cyclohexyl-acetic acid ethyl ester (Example 1, intermediate b) in 4 ml dioxan and 2 ml water, 34 mg (1.42 mmol) lithium hydroxide monohydrate were added and the reaction was stirred at reflux temperature for 2 h. After cooling to room temperature the solution was partially evaporated, diluted with 2 ml water and the pH was adjusted to 1-2 with 1M aqueous hydrochloric acid. The resulting suspension was stirred for 30 min. and then filtered. The filter cake was thoroughly washed with water and dried under high vacuum. Colorless solid (83%). MS (Turbo Spray): m/z=333.3 [M−H].

Example 139

{2-[2-(4-Chloro-phenyl)-5,6-difluoro-benzoimidazol-1-yl]-2-cyclohexyl-ethyl}-[4-(1H-tetrazol-5-yl)-phenyl]-amine To a suspension of 0.08 g (0.16 mmol) 4-{2-[2-(4-chloro-phenyl)-5,6-difluoro-benzoimidazol-1-yl]-2-cyclohexyl-ethylamino}-benzonitrile in 2 ml o-xylene were added 0.112 g (0.81 mMol) triethylamine hydrochloride and 0.053 g (0.82 mmol) sodium azide. The resulting mixture was heated to 145° C. After 72 h another 0.112 g (0.81 mMol) triethylamine hydrochloride and 0.053 g (0.82 mMol) sodium azide were added and the temperature of the oil bath was elevated to 160° C. After 24 h the oil bath was removed and the reaction mixture was poured on saturated aqueous ammonium chloride solution. The aqueous phase was extracted three times with ethyl acetate and the combined organic layers were washed with water and brine, dried over magnesium sulfate, filtered and evaporated. The resulting light brown solid was dissolved in ethyl acetate. Upon evaporation a suspension formed which was filtered and washed with ethyl acetate. The resulting solid was taken up in 2 ml acetonitrile, heated to reflux and then cooled down to 4° C. The suspension was filtered, the solid washed with acetonitrile and dried under high vacuum. Light brown solid (25%). MS (Turbo Spray): m/z=534.2 [M+H].
Intermediate

4-{2-[2-(4-Chloro-phenyl)-5,6-difluoro-benzoimidazol-1-yl]-2-cyclohexyl-ethylamino}-benzonitrile To a solution of 7 mg (0.023 mmol) dibutyltin dichloride in 1 ml tetrahydrofuran were added 0.10 g (0.23 mmol) [2-(4-chloro-phenyl)-5,6-difluoro-benzoimidazol-1-yl]-cyclohexyl-acetaldehyde (Example 143, intermediate c), 0.038 g (0.23 mMol) 4-aminobenzonitrile (commercially available) and 0.06 ml (0.46 mmol) phenylsilane (commercially available). The pale yellow solution was heated to 100° C. under microwave irradiation for 21 min. The light yellow solution was treated with silica gel and the suspension evaporated to dryness. The remaining solid was purified by silica gel chromatography using a MPLC system (CombiFlash Companion, Isco Inc.) eluting with a gradient of heptane:ethyl acetate (100:0 to 70:30). The fractions containing the product were pooled and chromatographed a second time under the same conditions to give the title compound as a white solid (67%). MS (Turbo Spray): m/z=491.2 [M+H].

Example 140

4-{2-[2-(4-Chloro-phenyl)-5,6-difluoro-benzoimidazol-1-yl]-2-cyclohexyl-ethylsulfanyl}-benzoic acid The title compound was prepared in analogy to Example 4, from 4-{2-[2-(4-chloro-phenyl)-5,6-difluoro-benzoimidazol-1-yl]-2-cyclohexyl-ethylsulfanyl}-benzoic acid methyl ester to give the title compound as a colorless solid (96%). MS (Turbo Spray): m/z=527.1 [M+H].
Intermediate 4-{2-[2-(4-Chloro-phenyl)-5,6-difluoro-benzoimidazol-1-yl]-2-cyclohexyl-ethylsulfanyl}-benzoic acid methyl ester To a solution of 74 mg (0.44 mmol) methyl 4-mercaptobenzoate in 3 ml N,N-dimethylformamide was added 61 mg (0.44 mmol) potassium carbonate at 0° C. The reaction mixture was stirred for 15 min. and then 200 mg (0.44 mmol) 1-(2-bromo-1-cyclohexyl-ethyl)-2-(4-chloro-phenyl)-5,6-difluoro-1H-benzoimidazole (Example 34, intermediate) was added at the same temperature. The cooling bath was removed and the reaction mixture stirred for 18 hours at room temperature. The reaction mixture was poured on 10% aqueous 30 ml citric acid and 30 ml ethyl acetate and the layers were separated. The aqueous layer was extracted a second time with 30 ml ethyl acetate. The combined organic layers were washed with 30 ml brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate (100:0 to 70:30) to give the desired compound as a colorless solid (65%). MS (Turbo Spray) m/z=541.2 [M+H].

Example 141

4-{2-[2-(4-Chloro-phenyl)-5,6-difluoro-benzoimidazol-1-yl]-2-cyclohexyl-ethanesulfonyl}-benzoic acid To a solution of 50 mg (0.095 mmol) 4-{2-[2-(4-chloro-phenyl)-5,6-difluoro-benzoimidazol-1-yl]-2-cyclohexyl-ethylsulfanyl}-benzoic acid (Example 141) in 2 ml dichloromethane was added 47 mg (0.19 mmol) 3-chloroperbenzoic acid (commercially available) at 0° C. The cooling bath was removed and the reaction mixture stirred for 3 h at room temperature. The reaction mixture was poured on 30 ml dichloromethane and 30 ml 10% aqueous sodium bicarbonate solution and the layers were separated. The aqueous layers were extracted a second time with 30 ml dichloromethane. The combined organic layers were washed with 30 ml brine, dried over magnesium sulfate, filtered and concentrated under vacuum. The residue was purified by silica gel chromatography using a MPLC system (CombiFlash Companion, Isco Inc.) eluting with a gradient of n-heptane:ethyl acetate:methanol (100:0 to 0:100:0 to 0:50:50) to give the title compound as a colorless solid (72%). MS (Turbo Spray): m/z=559.2 [M+H].

Example 142

4-[3-Cyclohexyl-3-(5,6-difluoro-2-phenyl-benzoimidazol-1-yl)-propyl]-benzoic acid To a solution of 115 mg (0.227 mmol) 4-{(E and Z)-3-[2-(4-chloro-phenyl)-5,6-difluoro-benzoimidazol-1-yl]-3-cyclohexyl-propenyl}-benzoic acid in 3 ml ethyl acetate was added 30 mg 5% palladium on carbon and 3 ml methanol. The reaction mixture was vigorously stirred for 2 h under a hydrogen atmosphere of 1.5 bar. The reaction mixture was filtered over dicalite and concentrated under vacuum. The residue was purified by preparative HPLC (phenomenex gemini column) eluting with a gradient of acetonitril:water (50:50 to 95:5) to give the title compound as a colorless solid (53%). MS (Turbo Spray): m/z=475.2 [M+H].
Intermediates a) 4-{(E and Z)-3-[2-(4-Chloro-phenyl)-5,6-difluoro-benzoimidazol-1-yl]-3-cyclohexyl-propenyl}-benzoic acid To a solution of 165 mg (0.317 mmol) 4-{(E and Z)-3-[2-(4-chloro-phenyl)-5,6-difluoro-benzoimidazol-1-yl]-3-cyclohexyl-propenyl}-benzoic acid methyl ester in 3 ml dioxane was added 3 ml water and 40 mg (0.950 mmol) lithium hydroxide monohydrate. The reaction mixture was stirred for 4 h at 90° C. Dioxane was removed under vacuum. Then 1.11 ml (1.108 mmol) 1N hydrochloric acid were added under stirring. The mixture was poured on 40 ml aqueous 1N hydrochloric acid and 40 ml ethyl acetate. The aqueous layer was extracted a second time with 40 ml ethyl acetate. The combined organic layers were washed with 40 ml brine, dried over magnesium sulfate, filtered and concentrated under vacuum. The residue was purified by silica chromatography using a MPLC system (CombiFlash Companion, Isco Inc.) eluting with a gradient of n-heptane:ethyl acetate:methanol (100:0:0 to 0:100:0 to 0:50:50) to give the desired compound as a colorless solid (77%). MS (Turbo Spray): m/z=507.2 [M+H].

b) 4-{(E and Z)-3-[2-(4-Chloro-phenyl)-5,6-difluoro-benzoimidazol-1-yl]-3-cyclohexyl-propenyl}-benzoic acid methyl ester To an ice-cooled solution of 278 mg (0.566 mmol) 4-carbomethoxybenzyl triphenylphosphonium bromide in 4 ml tetrahydrofuran was added 63 mg (0.566 mmol) potassium tert-butoxide. The reaction mixture was stirred for 15 min., then 220 mg (0.566 mmol) [2-(4-chloro-phenyl)-5,6-difluoro-benzoimidazol-1-yl]-cyclohexyl-acetaldehyde was added at 0° C. The reaction mixture was stirred for 4 h at room temperature. The reaction mixture was poured on 30 ml 10% aqueous citric acid and 30 ml ethyl acetate. The aqueous layer was separated and extracted a second time with 30 ml ethyl acetate. The combined organic layers were washed with 30 ml brine, dried over magnesium sulfate, filtered and concentrated under vacuum. The residue was purified by silica chromatography using a MPLC system (CombiFlash Companion, Isco Inc.) eluting with a gradient of n-heptane:ethyl acetate (100:0 to 70:30). MS (Turbo Spray): m/z=521.3 [M+H].

c) [2-(4-Chloro-phenyl)-5,6-difluoro-benzoimidazol-1-yl]-cyclohexyl-acetaldehyde To a solution of 200 mg (0.512 mmol) 2-[2-(4-chloro-phenyl)-benzoimidazol-1-yl]-2-cyclohexyl-ethanol (Ex. 1, intermediate c) in 2 ml dichloromethane was added 1.59 ml (2.17 g, 0.768 mmol) 1,1,1-tris(acetyloxy)-1,1-dihydro-1,2-benziodoxol-3-(1H)-one (Dess-Martin-periodinane; 15 wt % in dichloromethane). The reaction mixture was stirred for 2 h at room temperature and then poured onto 30 ml dichloromethane and 30 ml water. The aqueous layer were extracted again with 30 ml dichloromethane. The combined organic layers were washed with 30 ml brine, dried over magnesium sulfate, filtered and concentrated under vacuum. The residue was purified by silica chromatography using a MPLC system (CombiFlash Companion, Isco Inc.) eluting with a gradient of n-heptane:ethyl acetate (100:0 to 60:40) to give the product as a colorless solid (74%). MS (Turbo Spray): m/z=389.2 [M+H].

Examples 143 and 144

The title compounds were obtained by separation of the stereoisomers of 4-[3-cyclohexyl-3-(5,6-difluoro-2-phenyl-benzoimidazol-1-yl)-propyl]-benzoic acid (Example 143) by chiral preparative HPLC (Chiralpak AD) eluting with n-heptane/20% ethanol (containing 0.5% formic acid).

(−)-4-[3-Cyclohexyl-3-(5,6-difluoro-2-phenyl-benzoimidazol-1-yl)-propyl]-benzoic acid Light yellow solid. MS (Turbo Spray): m/z=475.1 [M+H].

(+)-4-[3-Cyclohexyl-3-(5,6-difluoro-2-phenyl-benzoimidazol-1-yl)-propyl]-benzoic acid Light yellow solid. MS (Turbo Spray): m/z=475.1 [M+H].

Example 145

4-{3-Cyclohexyl-3-[2-(2,6-dimethoxy-pyridin-3-yl)-5,6-difluoro-benzoimidazol-1-yl]-propyl}-benzoic acid To a solution of 180 mg (0.327 mmol) 4-{3-cyclohexyl-3-[2-(2,6-dimethoxy-pyridin-3-yl)-5,6-difluoro-benzoimidazol-1-yl]-propyl}-benzoic acid methyl ester in 3 ml dioxane was added 3 ml water and 41 mg (0.98 mmol) lithium hydroxide monohydrate. The reaction mixture was stirred for 4 h at 100° C. and then poured on 30 ml aqueous 1M hydrochloric acid and 30 ml ethyl acetate. The aqueous layer was extracted a second time with 30 ml ethyl acetate. The combined organic layers were washed with 30 ml brine, dried over magnesium sulfate, filtered and concentrated under vacuum. The residue was purified by preparative HPLC (phenomenex gemini column) eluting with a gradient of acetonitril:water (50:50 to 95:5) to give the title compound as a light yellow solid (78%). MS (Turbo Spray): m/z=536.236 [M+H].
Intermediates a) 4-{3-Cyclohexyl-3-[2-(2,6-dimethoxy-pyridin-3-yl)-5,6-difluoro-benzoimidazol-1-yl]-propyl}-benzoic acid methyl ester To a solution of 210 mg (0.383 mmol) 4-{(E)-3-cyclohexyl-3-[2-(2,6-dimethoxy-pyridin-3-yl)-5,6-difluoro-benzoimidazol-1-yl]-propenyl}-benzoic acid methyl ester in 4 ml methanol was added 30 mg Pd on carbon 5%. The reaction mixture was hydrogenated at 1.5 bar under vigorous stirring for 1 hour, then filtered over dicalite and concentrated under vacuum. Colorless oil (90%). MS (Turbo Spray): m/z=550.4 [M+H].

b) 4-{(E)-3-Cyclohexyl-3-[2-(2,6-dimethoxy-pyridin-3-yl)-5,6-difluoro-benzoimidazol-1-yl]-propenyl}-benzoic acid methyl ester To a solution of 296 mg (0.60 mmol) 4-carbomethoxybenzyl triphenylphosphonium bromide in 5 ml tetrahydrofuran was added 68 mg (0.602 mmol) potassium tert-butoxide at 0° C. and the reaction mixture was stirred for 15 min. Then, 250 mg (0.60 mmol) cyclohexyl-[2-(2,6-dimethoxy-pyridin-3-yl)-5,6-difluoro-benzoimidazol-1-yl]-acetaldehyde was added at 0° C. The cooling bath was removed and the reaction mixture was stirred for 4 hours at room temperature. The reaction was poured on 30 ml 10% aqueous citric acid and 30 ml ethyl acetate and the layers were separated. The aqueous layer was extracted a second time with 30 ml ethyl acetate. The combined organic layers were washed with 30 ml brine, dried over magnesium sulfate, filtered and concentrated under vacuum. The residue was purified by silica chromatography using a MPLC system (CombiFlash Companion, Isco Inc.) eluting with a gradient of n-heptane:ethyl acetate (100:0 to 70:30). Colorless solid (67%). MS (TurboSpray): m/z=547.2 [M+H].

c) Cyclohexyl-[2-(2,6-dimethoxy-pyridin-3-yl)-5,6-difluoro-benzoimidazol-1-yl]-acetaldehyde To a solution of 3.0 g (7.19 mmol) 2-cyclohexyl-2-[2-(2,6-dimethoxy-pyridin-3-yl)-5,6-difluoro-benzoimidazol-1-yl]-ethanol (Example 73, intermediate b) in 30 ml dichloromethane was added 30.48 g (10.78 mmol) 1,1,1-tris(acetyloxy)-1,1-dihydro-1,2-benziodoxol-3-(1H)-one (Dess-Martin-periodinane, 15 wt % in dichloromethane). The reaction mixture was stirred for 2 hours at room temperature. The reaction mixture was poured onto 300 ml dichloromethane and 300 ml water and the phases were separated. The aqueous layer was extracted with 300 ml dichloromethane. The combined organic layers were washed with 300 ml brine, dried over magnesium sulfate, filtered and concentrated under vacuum. The residue was purified by silica chromatography using a MPLC system (CombiFlash Companion, Isco Inc.) eluting with a gradient of n-heptane:ethyl acetate (100:0 to 60:40) to give the product as a colorless foam (74%). MS (Turbo Spray): m/z=416.4 [M+H].

Examples 146 and 147

The title compounds were obtained by separation of the stereoisomers of 4-{3-cyclohexyl-3-[2-(2,6-dimethoxy-pyridin-3-yl)-5,6-difluoro-benzoimidazol-1-yl]-propyl}-benzoic acid (Example 146) by chiral preparative HPLC (Chiralpak AD) eluting with n-heptane/10% ethanol (containing 0.5% formic acid).

(−)-4-{3-Cyclohexyl-3-[2-(2,6-dimethoxy-pyridin-3-yl)-5,6-difluoro-benzoimidazol-1-yl]-propyl}-benzoic acid MS (Turbo Spray): m/z=536.2 [M+H].

(+)-4-{3-Cyclohexyl-3-[2-(2,6-dimethoxy-pyridin-3-yl)-5,6-difluoro-benzoimidazol-1-yl]-propyl}-benzoic acid MS (Turbo Spray): m/z=536.2 [M+H].

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound of formula (I):

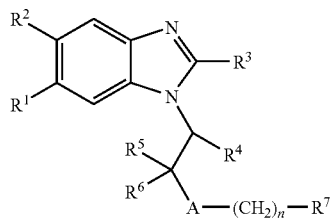

or a pharmaceutically acceptable salt or ester thereof, wherein:
A is oxygen, sulfur, $SO_2$, $CH_2$ or $NR^8$;
$R^1$ is hydrogen or halogen;
$R^2$ is hydrogen or halogen;
$R^3$ is phenyl or pyridinyl, wherein said phenyl or pyridinyl is optionally substituted with one to three substituents independently selected from the group consisting of alkyl, haloalkyl, alkoxy and halogen;
$R^4$ is cycloalkyl or halocycloalkyl;
$R^5$ and $R^6$ are independently hydrogen or alkyl; or alternatively $R^5$ and $R^6$ together with the carbon atom to which they are attached form cycloalkyl;
$R^7$ is cycloalkyl, phenyl, pyridinyl, pyrimidinyl, or thieno[2,3-c]pyridinyl; which is optionally substituted with one to three substituents independently selected from the group consisting of: (1) alkyl, (2) haloalkyl, (3) alkoxy, (4) carboxy, (5) carboxyalkoxy, (6) carboxycycloalkoxy, (7) halogen, (8) isoxazol-3-one-5-yl, (9) 1H-tetrazol-5-yl, (10) [1,2,4]oxadiazolidin-3,5-dione-2-yl, (11) thiazolidin-2,4-dione-5-yl, and (12) imidazolidin-2,4-dione-5-yl;
$R^8$ is hydrogen, alkyl or haloalkyl; and
n is 0 or 1.
2. A compound according to claim 1, wherein A is oxygen or $NR^8$.
3. A compound according to claim 1, wherein A is oxygen.
4. A compound according to claim 1, wherein $R^1$ is hydrogen or fluorine.
5. A compound according to claim 1, wherein $R^2$ is hydrogen or fluorine.
6. A compound according to claim 1, wherein $R^1$ and $R^2$ are both hydrogen or both fluorine at the same time.
7. A compound according to claim 1, wherein $R^3$ is phenyl, phenyl substituted with halogen or pyridinyl substituted with two alkoxy.
8. A compound according to claim 1, wherein $R^3$ is phenyl, chlorophenyl or dimethoxypyridinyl.
9. A compound according to claim 1, wherein $R^4$ is cyclopropyl, cyclopentyl, cyclohexyl, halocyclohexyl or cycloheptyl.
10. A compound according to claim 1, wherein $R^4$ is cyclohexyl or difluorocyclohexyl.
11. A compound according to claim 1, wherein $R^5$ and $R^6$ are both hydrogen or both methyl at the same time.
12. A compound according to claim 1, wherein $R^5$ and $R^6$ are both hydrogen at the same time.
13. A compound according to claim 1, wherein $R^7$ is cyclohexyl, phenyl or pyridinyl; which is substituted with one to three substituents independently selected from the group consisting of alkyl, haloalkyl, carboxy, carboxycycloalkoxy, halogen and 1H-tetrazol-5-yl.
14. A compound according to claim 1, wherein $R^7$ is cyclohexyl, phenyl or pyridinyl; which is substituted with one to three substituents independently selected from the group consisting of methyl, trifluoromethyl, carboxy, carboxycyclopropyloxy, chloro, fluoro, and 1H-tetrazol-5-yl.
15. A compound according to claim 1 wherein $R^8$ is hydrogen.
16. A compound according to claim 1 selected from the group consisting of:
2-(4-Chloro-phenyl)-1-(1-cyclohexyl-2-cyclohexyl-methoxy-ethyl)-5,6-difluoro-1H-benzoimidazole;
(−)-2-(4-Chloro-phenyl)-1-(1-cyclohexyl-2-cyclohexyl-methoxy-ethyl)-5,6-difluoro-1H-benzoimidazole;
(+)-2-(4-Chloro-phenyl)-1-(1-cyclohexyl-2-cyclohexyl-methoxy-ethyl)-5,6-difluoro-1H-benzoimidazole;
4-{2-[2-(4-Chloro-phenyl)-5,6-difluoro-benzoimidazol-1-yl]-2-cyclohexyl-ethoxy}-benzoic acid;
(+)-4-{2-[2-(4-Chloro-phenyl)-5,6-difluoro-benzoimidazol-1-yl]-2-cyclohexyl-ethoxy}-benzoic acid;
(−)-4-{2-[2-(4-Chloro-phenyl)-5,6-difluoro-benzoimidazol-1-yl]-2-cyclohexyl-ethoxy}-benzoic acid;
4-{2-[2-(4-Chloro-phenyl)-5,6-difluoro-benzoimidazol-1-yl]-2-cyclohexyl-ethoxy}-3-fluoro-benzoic acid;
(−)-4-{2-[2-(4-Chloro-phenyl)-5,6-difluoro-benzoimidazol-1-yl]-2-cyclohexyl-ethoxy}-3-fluoro-benzoic acid;
(+)-4-{2-[2-(4-Chloro-phenyl)-5,6-difluoro-benzoimidazol-1-yl]-2-cyclohexyl-ethoxy}-3-fluoro-benzoic acid;
3-Chloro-4-{2-[2-(4-chloro-phenyl)-5,6-difluoro-benzoimidazol-1-yl]-2-cyclohexyl-ethoxy}-benzoic acid;
4-{2-[2-(4-Chloro-phenyl)-5,6-difluoro-benzoimidazol-1-yl]-2-cyclohexyl-ethoxy}-3-methyl-benzoic acid;

(−)-4-{2-[2-(4-Chloro-phenyl)-5,6-difluoro-benzoimidazol-1-yl]-2-cyclohexyl-ethoxy}-3-methyl-benzoic acid;
(+)-4-{2-[2-(4-Chloro-phenyl)-5,6-difluoro-benzoimidazol-1-yl]-2-cyclohexyl-ethoxy}-3-methyl-benzoic acid;
2-{2-[2-(4-Chloro-phenyl)-5,6-difluoro-benzoimidazol-1-yl]-2-cyclohexyl-ethoxy}-benzoic acid;
3-{2-[2-(4-Chloro-phenyl)-5,6-difluoro-benzoimidazol-1-yl]-2-cyclohexyl-ethoxy}-benzoic acid;
3-{2-[2-(4-Chloro-phenyl)-5,6-difluoro-benzoimidazol-1-yl]-2-cyclohexyl-ethoxy}-4-methyl-benzoic acid;
3-{2-[2-(4-Chloro-phenyl)-5,6-difluoro-benzoimidazol-1-yl]-2-cyclohexyl-ethoxy}-2-methyl-benzoic acid;
5-{2-[2-(4-Chloro-phenyl)-5,6-difluoro-benzoimidazol-1-yl]-2-cyclohexyl-ethoxy}-pyridine-2-carboxylic acid;
6-{2-[2-(4-Chloro-phenyl)-5,6-difluoro-benzoimidazol-1-yl]-2-cyclohexyl-ethoxy}-nicotinic acid;
(+)-6-{2-[2-(4-Chloro-phenyl)-5,6-difluoro-benzoimidazol-1-yl]-2-cyclohexyl-ethoxy}-nicotinic acid;
(−)-6-{2-[2-(4-Chloro-phenyl)-5,6-difluoro-benzoimidazol-1-yl]-2-cyclohexyl-ethoxy}-nicotinic acid;
5-Chloro-6-{2-[2-(4-chloro-phenyl)-5,6-difluoro-benzoimidazol-1-yl]-2-cyclohexyl-ethoxy}-nicotinic acid;
(+)-5-Chloro-6-{2-[2-(4-chloro-phenyl)-5,6-difluoro-benzoimidazol-1-yl]-2-cyclohexyl-ethoxy}-nicotinic acid;
(−)-5-Chloro-6-{2-[2-(4-chloro-phenyl)-5,6-difluoro-benzoimidazol-1-yl]-2-cyclohexyl-ethoxy}-nicotinic acid;
5-{2-[2-(4-Chloro-phenyl)-5,6-difluoro-benzoimidazol-1-yl]-2-cyclohexyl-ethoxy}-4-methyl-pyrimidine-2-carboxylic acid;
4-{2-[2-(4-Chloro-phenyl)-5,6-difluoro-benzoimidazol-1-yl]-2-cyclohexyl-ethoxy}-thieno[3,2-c]pyridine-7-carboxylic acid;
(+)-4-{2-[2-(4-Chloro-phenyl)-5,6-difluoro-benzoimidazol-1-yl]-2-cyclohexyl-ethoxy}-thieno[3,2-c]pyridine-7-carboxylic acid;
(−)-4-{2-[2-(4-Chloro-phenyl)-5,6-difluoro-benzoimidazol-1-yl]-2-cyclohexyl-ethoxy}-thieno[3,2-c]pyridine-7-carboxylic acid;
2-(4-Chloro-phenyl)-1-[1-cyclohexyl-2-(pyridin-2-yloxy)-ethyl]-5,6-difluoro-1H-benzoimidazole;
6-{2-[2-(4-Chloro-phenyl)-5,6-difluoro-benzoimidazol-1-yl]-2-cyclohexyl-ethoxy}-pyridine-2-carboxylic acid;
2-{2-[2-(4-Chloro-phenyl)-5,6-difluoro-benzoimidazol-1-yl]-2-cyclohexyl-ethoxy}-6-methoxy-isonicotinic acid;
4-{2-[2-(4-Chloro-phenyl)-benzoimidazol-1-yl]-2-cyclohexyl-ethoxy}-benzoic acid;
4-{2-[2-(4-Chloro-phenyl)-benzoimidazol-1-yl]-2-cyclohexyl-ethoxy}-3-fluoro-benzoic acid;
2-(4-Chloro-phenyl)-1-[1-cyclohexyl-2-(2-fluoro-phenoxy)-ethyl]-5,6-difluoro-1H-benzoimidazole;
2-(4-Chloro-phenyl)-1-[1-cyclohexyl-2-(pyridin-3-yloxy)-ethyl]-5,6-difluoro-1H-benzoimidazole;
2-(4-Chloro-phenyl)-1-[1-cyclohexyl-2-(pyridin-4-yloxy)-ethyl]-5,6-difluoro-1H-benzoimidazole;
2-{2-[2-(4-Chloro-phenyl)-5,6-difluoro-benzoimidazol-1-yl]-2-cyclohexyl-ethoxy}-isonicotinic acid;
2-(4-Chloro-phenyl)-1-(1-cyclohexyl-2-phenoxy-ethyl)-5,6-difluoro-1H-benzoimidazole;
4-{2-[2-(4-Chloro-phenyl)-5,6-difluoro-benzoimidazol-1-yl]-2-cyclohexyl-ethoxy}-3-trifluoromethyl-benzoic acid;
(+)-4-{2-[2-(4-Chloro-phenyl)-5,6-difluoro-benzoimidazol-1-yl]-2-cyclohexyl-ethoxy}-3-trifluoromethyl-benzoic acid;
(−)-4-{2-[2-(4-Chloro-phenyl)-5,6-difluoro-benzoimidazol-1-yl]-2-cyclohexyl-ethoxy}-3-trifluoromethyl-benzoic acid;
4-{2-[2-(4-Chloro-phenyl)-5,6-difluoro-benzoimidazol-1-yl]-2-cyclohexyl-ethoxy}-2,6-difluoro-benzoic acid;
(+)-4-{2-[2-(4-Chloro-phenyl)-5,6-difluoro-benzoimidazol-1-yl]-2-cyclohexyl-ethoxy}-2,6-difluoro-benzoic acid;
(−)-4-{2-[2-(4-Chloro-phenyl)-5,6-difluoro-benzoimidazol-1-yl]-2-cyclohexyl-ethoxy}-2,6-difluoro-benzoic acid;
(6-{2-[2-(4-Chloro-phenyl)-5,6-difluoro-benzoimidazol-1-yl]-2-cyclohexyl-ethoxy}-pyridin-3-yloxy)-acetic acid;
4-{2-Cyclohexyl-2-[2-(2,6-dimethoxy-pyridin-3-yl)-5,6-difluoro-benzoimidazol-1-yl]-ethoxy}-3-fluoro-benzoic acid;
2-(6-{2-[2-(4-Chloro-phenyl)-5,6-difluoro-benzoimidazol-1-yl]-2-cyclohexyl-ethoxy}-pyridin-3-yloxy)-2-methyl-propionic acid;
(+)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid;
(−)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid;
1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;
(−)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;
(+)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;
4-{2-[2-(4-Chloro-phenyl)-5,6-difluoro-benzoimidazol-1-yl]-2-cyclohexyl-ethoxy}-3,5-dimethyl-benzoic acid;
(+)-4-{2-[2-(4-Chloro-phenyl)-5,6-difluoro-benzoimidazol-1-yl]-2-cyclohexyl-ethoxy}-3,5-dimethyl-benzoic acid;
(−)-4-{2-[2-(4-Chloro-phenyl)-5,6-difluoro-benzoimidazol-1-yl]-2-cyclohexyl-ethoxy}-3,5-dimethyl-benzoic acid;
2-(4-Chloro-phenyl)-1-{1-cyclohexyl-2-[5-(1H-tetrazol-5-yl)-pyridin-2-yloxy]-ethyl}-5,6-difluoro-1H-benzoimidazole;
4-{2-[2-(4-Chloro-phenyl)-5,6-difluoro-benzoimidazol-1-yl]-2-cyclohexyl-1,1-dimethyl-ethoxymethyl}-benzoic acid;
4-{2-[2-(4-Chloro-phenyl)-5,6-difluoro-benzoimidazol-1-yl]-2-cyclohexyl-ethoxymethyl}-benzoic acid;
4-{2-[2-(4-Chloro-phenyl)-5,6-difluoro-benzoimidazol-1-yl]-2-cyclohexyl-ethoxymethyl}-3-fluoro-benzoic acid; and
4-{2-[2-(4-Chloro-phenyl)-5,6-difluoro-benzoimidazol-1-yl]-2-cyclohexyl-ethoxymethyl}-3-methoxy-benzoic acid.

17. A compound according to claim 1, selected from the group consisting of:

4-{2-[2-(4-Chloro-phenyl)-5,6-difluoro-benzoimidazol-1-yl]-2-cyclohexyl-ethoxy}-2,6-dimethyl-benzoic acid;
(+)-2-(4-Chloro-phenyl)-1-{1-cyclohexyl-2-[5-(1H-tetrazol-5-yl)-pyridin-2-yloxy]-ethyl}-5,6-difluoro-1H-benzoimidazole;
(−)-2-(4-Chloro-phenyl)-1-{1-cyclohexyl-2-[5-(1H-tetrazol-5-yl)-pyridin-2-yloxy]-ethyl}-5,6-difluoro-1H-benzoimidazole;
(+)-4-{2-[2-(4-Chloro-phenyl)-5,6-difluoro-benzoimidazol-1-yl]-2-cyclohexyl-ethoxymethyl}-3-fluoro-benzoic acid;
(−)-4-{2-[2-(4-Chloro-phenyl)-5,6-difluoro-benzoimidazol-1-yl]-2-cyclohexyl-ethoxymethyl}-3-fluoro-benzoic acid;
2-(4-Chloro-phenyl)-1-{1-cyclohexyl-2-[2-fluoro-4-(1H-tetrazol-5-yl)-phenoxy]-ethyl}-5,6-difluoro-1H-benzoimidazole;
6-{2-[2-(4-Chloro-phenyl)-5,6-difluoro-benzoimidazol-1-yl]-2-cyclohexyl-ethoxymethyl}-nicotinic acid;
(−)-4-{2-[2-(4-Chloro-phenyl)-5,6-difluoro-benzoimidazol-1-yl]-2-cyclohexyl-ethoxymethyl}-benzoic acid;
(+)-4-{2-[2-(4-Chloro-phenyl)-5,6-difluoro-benzoimidazol-1-yl]-2-cyclohexyl-ethoxymethyl}-benzoic acid;
2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;
(−)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;
(+)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;
6-{2-Cyclohexyl-2-[2-(2,6-dimethoxy-pyridin-3-yl)-5,6-difluoro-benzoimidazol-1-yl]-ethoxy}-nicotinic acid;
(+)-6-{2-Cyclohexyl-2-[2-(2,6-dimethoxy-pyridin-3-yl)-5,6-difluoro-benzoimidazol-1-yl]-ethoxy}-nicotinic acid;
(−)-6-{2-Cyclohexyl-2-[2-(2,6-dimethoxy-pyridin-3-yl)-5,6-difluoro-benzoimidazol-1-yl]-ethoxy}-nicotinic acid;
3-Chloro-4-{2-[2-(4-chloro-phenyl)-5,6-difluoro-benzoimidazol-1-yl]-2-cyclohexyl-ethoxy}-5-fluoro-benzoic acid;
(−)-3-Chloro-4-{2-[2-(4-chloro-phenyl)-5,6-difluoro-benzoimidazol-1-yl]-2-cyclohexyl-ethoxy}-5-fluoro-benzoic acid;
(+)-3-Chloro-4-{(S)-2-[2-(4-chloro-phenyl)-5,6-difluoro-benzoimidazol-1-yl]-2-cyclohexyl-ethoxy}-5-fluoro-benzoic acid;
4-(1-{2-[2-(4-Chloro-phenyl)-5,6-difluoro-benzoimidazol-1-yl]-2-cyclohexyl-ethoxy}-ethyl)-benzoic acid;
2-(4-Chloro-phenyl)-1-{1-cyclohexyl-2-[2-fluoro-4-(1H-tetrazol-5-yl)-phenoxy]-ethyl}-5,6-difluoro-1H-benzoimidazole;
(+)-2-(4-Chloro-phenyl)-1-{1-cyclohexyl-2-[2-fluoro-4-(1H-tetrazol-5-yl)-phenoxy]-ethyl}-5,6-difluoro-1H-benzoimidazole;
(−)-2-(4-Chloro-phenyl)-1-{(S)-1-cyclohexyl-2-[2-fluoro-4-(1H-tetrazol-5-yl)-phenoxy]-ethyl}-5,6-difluoro-1H-benzoimidazole;
4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
(+)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
(−)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid;
4-{2-[2-(4-Chloro-phenyl)-5,6-difluoro-benzoimidazol-1-yl]-2-cyclohexyl-ethoxy}-3,5-difluoro-benzoic acid;
(−)-4-{2-[2-(4-Chloro-phenyl)-5,6-difluoro-benzoimidazol-1-yl]-2-cyclohexyl-ethoxy}-3,5-difluoro-benzoic acid;
(−)-4-{2-[2-(4-Chloro-phenyl)-5,6-difluoro-benzoimidazol-1-yl]-2-cyclohexyl-ethoxy}-3,5-difluoro-benzoic acid;
(+)-2-(4-Chloro-phenyl)-1-{1-cyclohexyl-2-methyl-2-[4-(1H-tetrazol-5-yl)-phenoxy]-propyl}-5,6-difluoro-1H-benzoimidazole;
(−)-2-(4-Chloro-phenyl)-1-{1-cyclohexyl-2-methyl-2-[4-(1H-tetrazol-5-yl)-phenoxy]-propyl}-5,6-difluoro-1H-benzoimidazole;
(+)-4-{2-[2-(4-Chloro-phenyl)-5,6-difluoro-benzoimidazol-1-yl]-2-cyclohexyl-1,1-dimethyl-ethoxy}-benzoic acid;
(−)-4-{2-[2-(4-Chloro-phenyl)-5,6-difluoro-benzoimidazol-1-yl]-2-cyclohexyl-1,1-dimethyl-ethoxy}-benzoic acid;
2-(4-{2-[2-(4-Chloro-phenyl)-5,6-difluoro-benzoimidazol-1-yl]-2-cyclohexyl-ethoxy}-phenoxy)-2-methyl-propionic acid;
(4-{2-[2-(4-Chloro-phenyl)-5,6-difluoro-benzoimidazol-1-yl]-2-cyclohexyl-ethoxy}-phenoxy)-acetic acid;
(4-{2-[2-(4-Chloro-phenyl)-5,6-difluoro-benzoimidazol-1-yl]-2-cyclohexyl-ethoxy}-2-methyl-phenoxy)-acetic acid;
2-(4-{2-[2-(4-Chloro-phenyl)-5,6-difluoro-benzoimidazol-1-yl]-2-cyclohexyl-ethoxy}-2,3-dimethyl-phenoxy)-2-methyl-propionic acid;
2-(4-{2-[2-(4-Chloro-phenyl)-5,6-difluoro-benzoimidazol-1-yl]-2-cyclohexyl-ethoxy}-3-fluoro-phenoxy)-2-methyl-propionic acid;
2-(3-{2-[2-(4-Chloro-phenyl)-5,6-difluoro-benzoimidazol-1-yl]-2-cyclohexyl-ethoxy}-phenoxy)-2-methyl-propionic acid;
4-{2-Cyclohexyl-2-[2-(2,6-dimethoxy-pyridin-3-yl)-5,6-difluoro-benzoimidazol-1-yl]-ethoxy}-3,5-difluoro-benzoic acid;
(+)-4-{2-Cyclohexyl-2-[2-(2,6-dimethoxy-pyridin-3-yl)-5,6-difluoro-benzoimidazol-1-yl]-ethoxy}-3,5-difluoro-benzoic acid;
(−)-4-{2-Cyclohexyl-2-[2-(2,6-dimethoxy-pyridin-3-yl)-5,6-difluoro-benzoimidazol-1-yl]-ethoxy}-3,5-difluoro-benzoic acid;
1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
(+)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
(−)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;
4-{2-[2-(4-Chloro-phenyl)-benzoimidazol-1-yl]-2-cyclohexyl-ethoxy}-3,5-difluoro-benzoic acid;
(+)-4-{2-[2-(4-Chloro-phenyl)-benzoimidazol-1-yl]-2-cyclohexyl-ethoxy}-3,5-difluoro-benzoic acid;
(−)-4-{2-[2-(4-Chloro-phenyl)-benzoimidazol-1-yl]-2-cyclohexyl-ethoxy}-3,5-difluoro-benzoic acid;

4-{2-[2-(4-Chloro-phenyl)-benzoimidazol-1-yl]-2-cyclo-hexyl-ethoxy}-3,5-dimethyl-benzoic acid;
(−)-4-{2-[2-(4-Chloro-phenyl)-benzoimidazol-1-yl]-2-cyclohexyl-ethoxy}-3,5-dimethyl-benzoic acid;
(+)-4-{2-[2-(4-Chloro-phenyl)-benzoimidazol-1-yl]-2-cyclohexyl-ethoxy}-3,5-dimethyl-benzoic acid;
3-Chloro-4-{2-[2-(4-chloro-phenyl)-benzoimidazol-1-yl]-2-cyclohexyl-ethoxy}-5-fluoro-benzoic acid;
(−)-3-Chloro-4-{2-[2-(4-chloro-phenyl)-benzoimidazol-1-yl]-2-cyclohexyl-ethoxy}-5-fluoro-benzoic acid;
(+)-3-Chloro-4-{2-[2-(4-chloro-phenyl)-benzoimidazol-1-yl]-2-cyclohexyl-ethoxy}-5-fluoro-benzoic acid;
2-(4-Chloro-phenyl)-1-{1-cyclohexyl-2-[2,6-dimethyl-4-(1H-tetrazol-5-yl)-phenoxy]-ethyl}-1H-benzoimidazole;
(−)-2-(4-Chloro-phenyl)-1-{1-cyclohexyl-2-[2,6-dimethyl-4-(1H-tetrazol-5-yl)-phenoxy]-ethyl}-1H-benzoimidazole;
(+)-2-(4-Chloro-phenyl)-1-{1-cyclohexyl-2-[2,6-dimethyl-4-(1H-tetrazol-5-yl)-phenoxy]-ethyl}-1H-benzoimidazole;
5-Bromo-6-{2-[2-(4-chloro-phenyl)-5,6-difluoro-benzoimidazol-1-yl]-2-cyclohexyl-ethoxy}-nicotinic acid;
(+)-2-(4-Chloro-phenyl)-1-{1-cyclohexyl-2-[2,6-difluoro-4-(1H-tetrazol-5-yl)-phenoxy]-2-methyl-propyl}-5,6-difluoro-1H-benzoimidazole;
(−)-2-(4-Chloro-phenyl)-1-{1-cyclohexyl-2-[2,6-difluoro-4-(1H-tetrazol-5-yl)-phenoxy]-2-methyl-propyl}-5,6-difluoro-1H-benzoimidazole;
(+)-4-{2-[2-(4-Chloro-phenyl)-5,6-difluoro-benzoimidazol-1-yl]-2-cyclohexyl-1,1-dimethyl-ethoxy}-3,5-difluoro-benzoic acid;
(−)-4-{2-[2-(4-Chloro-phenyl)-5,6-difluoro-benzoimidazol-1-yl]-2-cyclohexyl-1,1-dimethyl-ethoxy}-3,5-difluoro-benzoic acid;
1-(4-{2-[2-(4-Chloro-phenyl)-5,6-difluoro-benzoimidazol-1-yl]-2-cyclohexyl-ethoxy}-phenoxy)-cyclobutanecarboxylic acid;
(+)-1-(4-{2-[2-(4-Chloro-phenyl)-5,6-difluoro-benzoimidazol-1-yl]-2-cyclohexyl-ethoxy}-phenoxy)-cyclobutanecarboxylic acid;
(−)-1-(4-{2-[2-(4-Chloro-phenyl)-5,6-difluoro-benzoimidazol-1-yl]-2-cyclohexyl-ethoxy}-phenoxy)-cyclobutanecarboxylic acid;
1-(4-{2-[2-(4-Chloro-phenyl)-5,6-difluoro-benzoimidazol-1-yl]-2-cyclohexyl-ethoxy}-phenoxy)-cyclopropanecarboxylic acid;
(−)-1-(4-{2-[2-(4-Chloro-phenyl)-5,6-difluoro-benzoimidazol-1-yl]-2-cyclohexyl-ethoxy}-phenoxy)-cyclopropanecarboxylic acid;
(+)-1-(4-{2-[2-(4-Chloro-phenyl)-5,6-difluoro-benzoimidazol-1-yl]-2-cyclohexyl-ethoxy}-phenoxy)-cyclopropanecarboxylic acid;
6-{2-[2-(4-Chloro-2-methyl-phenyl)-5,6-difluoro-benzoimidazol-1-yl]-2-cyclohexyl-ethoxy}-nicotinic acid;
4-{2-[2-(4-Chloro-2-methyl-phenyl)-5,6-difluoro-benzoimidazol-1-yl]-2-cyclohexyl-ethoxy}-3,5-difluoro-benzoic acid;
(−)-4-{2-[2-(4-Chloro-2-methyl-phenyl)-5,6-difluoro-benzoimidazol-1-yl]-2-cyclohexyl-ethoxy}-3,5-difluoro-benzoic acid;
(+)-4-{2-[2-(4-Chloro-2-methyl-phenyl)-5,6-difluoro-benzoimidazol-1-yl]-2-cyclohexyl-ethoxy}-3,5-difluoro-benzoic acid;
2-(4-Chloro-phenyl)-1-{1-cyclohexyl-2-[2,6-difluoro-4-(1H-tetrazol-5-yl)-phenoxy]-ethyl}-5,6-difluoro-1H-benzimidazole;
2-(4-Chloro-phenyl)-1-{1-cyclohexyl-2-[2,6-difluoro-4-(1H-tetrazol-5-yl)-phenoxy]-ethyl}-1H-benzoimidazole;
1-{1-Cyclohexyl-2-[2,6-difluoro-4-(1H-tetrazol-5-yl)-phenoxy]-ethyl}-2-(2,6-dimethoxy-pyridin-3-yl)-5,6-difluoro-1H-benzoimidazole;
6-{2-[2-(4-Chloro-phenyl)-5,6-difluoro-benzoimidazol-1-yl]-2-cycloheptyl-ethoxy}-nicotinic acid;
4-{2-[2-(4-Chloro-phenyl)-5,6-difluoro-benzoimidazol-1-yl]-2-cycloheptyl-ethoxy}-3,5-difluoro-benzoic acid;
(−)-4-{2-[2-(4-Chloro-phenyl)-5,6-difluoro-benzoimidazol-1-yl]-2-cycloheptyl-ethoxy}-3,5-difluoro-benzoic acid;
(+)-4-{2-[2-(4-Chloro-phenyl)-5,6-difluoro-benzoimidazol-1-yl]-2-cycloheptyl-ethoxy}-3,5-difluoro-benzoic acid;
2-(4-Chloro-phenyl)-1-{1-(4,4-difluoro-cyclohexyl)-2-[2,6-dimethyl-4-(1H-tetrazol-5-yl)-phenoxy]-ethyl}-5,6-difluoro-1H-benzoimidazole;
2-(4-Chloro-phenyl)-1-{1-cyclopentyl-2-[2,6-dimethyl-4-(1H-tetrazol-5-yl)-phenoxy]-ethyl}-5,6-difluoro-1H-benzoimidazole;
2-(4-Chloro-phenyl)-1-{1-cyclopropyl-2-[2,6-dimethyl-4-(1H-tetrazol-5-yl)-phenoxy]-ethyl}-5,6-difluoro-1H-benzoimidazole;
(+)-4-{2-[2-(4-Chloro-phenyl)-5,6-difluoro-benzoimidazol-1-yl]-(2-cis-cyclohexyl-ethylamino)}-cyclohexanecarboxylic acid;
(−)-4-{2-[2-(4-Chloro-phenyl)-5,6-difluoro-benzoimidazol-1-yl]-(2-cis-cyclohexyl-ethylamino)}-cyclohexanecarboxylic acid;
(+)-4-{2-[2-(4-Chloro-phenyl)-5,6-difluoro-benzoimidazol-1-yl]-(2-trans-cyclohexyl-ethylamino)}-cyclohexanecarboxylic acid;
(−)-4-{2-[2-(4-Chloro-phenyl)-5,6-difluoro-benzoimidazol-1-yl]-(2-trans-cyclohexyl-ethylamino)}-cyclohexanecarboxylic acid;
{2-[2-(4-Chloro-phenyl)-5,6-difluoro-benzoimidazol-1-yl]-2-cyclohexyl-ethyl}-[4-(1H-tetrazol-5-yl)-phenyl]-amine;
4-{2-[2-(4-Chloro-phenyl)-5,6-difluoro-benzoimidazol-1-yl]-2-cyclohexyl-ethylsulfanyl}-benzoic acid;
4-{2-[2-(4-Chloro-phenyl)-5,6-difluoro-benzoimidazol-1-yl]-2-cyclohexyl-ethanesulfonyl}-benzoic acid;
4-[3-Cyclohexyl-3-(5,6-difluoro-2-phenyl-benzoimidazol-1-yl)-propyl]-benzoic acid;
(−)-4-[3-Cyclohexyl-3-(5,6-difluoro-2-phenyl-benzoimidazol-1-yl)-propyl]-benzoic acid;
(+)-4-[3-Cyclohexyl-3-(5,6-difluoro-2-phenyl-benzoimidazol-1-yl)-propyl]-benzoic acid;
4-{3-Cyclohexyl-3-[2-(2,6-dimethoxy-pyridin-3-yl)-5,6-difluoro-benzoimidazol-1-yl]-propyl}-benzoic acid;
(−)-4-{3-Cyclohexyl-3-[2-(2,6-dimethoxy-pyridin-3-yl)-5,6-difluoro-benzoimidazol-1-yl]-propyl}-benzoic acid; and
(+)-4-{3-Cyclohexyl-3-[2-(2,6-dimethoxy-pyridin-3-yl)-5,6-difluoro-benzoimidazol-1-yl]-propyl}-benzoic acid.

18. A compound according to claim 1, selected from the group consisting of:
(+)-4-{2-[2-(4-Chloro-phenyl)-5,6-difluoro-benzoimidazol-1-yl]-2-cyclohexyl-ethoxy}-benzoic acid;
(−)-4-{2-[2-(4-Chloro-phenyl)-5,6-difluoro-benzoimidazol-1-yl]-2-cyclohexyl-ethoxy}-3-fluoro-benzoic acid;
(+)-6-{2-[2-(4-Chloro-phenyl)-5,6-difluoro-benzoimidazol-1-yl]-2-cyclohexyl-ethoxy}-nicotinic acid;

(−)-4-{2-[2-(4-Chloro-phenyl)-5,6-difluoro-benzoimidazol-1-yl]-2-cyclohexyl-ethoxy}-3-trifluoromethyl-benzoic acid;

(−)-4-{2-[2-(4-Chloro-phenyl)-5,6-difluoro-benzoimidazol-1-yl]-2-cyclohexyl-ethoxy}-2,6-difluoro-benzoic acid;

(−)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;

(+)-1-(6-{2-[2-(4-Chloro-phenyl)-5,6-difluoro-benzoimidazol-1-yl]-2-cyclohexyl-ethoxy}-pyridin-3-yloxy)-cyclopropanecarboxylic acid;

(−)-4-{2-[2-(4-Chloro-phenyl)-5,6-difluoro-benzoimidazol-1-yl]-2-cyclohexyl-ethoxy}-3,5-dimethyl-benzoic acid;

4-{2-[2-(4-Chloro-phenyl)-5,6-difluoro-benzoimidazol-1-yl]-2-cyclohexyl-ethoxymethyl}-benzoic acid;

4-{2-[2-(4-Chloro-phenyl)-5,6-difluoro-benzoimidazol-1-yl]-2-cyclohexyl-ethoxymethyl}-3-fluoro-benzoic acid; and (−)-2-(6-{2-[2-(4-Chloro-phenyl)-5,6-difluoro-benzoimidazol-1-yl]-2-cyclohexyl-ethoxy}-pyridin-3-yloxy)-2-methyl-propionic acid.

19. A compound according to claim 1, selected from the group consisting of:

(+)-4-{2-[2-(4-Chloro-phenyl)-5,6-difluoro-benzoimidazol-1-yl]-2-cyclohexyl-ethoxy}-3,5-dimethyl-benzoic acid;

(+)-2-(4-Chloro-phenyl)-1-{1-cyclohexyl-2-[2,6-dimethyl-4-(1H-tetrazol-5-yl)-phenoxy]-ethyl}-5,6-difluoro-1H-benzoimidazole;

(−)-3-Chloro-4-{2-[2-(4-chloro-phenyl)-5,6-difluoro-benzoimidazol-1-yl]-2-cyclohexyl-ethoxy}-5-fluoro-benzoic acid;

(−)-2-(4-Chloro-phenyl)-1-{(S)-1-cyclohexyl-2-[2-fluoro-4-(1H-tetrazol-5-yl)-phenoxy]-ethyl}-5,6-difluoro-1H-benzoimidazole;

(+)-4-{2-Cyclohexyl-2-[2-(2,6-dimethoxy-pyridin-3-yl)-5,6-difluoro-benzoimidazol-1-yl]-ethoxy}-3,5-dimethyl-benzoic acid;

(−)-4-{2-[2-(4-Chloro-phenyl)-5,6-difluoro-benzoimidazol-1-yl]-2-cyclohexyl-ethoxy}-3,5-difluoro-benzoic acid;

(−)-4-{2-Cyclohexyl-2-[2-(2,6-dimethoxy-pyridin-3-yl)-5,6-difluoro-benzoimidazol-1-yl]-ethoxy}-3,5-difluoro-benzoic acid;

(−)-1-{1-Cyclohexyl-2-[2,6-dimethyl-4-(1H-tetrazol-5-yl)-phenoxy]-ethyl}-2-(2,6-dimethoxy-pyridin-3-yl)-5,6-difluoro-1H-benzoimidazole;

(−)-3-Chloro-4-{2-[2-(4-chloro-phenyl)-benzoimidazol-1-yl]-2-cyclohexyl-ethoxy}-5-fluoro-benzoic acid;

(+)-2-(4-Chloro-phenyl)-1-{1-cyclohexyl-2-[2,6-dimethyl-4-(1H-tetrazol-5-yl)-phenoxy]-ethyl}-1H-benzoimidazole;

2-(4-Chloro-phenyl)-1-{1-cyclohexyl-2-[2,6-difluoro-4-(1H-tetrazol-5-yl)-phenoxy]-ethyl}-5,6-difluoro-1H-benzimidazole;

2-(4-Chloro-phenyl)-1-{1-(4,4-difluoro-cyclohexyl)-2-[2,6-dimethyl-4-(1H-tetrazol-5-yl)-phenoxy]-ethyl}-5,6-difluoro-1H-benzoimidazole;

(+)-4-{2-[2-(4-Chloro-phenyl)-5,6-difluoro-benzoimidazol-1-yl]-(2-trans-cyclohexyl-ethylamino)}-cyclohexanecarboxylic acid;

(−)-4-{2-[2-(4-Chloro-phenyl)-5,6-difluoro-benzoimidazol-1-yl]-(2-trans-cyclohexyl-ethylamino)}-cyclohexanecarboxylic acid;

{2-[2-(4-Chloro-phenyl)-5,6-difluoro-benzoimidazol-1-yl]-2-cyclohexyl-ethyl}-[4-(1H-tetrazol-5-yl)-phenyl]-amine;

(−)-4-[3-Cyclohexyl-3-(5,6-difluoro-2-phenyl-benzoimidazol-1-yl)-propyl]-benzoic acid; and (+)-4-{3-Cyclohexyl-3-[2-(2,6-dimethoxy-pyridin-3-yl)-5,6-difluoro-benzoimidazol-1-yl]-propyl}-benzoic acid.

20. A pharmaceutical composition comprising a compound of claim 1 and a pharmaceutically acceptable excipient.

21. A process for the manufacture of a compound of formula (I) as defined in claim 1, which process comprises one of the following steps:

(a) the reaction of a compound of formula (II)

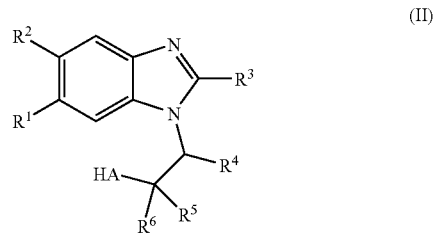

(II)

with a compound of formula $R^7(CH_2)_nX$, optionally followed by the reaction of the resulting product in the presence of base or acid, wherein A, $R^1$ to $R^7$ and n are as defined in claim 1 and wherein X is a leaving group; or (b) the reaction of a compound of formula (III)

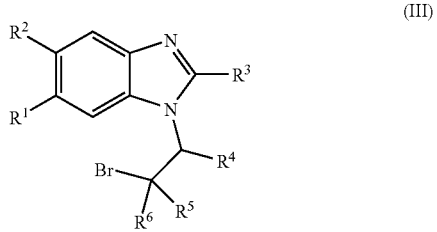

(III)

with a compound of formula $R^7(CH_2)_nAH$, optionally followed by the reaction of the resulting product in the presence of base or acid, wherein A, $R^1$ to $R^7$ and n are as defined in claim 1.

* * * * *